US008158858B2

(12) United States Patent
Li

(10) Patent No.: US 8,158,858 B2
(45) Date of Patent: Apr. 17, 2012

(54) SOYBEAN PROMOTERS AND FLOWER-PREFERRED EXPRESSION THEREOF IN TRANSGENIC PLANTS

(75) Inventor: Zhongsen Li, Hockessin, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 878 days.

(21) Appl. No.: 12/080,113

(22) Filed: Mar. 31, 2008

(65) Prior Publication Data

US 2009/0070893 A1 Mar. 12, 2009

Related U.S. Application Data

(60) Provisional application No. 60/921,703, filed on Apr. 4, 2007.

(51) Int. Cl.

| | |
|---|---|
| ***A01H 1/00*** | (2006.01) |
| ***C07H 21/04*** | (2006.01) |
| *C07K 14/415* | (2006.01) |
| *C12N 15/00* | (2006.01) |

(52) U.S. Cl. ......... 800/295; 435/6.1; 435/468; 435/410; 435/419; 435/320.1; 536/24.1; 800/278

(58) Field of Classification Search .................. 435/6.1, 435/468, 410, 419, 320.1; 536/24.1; 800/278, 800/295

See application file for complete search history.

(56) References Cited

U.S. PATENT DOCUMENTS

| | | | |
|---|---|---|---|
| 4,945,050 | A | 7/1990 | Sanford et al. |
| 5,004,863 | A | 4/1991 | Umbeck |
| 5,107,065 | A | 4/1992 | Sjewmaker et al. |
| 5,159,135 | A | 10/1992 | Umbeck |
| 5,231,020 | A | 7/1993 | Jorgensen et al. |
| 5,416,011 | A | 5/1995 | Hinchee et al. |
| 5,463,174 | A | 10/1995 | Moloney et al. |
| 5,569,834 | A | 10/1996 | Hinchee et al. |
| 6,072,050 | A | 6/2000 | Bowen et al. |

FOREIGN PATENT DOCUMENTS

| | | | |
|---|---|---|---|
| WO | WO9217598 | A1 | 10/1992 |
| WO | WO9836083 | A1 | 8/1998 |
| WO | WO9953050 | A1 | 10/1999 |
| WO | WO0037662 | A2 | 6/2000 |
| WO | WO0200904 | A2 | 1/2002 |

OTHER PUBLICATIONS

Odell et al., "Identification of DNA sequences required for activity of the cauliflower mosaic virus 35S promoter," Nature vol. 313. pp. 810-812 (1985).

P. R. Ebert et al., "Identification of an Essential upstream element in the nopaline synthase . . . ," Proc. Natl. Acad. Sci. U.S.A., vol. 84, pp. 5745-5749 (1987).

R. A. Jefferson et al., "GUS fusions: β-glucuronidase as a sensitive and versatile gene fusion maker in higher plants," EMBO J. vol. 6, No. 13, pp. 3901-3907 (1987).

Klein et al., "High-Velocity microprojectiles for delivering nucleic acids into living cells," Letter of Nature (London) vol. 327, pp. 70-73 (1987).

Lawton et al., "Expression of a soybean β-conclycinin gene under the control of the Cauliflower Mosiac Virus 35S and 19S . . . ," Plant Mol. Biol. 9:315-324 (1987).

J. C. Walker et al., "DNA sequences required for anaerobic expression of the maize alcohol dehydrogenase 1 gene," Proc. Natl. Acad. Sci. vol. 84, pp. 6624-6628 (1987).

Raschke et al., "Nucleotide Sequence Analysis of Soybean Small Heat Shock Protein Genes Belonging to two Different Multigene . . . ," J. Mol. Biol. 199(4), pp. 549-557 (1988).

V. L. Chandler et al., "Two Regulartory Genes of the Maize Anthocyanin Pathway Are Homologous: Isolation of B Utilizing R Genomic . . . ," Plant Cell, vol. 1, pp. 1175-1183 (1989).

J. K. Okamuro et al, "Regulation of plant gene expression: general principles," Biochemistry of Plants 15:1 82 (1989).

M. J. Battraw et al., "Histochemical analysis of CaMV 35S promoter-β-glucuronidase gene expression in transgenic rice plants," Plant Mol. Biol. 15:527-538 (1990).

J. Callis et al., "Ubiquitin Extension Proteins of *Arabidopsis thaliana*," J. Biol. Chem. 265(21):12486-12493 (1990).

Neuhaus et al., "Plants transformation by microinjection techniques," Physiol. Plant. 79:213-217 (1990).

M. Sanger et al., "Characteristics of a strong promoter from figwort mosaic virus: comparison with the analogous 35S promoter . . . ," Plant Mol. Biol. 14:433-443 (1990).

N. S. Yang et al., "Maize sucrose synthase-1 promoter directs phloem cell-specific expression of Gus gene . . . ," Proc. Natl. Acad. Sci. 87:4144-4148 (Jun. 1990).

Pelese-Siebenbourg et al., "A pair of genes coding for lipid-transfer proteins in *Sorghum vulgare*," Gene 148:305-308 (1994).

A. L. Plant et al., "Regulation of an *Arabidopsis oleosin*gene promoter in transgenic *Brassica napus*," Plant Mol. Biol. 25:193-205 (1994).

S. Thoma et al., Tissue-Specific Expression of a Gene Encoding a Cell Wall-Localized Lipid Transfer Protein from Arabidopsis, Plant Physiol. 105:35-45 (1994).

Vignols et al., "Characterization of a rice gene coding for a lipid transfer protein," Gene 142:265-270 (1994).

S. Holtorf et al., "Comparison of different constitutive and inducible promoters for the . . . *Arabidopsis thaliana*," Plant Mol. Biol. 29:637-646 (1995).

Pellegrineschi et al., "Expression of horseradish peroxidase in transgenic tobacco," Biochem. Soc. Trans. 23(2):247-250 (1995).

A. Wilmink et al., "Activity of constitutive promoters in various species from the Liliaceae," Plant Mol. Biol. 28:949-955 (1995).

Jean-Claude Kader, "Lipid-Transfer Proteins in Plants," Annu. Rev. Plant Physiol. Plant Mol. Biol. 47: 627-654 (1996).

Zhongsen Li, "Iolation and Characterizationof Arabidopsis," Texas A&M Univ., May 1997.

M. A. J. Toonen et al., "AtLTP1 luciferase expression during carrot somatic embryogenesis," Plant Journal 12(5):1213-1221 (1997).

R. Atanassova et al., "Functional analysis of the promoter region of a maize (*Zea mays* L.) H3 histone gene in transgenic Arabidopsis . . . ," Plant Mol. Biol. 37:275-285 (1998).

(Continued)

*Primary Examiner* — Phuong Bui

(57) ABSTRACT

The promoters of a soybean lipid transfer protein LTP1 and fragments thereof and their use in promoting the expression of one or more heterologous nucleic acid fragments in plants are described.

Figure 1:
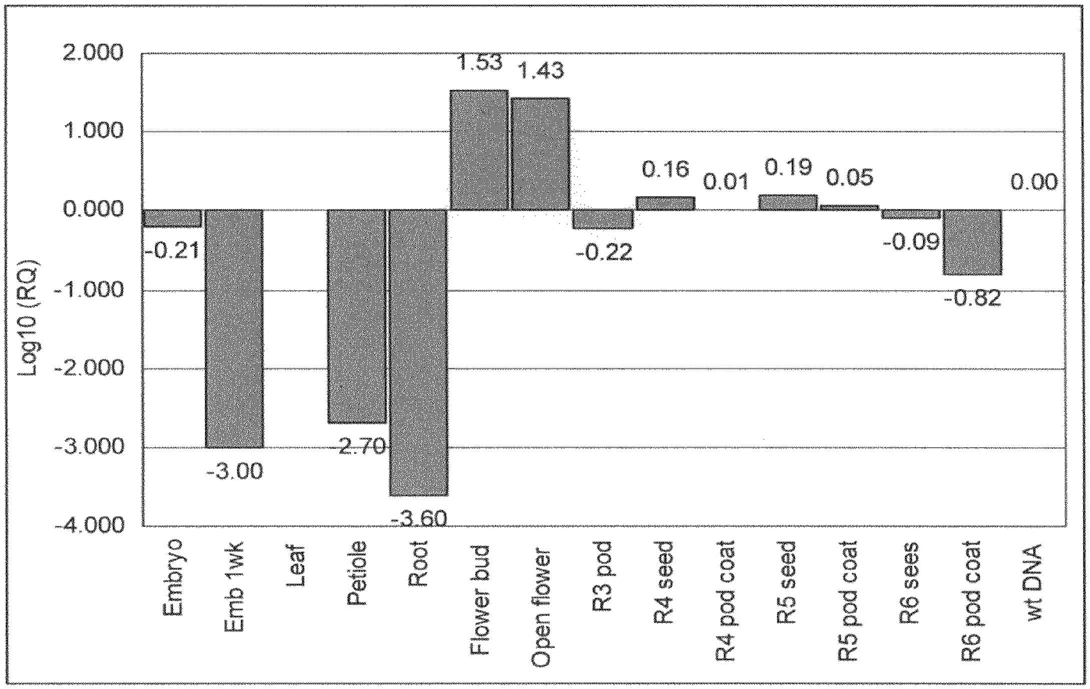

21 Claims, 7 Drawing Sheets
(2 of 7 Drawing Sheet(s) Filed in Color)

OTHER PUBLICATIONS

T. Elmayan et al., "Arabidopsis Mutants Impaired in Cosuppression," Plant Cell 10:1747-1757 (Oct. 1998).

Rollfinke et al., "Characterization and expression of a heptaubiquitin gene from tomato," Gene 211:267-276 (1998).

A. K. Sohal et al., "The promoter of a *Brassica napus* lipid transfer protein gene is active in a range of tissues . . . transgenic Arabidopsis," Plant Mol. Biol. 41:75-87 (1999).

I. Sabala et al., "Tissue-specific expression of Pa18, a putative lipid transfer protein gene, during embryo . . . (*Picea abies*)," Plant Mol. Biol. 42:461-478 (2000).

H. Chang et al., "Overproduction of Cytokinins in Petunia Flowers Transformed with PSAG12-IPT Delays Corolla . . . Sensitivity to Ethylene," Plant Physiol. 132:2174-2183 (Aug. 2003).

T. Kakimoto, "Biosynthesis of cytokinins," J. Plant Res. 116:233-239 (2003).

E. Yubero-Serrano et al, "Identification of a strawberry gene encoding a non-specific lipid transnfer protein that responds to ABA, . . . ," J. Exp. Bot. 54:1865-1877 (2003).

C. Espinosa-Soto et al., "A Gene Regulatory Network Model for Cell-Fate Determination during Arabidopsis . . . Gene Expression Profiles,," Plant Cell 16:2923-2939 (Nov. 2004).

S. Mori et al., "Heterologous expression of the flavonoid 3,5,-hydroxylase gene of *Vinca major* alters . . . transgenic Petunia hybrida," Plant Cell Reports 22:415-421 (2004).

T. E. Young et al., "Senescence-induced expression of cytokinin reverses pistil abortion during maize flower development," Plant Journal, 38:910-922 (2004).

M. L. Federico et al., "The complex development expression of a novel stress-responsive barley Ltp gene is determined by a . . . sequence," Plant Mol. Biol. 57:35-51 (2005).

Y. Tanaka et al., "Genetic engineering in floriculture," Plant Cell, Tissue and Organ Culture 80:1-24 (2005).

Copending U.S. Appl. No. 12/152,375, filed May 14, 2008.

Copending U.S. Appl. No. 12/152,369, filed May 14, 2008.

SOYBEAN PROMOTERS AND FLOWER-PREFERRED EXPRESSION THEREOF IN TRANSGENIC PLANTS

CROSS-REFERENCE TO RELATED APPLICATION

This application claims the benefit of U.S. Provisional Application No. 60/921,703 filed Apr. 4, 2007, which is incorporated by reference herein in its entirety.

FIELD OF THE INVENTION

The present invention relates to the field of plant molecular biology, more particularly to regulation of gene expression in plants.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a chimeric gene (or genes) introduced into a plant are controlled using promoters, there is an ongoing interest in the isolation of novel promoters that are capable of controlling the expression of a chimeric gene (or genes) at certain levels in specific tissue types or at specific plant developmental stages.

Among the most commonly used promoters are the nopaline synthase (NOS) promoter (Ebert et al., Proc. Natl. Acad. Sci. U.S.A. 84:5745-5749 (1987)); the octapine synthase (OCS) promoter, caulimovirus promoters such as the cauliflower mosaic virus (CaMV) 19S promoter (Lawton et al., Plant Mol. Biol. 9:315-324 (1987)); the CaMV 35S promoter (Odell et al., Nature 313:810-812 (1985)), and the figwort mosaic virus 35S promoter; the light inducible promoter from the small subunit of rubisco (Pellegrineschi et al., Biochem. Soc. Trans. 23(2):247-250 (1995)); the Adh promoter (Walker et al., Proc. Natl. Acad. Sci. U.S.A. 84:6624-66280 (1987)); the sucrose synthase promoter (Yang et al., Proc. Natl. Acad. Sci. U.S.A. 87:4144-4148 (1990)); the R gene complex promoter (Chandler et al., Plant Cell 1:1175-1183 (1989)); the chlorophyll a/b binding protein gene promoter; and the like.

A flower is a complex structure consisting of pedicel, sepal, petal, stamen, and carpel. A stamen comprises an anther, pollen and filament. A carpel comprises a stigma, style and ovary. An ovary comprises an ovule, embryo sac, and egg cell. Flower promoters in general include promoters that direct gene expression in any of the above tissues or cell types.

Lipid transfer protein (LTP) genes have been isolated from barley (Federico et al., Plant Mol. Biol. 57:35-51 (2005)), strawberry (Yubero-Serrano et al, J. Exp. Bot. 54:1865-1877 (2003)), *Arabidopsis* (Thoma et al., Plant Physiol. 105:35-45 (1994)), Norway spruce (Sabala et al., Plant Mol. Biol. 42:461-478 (2000)), rice (Vignols et al., Gene 142:265-270 (1994)), carrot (Toonen et al., Plant J. 12:1213-1221 (1997)), *Brassica napus* (Sohal et al., Plant Mol. Biol. 41:75-87 (1999)), *Sorghum vulgare* (Pelese-Siebenbourg et al., Gene 148:305-308 (1994)), and other plant species. The reported LTP genes are known to have various expression patterns in respective plants. However, there remains a lack of soybean LTP genes or flower-preferred expression of LTP genes.

Although advances in technology provide greater success in transforming plants with chimeric genes, there is still a need for preferred expression of such genes in desired plants. Often times it is desired to selectively express target genes in a specific tissue because of toxicity or efficacy concerns. For example, flower tissue is a type of tissue where preferred expression is desirable and there remains a need for promoters that preferably initiate transcription in flower tissue. Promoters that initiate transcription preferably in flower tissue control genes involved in flower development and flower abortion.

SUMMARY OF THE INVENTION

Compositions and methods for regulating gene expression in a plant are provided. One aspect is for an isolated polynucleotide comprising: a) a nucleotide sequence comprising the sequence set forth in SEQ ID NO:1 or a full-length complement thereof; b) a nucleotide sequence comprising a fragment of SEQ ID NO:1, SEQ ID NO:2, SEQ ID NO:3, SEQ ID NO:4, or SEQ ID NO:5; or c) a nucleotide sequence comprising a sequence having at least 90% sequence identity, based on the BLASTN method of alignment, when compared to the sequence set forth in SEQ ID NO:1; wherein said nucleotide sequence is a promoter.

Other embodiments include recombinant DNA constructs comprising a polynucleotide sequence of the present invention operably linked to a heterologous sequence. Additionally, some embodiments provide for transgenic plant cells, transient and stable, transgenic plant seeds, as well as transgenic plants comprising the provided recombinant DNA constructs.

There are provided some embodiments that include methods of expressing a coding sequence or a functional RNA in a flowering plant comprising: introducing a recombinant DNA construct described above into the plant, wherein the heterologous sequence comprises a coding sequence; growing the plant; and selecting a plant displaying expression of the coding sequence or the functional RNA of the recombinant DNA construct.

Furthermore, some embodiments of the present invention include methods of transgenically altering a marketable flower trait of a flowering plant, comprising: introducing a recombinant DNA construct described above into the flowering plant; growing a fertile, mature flowering plant resulting from the introducing step; and selecting a flowering plant expressing the heterologous nucleotide sequence in flower tissue based on the altered marketable flower trait.

Another aspect is for an isolated polynucleotide comprising: (a) a nucleotide sequence encoding a polypeptide having lipid transfer protein activity, wherein the polypeptide has at least 90% sequence identity, based on the Clustal method of alignment, when compared to the sequence set forth in SEQ ID NO:36, or (b) a full-length complement of the nucleotide sequence of (a).

A further aspect is for an isolated polypeptide having lipid transfer protein activity, wherein the isolated polypeptide has at least 90% sequence identity, based on the Clustal method of alignment, when compared to the sequence set forth in SEQ ID NO:36.

BRIEF DESCRIPTION OF SEQUENCES AND DRAWINGS

The patent or application file contains at least one drawing executed in color. Copies of this patent or application publication with color drawing(s) will be provided by the Office upon request and payment of necessary fee.

The invention can be more fully understood from the following detailed description, the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO:1 is a DNA sequence comprising a 1136 nucleotide soybean LTP1 promoter (or full-length LTP1 promoter).

SEQ ID NO:2 is a 927 basepair truncated form of the LTP1 promoter shown in SEQ ID NO:1 (bp 209-1136 of SEQ ID NO:1).

SEQ ID NO:3 is a 738 basepair truncated form of the LTP1 promoter shown in SEQ ID NO:1 (bp 398-1136 of SEQ ID NO:1).

SEQ ID NO:4 is a 527 basepair truncated form of the LTP1 promoter shown in SEQ ID NO:1 (bp 609-1136 of SEQ ID NO:1).

SEQ ID NO:5 is a 257 basepair truncated form of the LTP1 promoter shown in SEQ ID NO:1 (bp 879-1136 of SEQ ID NO:1).

SEQ ID NO:6 is an oligonucleotide primer used in the PCR amplifications of the full length LTP1 promoter in SEQ ID NO:1 when paired with SEQ ID NO:7, and the truncated LTP1 promoters in SEQ ID NOs: 2, 3, 4, or 5 when paired with SEQ ID NOs: 8, 9, 10, or 11, respectively.

SEQ ID NO:7 is an oligonucleotide primer used in the PCR amplification of the full length LTP1 promoter in SEQ ID NO:1 when paired with SEQ ID NO:6.

SEQ ID NO:8 is an oligonucleotide primer used in the PCR amplification of the truncated LTP1 promoter in SEQ ID NO:2 when paired with SEQ ID NO:6.

SEQ ID NO:9 is an oligonucleotide primer used in the PCR amplification of the truncated LTP1 promoter in SEQ ID NO:3 when paired with SEQ ID NO:6.

SEQ ID NO:10 is an oligonucleotide primer used in the PCR amplification of the truncated LTP1 promoter in SEQ ID NO:4 when paired with SEQ ID NO:6.

SEQ ID NO:11 is an oligonucleotide primer used in the PCR amplification of the truncated LTP1 promoter in SEQ ID NO:5 when paired with SEQ ID NO:6.

SEQ ID NO:12 is an oligonucleotide primer specific to the soybean LTP1 gene used in the first nested PCR amplification of the LTP1 promoter when paired with SEQ ID NO:13.

SEQ ID NO:13 is an oligonucleotide primer used in the first nested PCR amplification of the LTP1 promoter when paired with SEQ ID NO:12.

SEQ ID NO:14 is an oligonucleotide primer specific to the soybean LTP1 gene used in the second nested PCR amplification of the LTP1 promoter when paired with SEQ ID NO:15.

SEQ ID NO:15 is an oligonucleotide primer used in the second nested PCR amplification of the LTP1 promoter when paired with SEQ ID NO:14.

SEQ ID NO:16 is the nucleotide sequence of the soybean lipid transfer protein cDNA (LTP1). Nucleotides 1 to 69 are the 5' untranslated sequence, nucleotides 70 to 72 are the translation initiation codon, nucleotides 70 to 444 are polypeptide coding region, nucleotides 445 to 447 are the termination codon, and nucleotides 448 to 573 are part of the 3' untranslated sequence.

SEQ ID NO:17 is the 8638 bp sequence of QC267.

SEQ ID NO:18 is the 4794 bp sequence of QC267-1Y.

SEQ ID NO:19 is an oligonucleotide primer used in the diagnostic PCR to check for soybean genomic DNA presence in total RNA or cDNA when paired with SEQ ID NO:20.

SEQ ID NO:20 is an oligonucleotide primer used in the diagnostic PCR to check for soybean genomic DNA presence in total RNA or cDNA when paired with SEQ ID NO:19.

SEQ ID NO:21 is the longer strand sequence of the adaptor supplied in ClonTech™ GenomeWalker™ kit.

SEQ ID NO:22 is an oligonucleotide primer specific to the soybean LTP1 promoter 5' end for the amplification of the LTP1 promoter when paired with SEQ ID NO:23. An XmaI restriction site CCCGGG is added for subsequent cloning.

SEQ ID NO:23 is an oligonucleotide primer specific to the soybean LTP1 promoter 3' end for the amplification of the LTP1 promoter when paired with SEQ ID NO:22. An XmaI restriction site CCCGGG is added for subsequent cloning.

SEQ ID NO:24 is an MPSS tag sequence that is specific to the unique gene PSO330124.

SEQ ID NO:25 is a sense primer used in quantitative PCR analysis of SAMS:ALS transgene.copy numbers.

SEQ ID NO:26 is a FAM labeled fluorescent DNA oligo probe used in quantitative PCR analysis of SAMS:ALS transgene.copy numbers.

SEQ ID NO:27 is an antisense primer used in quantitative PCR analysis of SAMS:ALS transgene.copy numbers.

SEQ ID NO:28 is a sense primer used in quantitative PCR analysis of GM-LTP1:YFP transgene.copy numbers.

SEQ ID NO:29 is a FAM labeled fluorescent DNA oligo probe used in quantitative PCR analysis of GM-LTP1:YFP transgene.copy numbers.

SEQ ID NO:30 is an antisense primer used in quantitative PCR analysis of GM-LTP1:YFP transgene.copy numbers.

SEQ ID NO:31 is a sense primer used as an endogenous control gene primer in quantitative PCR analysis of transgene.copy numbers.

SEQ ID NO:32 is a VIC labeled DNA oligo probe used as an endogenous control gene probe in quantitative PCR analysis of transgene.copy numbers.

SEQ ID NO:33 is an antisense primer used as an endogenous control gene primer in quantitative PCR analysis of transgene.copy numbers.

SEQ ID NO:34 is the recombination site attB1 sequence in the Gateway cloning system (Invitrogen).

SEQ ID NO:35 is the recombination site attB2 sequence in the Gateway cloning system (Invitrogen).

SEQ ID NO:36 is the 125 amino acid long putative PSO330124 translation product LTP1 protein sequence.

SEQ ID NO:37 is the 7499 bp sequence of QC258.

SEQ ID NO:38 is the 2817 bp sequence of pCR8/GW/TOPO.

SEQ ID NO:39 is the 3953 bp sequence of QC267-1.

SEQ ID NO:40 is the 3744 bp sequence of QC267-2.

SEQ ID NO:41 is the 3555 bp sequence of QC267-3.

SEQ ID NO:42 is the 3344 bp sequence of QC267-4.

SEQ ID NO:43 is the 3074 bp sequence of QC267-5.

SEQ ID NO:44 is the 4585 bp sequence of QC267-2Y.

SEQ ID NO:45 is the 4396 bp sequence of QC267-3Y.

SEQ ID NO:46 is the 4185 bp sequence of QC267-4Y.

SEQ ID NO:47 is the 3915 bp sequence of QC267-5Y.

SEQ ID NO:48 is the 5286 bp sequence of QC330.

SEQ ID NO:49 is the 4157 bp sequence of pZSL90.

SEQ ID NO:50 is the 3291 bp sequence of QC299i.

FIG. 1 displays the logarithm of relative quantifications of LTP1 gene expression in 14 different soybean tissues by quantitative RT-PCR. The gene expression profile indicates that the LTP1 gene is highly expressed in flower buds and open flowers.

Figure 2:
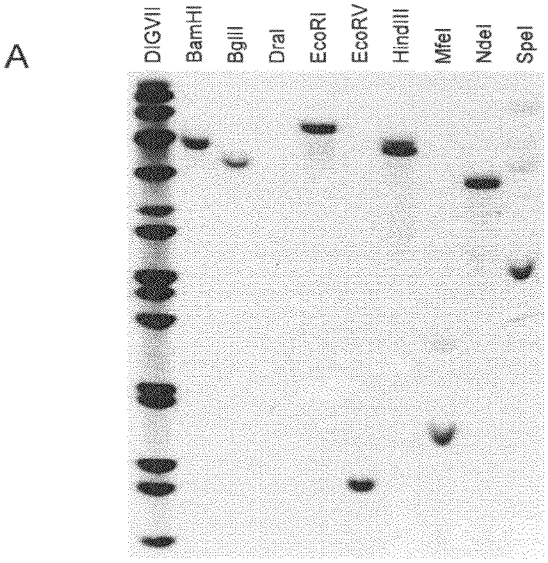
Figure 2:
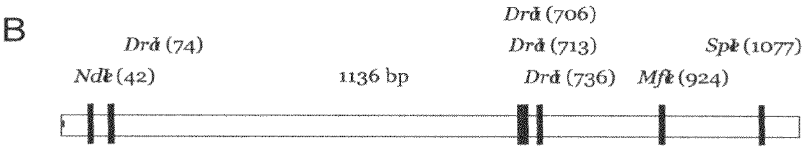

FIG. 2 displays the LTP1 promoter copy number analysis by Southern hybridization. Also displayed is a schematic of the LTP1 promoter showing relative linear position of a number of restriction sites.

Figure 3:
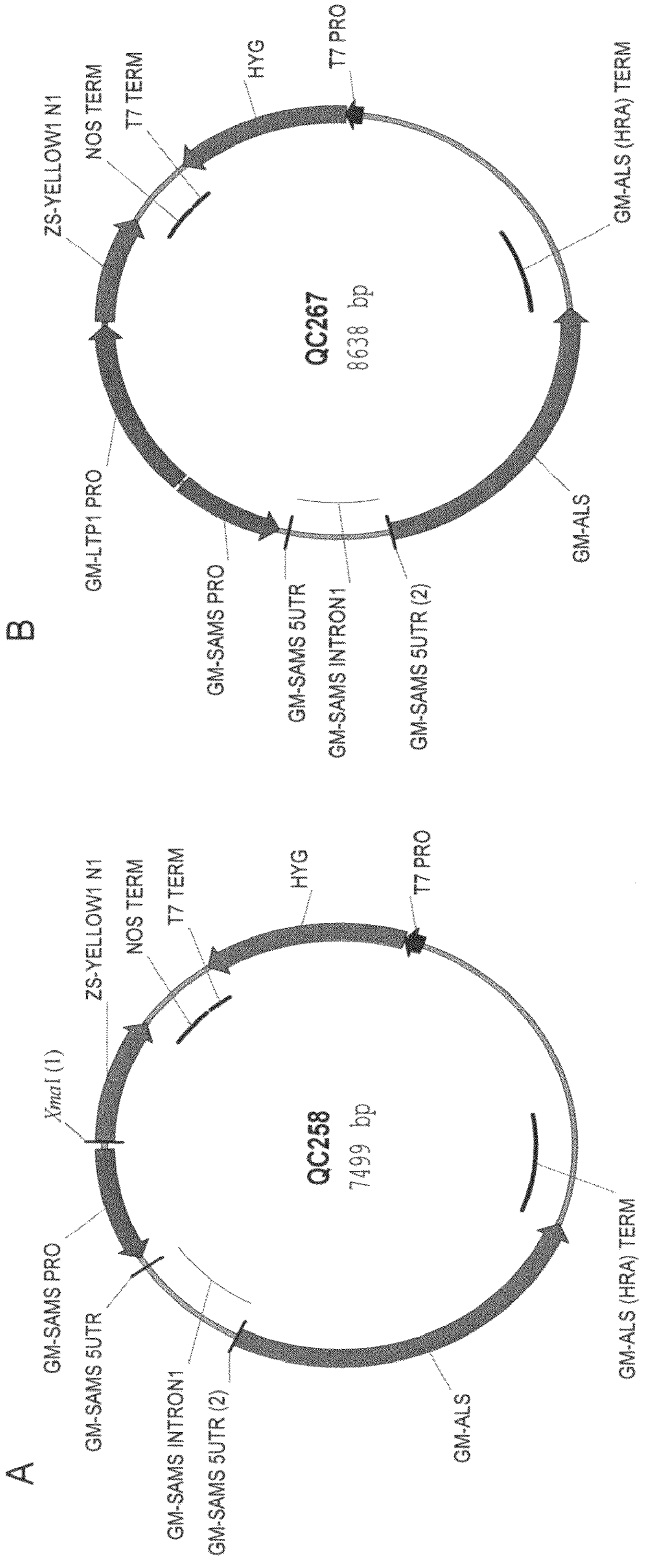

FIG. 3 is a schematic representation of the map of plasmid QC258 (FIG. 3A) and QC267 (FIG. 3B).

Figure 4:
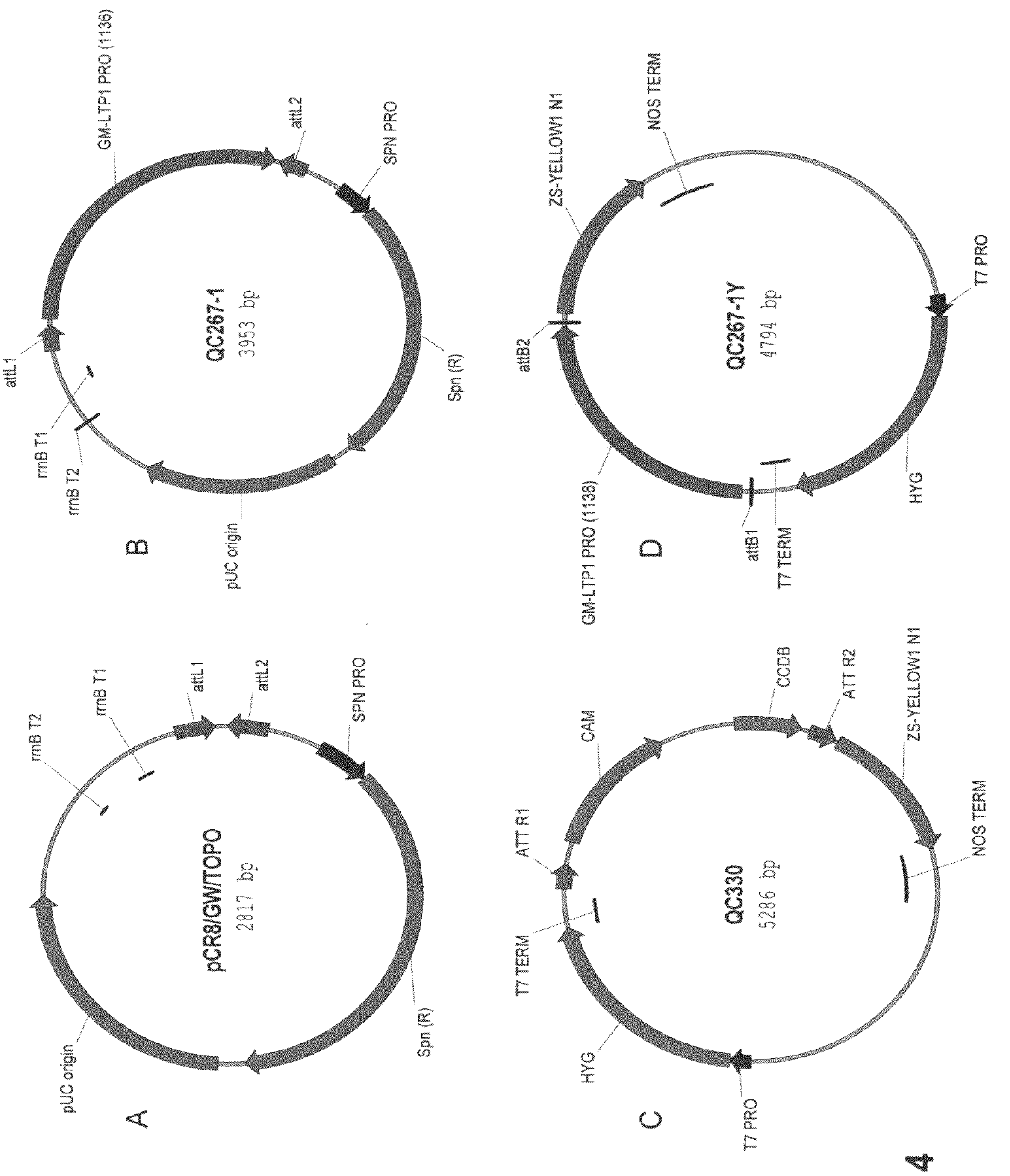

FIG. 4 displays a schematic representation of a Gateway cloning ready TA cloning vector pCR8/GW/TOPO (Invitrogen; FIG. 4A) and the vector created by cloning the full length LTP1 promoter into pCR8/GW/TOPO, QC267-1 (FIG. 4B). Also displayed is a schematic representation of a Gateway destination vector QC330 (FIG. 4C), containing a reporter ZS-YELLOW1 N1. The LTP1 promoter fragment is cloned into vector QC330 resulting in the displayed plasmid QC267-1Y (FIG. 4D) containing the full length 1136 bp LTP1 promoter, SEQ ID NO:1. Promoter deletion constructs QC267-2Y, QC267-3Y, QC267-4Y, and QC267-5Y containing the 927, 738, 527, 257 bp truncated LTP1 promoters, respectively, have similar map configurations, the difference being in the length of the promoter.

Figure 5:
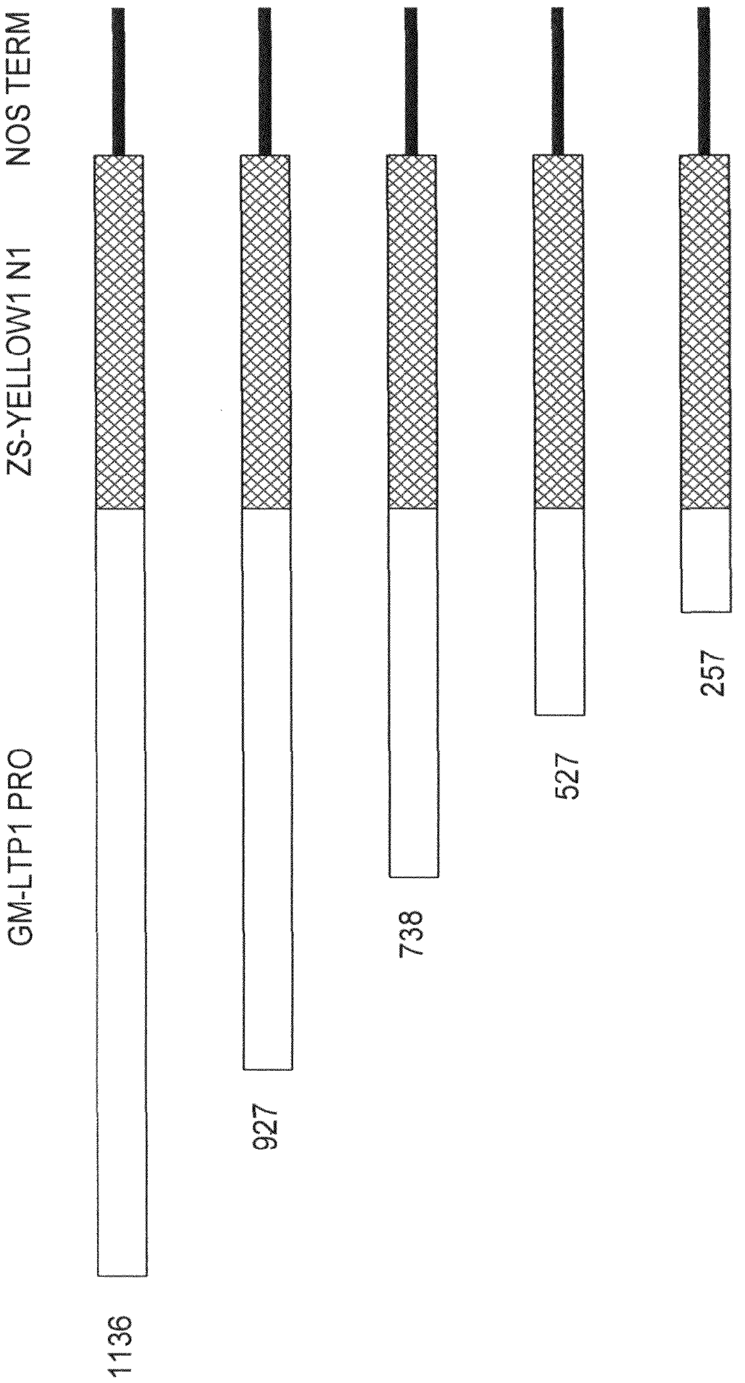

FIG. 5 is a linear schematic of the LTP1 promoter constructs QC267-1Y, QC267-2Y, QC267-3Y, QC267-4Y, and QC267-5Y. For QC267-1Y, the reporter ZS-YELLOW1 N1 is operably linked to the full-length LTP1 promoter. For the promoter constructs QC267-2Y, QC267-3Y, QC267-4Y, and QC267-5Y, the reporter ZS-YELLOW1 N1 is operably linked to each respective truncation of the LTP1 promoter.

Figure 6:
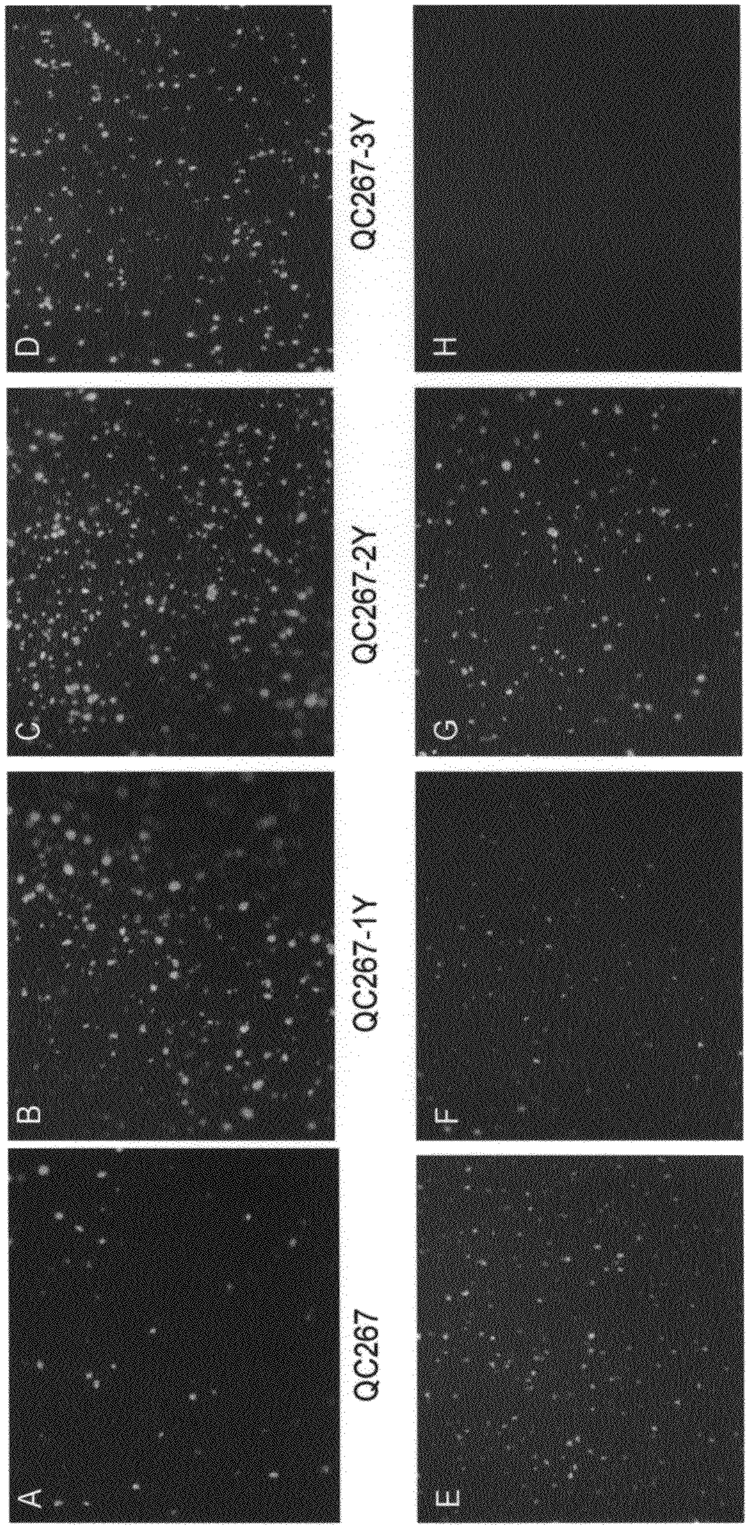

FIG. 6 displays the transient expression of the fluorescent protein reporter gene ZS-YELLOW1 N1 in the cotyledons of germinating soybean seeds. The reporter gene is driven by the LTP1 promoter in the stable transformation construct QC267, or driven by the LTP1 promoter or the progressively truncated LTP1 promoters in the transient expression constructs QC267-1Y to QC267-5Y. Additionally, displayed are the results of QC299i, which represents the negative control (no promoter present) and pZSL90, which represents the positive control (constitutive promoter SCP1 drives the reporter gene).

Figure 7:
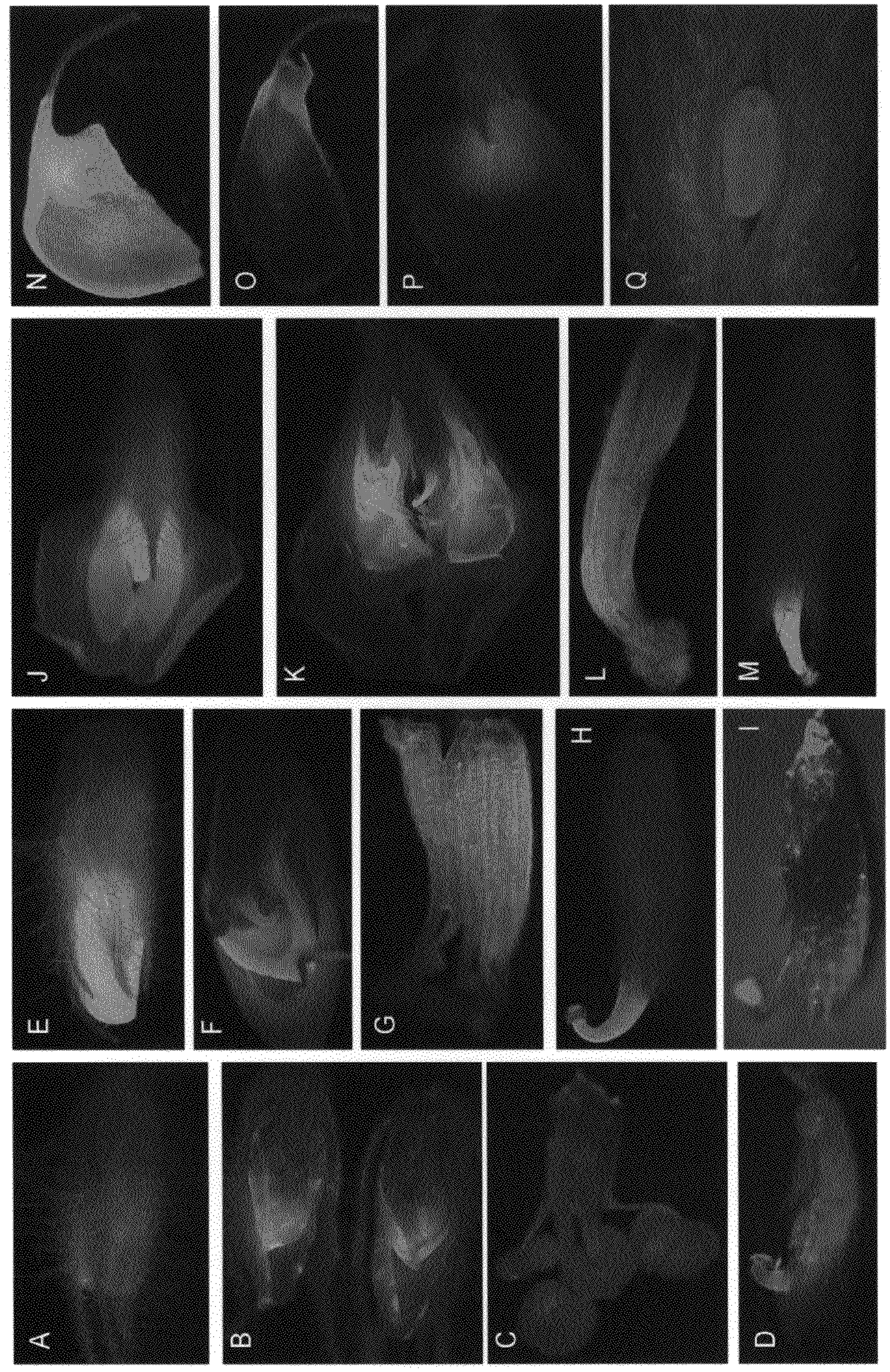

FIG. 7 displays the stable expression of the fluorescent protein reporter gene ZS-YELLOW1 N1 in the floral tissues of transgenic soybean plants containing a single copy of the transgene construct QC267.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

The term "promoter" refers to a nucleotide sequence capable of controlling the expression of a coding sequence or functional RNA. Functional RNA includes, but is not limited to, transfer RNA (tRNA) and ribosomal RNA (rRNA). Numerous examples of promoters may be found in the compilation by Okamuro and Goldberg (Biochemistry of Plants 15:1-82 (1989)). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that, since in most cases the exact boundaries of regulatory sequences have not been completely defined, DNA fragments of some variation may have identical promoter activity.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

A "flower" is a complex structure consisting of pedicel, sepal, petal, stamen, and carpel. A stamen comprises an anther, pollen and filament. A carpel comprises a stigma, style and ovary. An ovary comprises an ovule, embryo sac, and egg cell. Soybean pods develop from the pistil. It is likely that a gene expressed in the pistil of a flower continues to express in early pod. A "flower cell" is a cell from any one of these structures. Flower promoters in general include promoters that direct gene expression in any of the above tissues or cell types.

The term "flower crop" or "flowering plants" are plants that produce flowers that are marketable within the floriculture industry. Flower crops include both cut flowers and potted flowering plants. Cut flowers are plants that generate flowers that can be cut from the plant and can be used in fresh flower arrangements. Flower crops include roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

The terms "flower-specific promoter" or "flower-preferred promoter" may be used interchangeably herein and refer to promoters active in flower, with promoter activity being significantly higher in flower tissue versus non-flower tissue. "Preferentially initiates transcription" when describing a particular cell type, refers to the relative level of transcription in that particular cell type as opposed to other cell types. The described LTP1 promoters are promoters that preferentially initiate transcription in flower cells. Preferably, the promoter activity in terms of expression levels of an operably linked sequence are more than ten-fold higher in flower tissue than in non-flower tissue. More preferably, the promoter activity is present in flower tissue while undetectable in non-flower tissue.

As used herein, an "LTP1 promoter" refers to one type of flower-specific promoter. The native LTP1 promoter (or full-length native LTP1 promoter) is the native promoter of the putative soybean LTP1 polypeptide, which is a protein with significant homology to lipid transfer proteins from different plant species. The "LTP1 promoter", as used herein, also refers to fragments of the full-length native promoter that retain significant promoter activity. For example, an LTP1 promoter of the present invention can be the full-length promoter (SEQ ID NO:1) or a promoter-functioning fragment thereof, which includes, among others, the polynucleotides of SEQ ID NOs: 2, 3, 4 and 5. An LTP1 promoter also includes variants that are substantially similar and functionally equivalent to any portion of the nucleotide sequence set forth in SEQ ID NOs: 1, 2, 3, 4, or 5, or sequences there between.

An "isolated nucleic acid fragment" or "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" or "heterologous nucleotide sequence" refers to a nucleotide sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "fragment (or variant) that is functionally equivalent" and "functionally equivalent fragment (or variant)" are used interchangeably herein. These terms refer to a portion or subsequence or variant of the promoter sequence of the present invention in which the ability to initiate transcription or drive gene expression (such as to produce a certain phenotype) is retained. Fragments and variants can be obtained via methods such as site-directed mutagenesis and synthetic construction. As with the provided promoter sequences described herein, the contemplated fragments and variants operate to promote the flower-preferred expression of an operably linked heterologous nucleic acid sequence, forming a recombinant DNA construct (also, a chimeric gene). For example, the fragment or variant can be used in the design of recombinant DNA constructs to produce the desired phenotype in a transformed plant. Recombinant DNA constructs can be designed for use in co-suppression or antisense by linking a promoter fragment or variant thereof in the appropriate orientation relative to a heterologous nucleotide sequence.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides of SEQ ID NO:1, SEQ ID NO:2, SEQ ID NO:3, SEQ ID NO:4, or SEQ ID NO:5. In another aspect, a promoter fragment is the nucleotide sequence set forth in SEQ ID NO:2, SEQ ID NO:3, SEQ ID NO:4, or SEQ ID NO:5. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "substantially similar" and "corresponding substantially" as used herein refer to nucleic acid sequences, particularly promoter sequences, wherein changes in one or more nucleotide bases do not substantially alter the ability of the promoter to initiate transcription or drive gene expression or produce a certain phenotype. These terms also refer to modifications, including deletions and variants, of the nucleic acid sequences of the instant invention by way of deletion or insertion of one or more nucleotides that do not substantially alter the functional properties of the resulting promoter relative to the initial, unmodified promoter. It is therefore understood, as those skilled in the art will appreciate, that the invention encompasses more than the specific exemplary sequences.

In one example of "substantially similar", substantially similar nucleic acid sequences include those that are also defined by their ability to hybridize to the disclosed nucleic acid sequences, or portions thereof. Substantially similar nucleic acid sequences include those sequences that hybridize, under moderately stringent conditions (for example, 0.5× SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS is increased to 60° C. Another set of highly stringent conditions uses two final washes in 0.1×SSC, 0.1% SDS at 65° C.

In some examples, substantially similar nucleic acid sequences are those sequences that are 80% identical to the nucleic acid sequences reported herein or which are 80% identical to any portion of the nucleotide sequences reported herein. In some instances, nucleic acid sequences are those that are 90% identical to the nucleic acid sequences reported herein, or 90% identical to any portion of the nucleotide sequences reported herein. In some examples, nucleic acid sequences are those that are 95% identical to the nucleic acid sequences reported herein, or are 95% identical to any portion of the nucleotide sequences reported herein. It is well understood by one skilled in the art that many levels of sequence identity are useful in identifying related polynucleotide sequences. Useful examples of percent identities are those listed above, or also any integer percentage from 80% to 100%, such as, for example, 81%, 82%, 83%, 84%, 85%, 86%, 87%, 88%, 89%, 90%, 91%, 92%, 93%, 94%, 95%, 96%, 97%, 98% and 99%.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid sequence for improved expression in a host cell, it is desirable to design the nucleic acid sequence such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)).

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, and arranged in a manner different than that found in nature. "Endogenous gene" refers to a native gene in its natural location in the genome of an organism. A "foreign" gene refers to a gene not normally found in the host organism, that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, and are not limited to, promoters, enhancers, translation leader sequences, introns, and polyadenylation recognition sequences.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized as affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript, or it may be a RNA sequence derived from post transcriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcript accumulation of a target gene. The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated yet has an effect on cellular processes.

The term "operably linked" refers to the association of nucleic acid sequences on a single polynucleotide so that the function of one is affected by the other. For example, a promoter is operably linked with a heterologous nucleotide sequence, e.g., a coding sequence, when it is capable of affecting the expression of that heterologous nucleotide sequence (i.e., for example, the coding sequence is under the transcriptional control of the promoter). A coding sequence can be operably linked to promoter sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product, e.g., an mRNA or a protein (precursor or mature).

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication Nos. WO99/53050 and WO02/00904). This increases the frequency of co-suppression in the recovered transgenic plants. Another variation describes the use of plant viral sequences to direct the suppression, or "silencing", of proximal mRNA encoding sequences (PCT Publication No. WO98/36083). Neither of these co-suppressing phenomena has been elucidated mechanistically at the molecular level, although genetic evidence has been obtained that may lead to the identification of potential components (Elmayan et al., Plant Cell 10:1747-1757 (1998)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. Thus, a "transgenic plant cell" as used herein refers to a plant cell containing the transformed nucleic acid fragments. The preferred method of soybean cell transformation is the use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed material of the host organism is subsequently discarded after the transient gene expression assay.

A "marketable flower trait" is a characteristic or phenotype of the flower of a plant such as the color, scent or morphology of a flower. The marketable flower trait is a characteristic of a flower that is of high regard to a flower crop consumer in deciding whether to purchase the flower crop.

The phrase "genes involved in anthocyanin biosynthesis" refers to genes that encode proteins that play a role in converting metabolic precursors into the one of a number of anthocyanins. Examples of genes involved in the biosynthesis of anthocyanin are dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase (see, e.g., Mori et al., Plant Cell Reports 22:415-421 (2004)).

The phrase "genes involved in the biosynthesis of fragrant fatty acid derivatives" refers to genes that encode proteins that play a role in manipulating the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Examples of such genes include S-linalool synthase, acetyl CoA:benzylalcohol acetyltransferase, benzyl CoA:benzylalcohol benzoyl transferase, S-adenosyl-L-methionine:benzoic acid carboxyl methyl transferase (BAMT), mycrene synthases, (E)-β-ocimene synthase, orcinol O-methyltransferase, and limonene synthases (see, e.g., Tanaka et al., supra).

The term "flower homeotic genes" or "flower morphology modifying genes" refers to genes that are involved in pathways associated with flower morphology. A modification of flower morphology can lead to a novel form of the respective flower that can enhance its value in the flower crop marketplace. Morphology can include the size, shape, or petal pattern of a flower. Examples of flower homeotic genes include genes involved in cell-fate determination (in ABC combinatorial model of gene expression), including AGAMOUS, which determines carpel fate in the central whorl, APETALA3, which determines the sepal fate in the outer whorl, and PISTILLATA, which determines petal development in the second whorl (Espinosa-Soto et al., *Plant Cell* 16:2923-2939 (2004)).

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

Embodiments of the present invention include isolated polynucleotides comprising a nucleotide sequence that is a promoter. In some instances the nucleotide sequence includes one or more of the following:

a) the sequence set forth in SEQ ID NO:1 or a full-length complement thereof;

b) a nucleotide sequence comprising a fragment of SEQ ID NO:1, SEQ ID NO:2, SEQ ID NO:3, SEQ ID NO:4, or SEQ ID NO:5; or c) a nucleotide sequence comprising a sequence having at least 90% sequence identity, based on the BLASTN method of alignment, when compared to the sequence set forth in SEQ ID NO:1.

The nucleotide sequences of the present invention can be referred to as a promoter or as having promoter-like activity. In some embodiments the nucleotide sequence is a promoter that preferentially initiates transcription in a plant flower cell. Such promoter is referred to as a flower-specific promoter. Preferably the promoter of the present invention is the soybean "LTP1" promoter.

In a preferred embodiment, the promoter comprises the nucleotide sequence set forth in SEQ ID NO:1, SEQ ID NO:2, SEQ ID NO:3, SEQ ID NO:4, or SEQ ID NO:5. The present invention also includes nucleic acid fragments, variants, and complements of the aforementioned nucleotide sequences or promoters, provided that they are substantially similar and functionally equivalent to the nucleotide sequence set forth in these nucleotide sequences. A nucleic acid fragment or variant that is functionally equivalent to the present LTP1 promoter is any nucleic acid fragment or variant that is capable of initiating the expression, preferably initiating flower-specific expression, of a coding sequence or functional RNA in a similar manner to the LTP1 promoter. The expression patterns of LTP1 gene and its promoter are set forth in Examples 1, 7, and 8. In one example, the expression pattern of a LTP1 promoter fragment or variant will have expression patterns similar to that of the LTP1 promoter.

In some aspects, a recombinant DNA construct can be formed in part by operably linking at least one of the promoters of the present invention to any heterologous nucleotide sequence. The heterologous nucleotide sequence can be expressed in a cell as either a functional RNA or a polypeptide. The cell for expression includes a plant or bacterial cell, preferably a plant cell. The recombinant DNA construct preferably includes the LTP1 promoter. The recombinant DNA construct preferably includes a heterologous nucleotide sequence that encodes a protein that plays a role in flower color formation, fragrance production, or shape/morphology development of the flower. The color of a flower can be altered transgenically by expressing genes involved in betalain, carotenoid, or flavanoid biosynthesis. In regard to genes involved in the biosynthesis of anthocyanin, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase are some examples. The scent of a flower can be altered transgenically by expressing genes that manipulate the biosynthesis of fragrant fatty acid derivatives such as terpenoids, phenylpropanoids, and benzenoids in flowers. Some embodiments of the invention include a heterologous nucleotide sequence that is selected from S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthases, (E)-β-ocimene synthase, orcinol O-methyltransferase, or limonene synthases. Flower structures/morphologies can be altered transgenically by expressing flower homeotic genes to create novel ornamental varieties. Some embodiments of the invention include a heterologous nucleotide sequence that is selected from genes such as, for example, AGAMOUS, APETALA3, and PISTILLATA.

It is recognized that the instant promoters may be used with their native coding sequences to increase or decrease expression in flower tissue. The selection of the heterologous nucleic acid fragment depends upon the desired application or phenotype to be achieved. The various nucleic acid sequences can be manipulated so as to provide for the nucleic acid sequences in the proper orientation.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the recombinant DNA construct.

The described polynucleotide embodiments encompass isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. An "isolated" nucleic acid is essentially free of sequences (preferably protein encoding sequences) that naturally flank the polynucleotide (i.e., sequences located at the 5' and 3' ends of the nucleic acid) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide is derived.

In another embodiment, the present invention includes host cells comprising either the recombinant DNA constructs or isolated polynucleotides of the present invention. Examples of the host cells of the present invention include, and are not limited to, yeast, bacteria, and plants, including flower crops such as, e.g., rose, carnation, *Gerbera, Chrysanthemum*, tulip, Gladioli, *Alstroemeria, Anthurium, lisianthus*, larkspur, irises, orchid, snapdragon, African violet, or *azalea*. Preferably, the host cells are plant cells, and more preferably, flower crop cells, and more preferably, Gerbera, rose, carnation, *Chrysanthemum*, or tulip cells.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996); McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection (Neuhaus et al., Physiol. Plant. 79:213-217 (1990)), or particle bombardment (McCabe et al., Biotechnology 6:923 (1988); Christou et al., Plant Physiol. 87:671-674 (1988)).

In another embodiment, the present invention includes transgenic plants comprising the recombinant DNA constructs provided herein. The transgenic plants are selected from, for example, one of a number of various flower crops including roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

In some embodiments of the invention, there are provided transgenic seeds produced by the transgenic plants provided. Such seeds are able to produce another generation of transgenic plants.

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells and culturing of those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, there are generally available standard resource materials that describe specific conditions and procedures for the construction, manipulation and isolation of macromolecules (e.g., DNA molecules, plasmids, and the like), generation of recombinant DNA fragments and recombinant expression constructs, and the screening and isolating of clones (see, for example, Sambrook et al., 1989; Maliga et al., In Methods in Plant Molecular Biology; Cold Spring Harbor Press, 1995; Birren et al., In Genome Analysis: Detecting Genes, 1; Cold Spring Harbor New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the LTP1 promoter in flowers is in some cases comparable to that of many known strong promoters such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis oleosin* promoters (Plant et al., Plant Mol. Biol. 25:193-205 (1994); Li, Texas A&M University Ph.D. dissertation, pp. 107-128 (1997)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter (Raschke et al., J. Mol. Biol. 199(4):549-557 (1988)), and a maize H3 histone gene promoter (Atanassova et al., Plant Mol. Biol. 37:275-285 (1998)).

In some embodiments, the promoters of the present invention are useful when flower-specific expression of a target heterologous nucleic acid fragment is required. In addition, while the promoters of the present invention are most active in developing flower buds and open flowers (See FIG. 1), they still have activity in developing seeds, although the activity is approximately ten times less. Thus, the promoters can be used for gene expression or gene silencing in flowers, especially when gene expression or gene silencing is desired predominantly in flowers along with a lower degree in developing seeds.

In some embodiments, the promoters of the present invention are to construct recombinant DNA constructs that can be used to reduce expression of at least one heterologous nucleic acid sequence in a plant cell. To accomplish this, a recombinant DNA construct can be constructed by linking the heterologous nucleic acid sequence to a promoter of the present invention. (See U.S. Pat. No. 5,231,020 and PCT Publication Nos. WO99/53050, WO02/00904, and WO98/36083 for methodology to block plant gene expression via cosuppression.) Alternatively, recombinant DNA constructs designed to express antisense RNA for a heterologous nucleic acid fragment can be constructed by linking the fragment in reverse orientation to a promoter of the present invention. (See U.S. Pat. No. 5,107,065 for methodology to block plant gene expression via antisense RNA.) Either the cosuppression or antisense chimeric gene can be introduced into plants via transformation. Transformants, wherein expression of the heterologous nucleic acid sequence is decreased or eliminated, are then selected.

There are embodiments of the present invention that include promoters of the present invention being utilized for methods of altering (increasing or decreasing) the expression of at least one heterologous nucleic acid sequence in a plant cell which comprises: transforming a plant cell with a recombinant DNA expression construct described herein; growing fertile mature plants from the transformed plant cell; and selecting plants containing a transformed plant cell wherein the expression of the heterologous nucleotide sequence is altered (increased or decreased).

Transformation and selection can be accomplished using methods well-known to those skilled in the art including, but not limited to, the methods described herein.

There are provided some embodiments that include methods of expressing a coding sequence in a plant that is a flower crop comprising: introducing a recombinant DNA construct disclosed herein into the plant; growing the plant; and selecting a plant displaying expression of the coding sequence; wherein the nucleotide sequence comprises: a nucleotide sequence comprising the sequence set forth in SEQ ID NO:1 or a full-length complement thereof; a nucleotide sequence comprising a fragment of the sequence set forth in SEQ ID NO:1, SEQ ID NO:2, SEQ ID NO:3, SEQ ID NO:4, or SEQ ID NO:5, or in alternative embodiments, the sequence set forth in SEQ ID NO:2, SEQ ID NO:3, SEQ ID NO:4, or SEQ ID NO:5; or a nucleotide sequence comprising a sequence having at least 90% sequence identity, based on the BLASTN method of alignment, when compared to the sequence set forth in SEQ ID NO:1; wherein said nucleotide sequence initiates transcription in a flower cell of the plant.

Furthermore, some embodiments of the present invention include methods of transgenically altering a marketable flower trait of a flowering plant, comprising: introducing a recombinant DNA construct disclosed herein into the flowering plant; growing a fertile, mature flowering plant resulting from the introducing step; and selecting a flowering plant expressing the heterologous nucleotide sequence in flower tissue based on the altered marketable flower trait.

As further described in the Examples below, the promoter activity of the soybean genomic DNA fragment upstream of the LTP1 protein coding sequence SEQ ID NO:1 was assessed by linking the fragment to a yellow fluorescence reporter gene, ZS-YELLOW1 N1 (YFP) (Matz et al., Nat. Biotechnol. 17:969-973 (1999)), transforming the promoter::YFP expression cassette into soybean, and analyzing YFP expression in various cell types of the transgenic plants (see Example 7 and 8). All parts of the transgenic plants were analyzed and YFP expression was predominantly detected in flowers. These results indicated that the nucleic acid fragment contained flower-preferred promoter.

Some embodiments of the present invention provide recombinant DNA constructs comprising at least one isopentenyl transferase nucleic acid sequence operably linked to a provide promoter, preferably a LTP1 promoter. The isopentenyl transferase plays a key step in the biosynthesis of plant cytokinin (Kakimoto, J. Plant Res. 116:233-239 (2003)). Elevated levels of cytokinin in plant cells might help to delay floral senescence and abortion which may present a potential way to improve crop yields (Chang et al., Plant Physiol. 132:2174-2183 (2003); Young et al., Plant J. 38:910-922 (2004)).

Utilities for Flower-Specific Promoters

The color, scent or morphology of a flower represents marketable flower traits, or characteristics/phenotypes of a flower that consumers, particularly floriculturalists, consider when determining which flowers are desirable and will be purchased. Hence, it would be beneficial to be able to alter these characteristics in order to satisfy the desires of consumers. Transgenic technologies can be implemented in order to achieve such results.

The phenotype of a flower can be altered transgenically by expressing genes, preferably in flower tissue, that play a role in color formation, fragrance production, or shape/morphology development of the flower. This type of alteration is particularly useful in the floriculture industry, and particularly useful for flowering plants.

The color of a flower is mainly the result of three types of pigment, flavanoids, carotenoids, and betalains. The flavanoids are the most common of the three and they contribute to colors ranging from yellow to red to blue, with anthocyanins being the major flavanoid. Carotenoids are C-40 tetraterpenoids that contribute to the majority of yellow hues and contribute to orange/red, bronze and brown colors, e.g., that seen in roses and chrysanthemums. Betalains are the least abundant and contribute to various hues of ivory, yellow, orange, red and violet. The color of a flower can be altered transgenically by expressing genes involved in, e.g., betalain, carotenoid, or flavanoid biosynthesis. In one example, the color of a flower can be altered transgenically by expressing genes involved in the biosynthesis of anthocyanin, for example, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase. In some aspects of the invention, the gene involved in anthocyanin biosynthesis is the flavonoid 3,5-hydroxylase gene (see, e.g., Mori et al., Plant Cell Reports 22:415-421 (2004)). This type of alteration is particularly useful in the floriculture industry, providing novel flower colors in flower crops.

In addition to color, the scent of a flower can be altered transgenically by expressing genes that manipulate the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Genes involved in the biosynthesis of fragrant fatty acid derivatives can be operably linked to the flower-specific promoters presently described for preferential expression in flower tissue. The preferential expression in flower tissue can be utilized to generate new and desirable fragrances to enhance the demand for the underlying cut flower. A number of known genes that are involved in the biosynthesis of floral scents are described below. A strong sweet scent can be generated in a flower by introducing or upregulating expression of S-linalool synthase, which was earlier isolated from *Clarkia breweri*. Two genes that are responsible for the production of benzylacetate and benzylbenzoate are acetyl CoA:benzylalcohol acetyltransferase and benzyl CoA:benzylalcohol benzoyl transferase, respectively. These transferases were also reported to have been isolated from *C. breweri*. A phenylpropanoid floral scent, methylbenzoate, is synthesized in part by S-adenosyl-L-methionine:benzoic acid carboxyl methyl transferase (BAMT), which catalyzes the final step in the biosynthesis of methyl benzoate. BAMT is known to have a significant role in the emission of methyl benzoate in snapdragon flowers. Two monoterpenes, mycrene and (E)-β-ocimene, from snapdragon are known to be synthesized in part by the terpene synthases: mycrene synthases and (E)-β-ocimene synthases. Other genes involved in biosynthesis of floral scents have been reported and are being newly discovered, many of which are isolated from rose. Some genes involved in scent production in the rose include orcinol O-methyltransferase, for synthesis of S-adenosylmethionine, and limonene synthases (see, e.g., Tanaka et al., supra).

Flower structures/morphologies can be altered transgenically by expressing flower homeotic genes to create novel ornamental varieties. The flower homeotic genes that are determinative of flower morphology include genes such as AGAMOUS, APETALA3, PISTILLATA, and others that are known and/or are being elucidated (see, e.g., Espinosa-Soto et al., Plant Cell 16:2923-2939 (2004)).

EXAMPLES

Aspects of the present invention are exemplified in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the discussion below, parts and percentages are by weight and degrees are Celsius, unless otherwise stated. Sequences of promoters, cDNA, adaptors, and primers listed herein are in the 5' to 3' orientation unless described otherwise. Techniques in molecular biology were typically performed as described in Ausubel et al., 1990 or Sambrook et al., 1989.

Example 1

Lynx MPSS Profiling of Soybean Genes Preferably Expressed in Flowers

Soybean expression sequence tags (ESTs) were generated by sequencing randomly selected clones from cDNA libraries constructed from different soybean tissues. Multiple EST sequences may have different lengths representing different regions of the same soybean gene. For those EST sequences representing the same gene that are found more frequently in a flower-specific cDNA library, there is a possibility that the representative gene could be a flower preferred gene candidate. Multiple EST sequences representing the same soybean gene were compiled electronically based on their overlapping sequence homology into a full length sequence representing a unique gene. These assembled, unique gene sequences were cumulatively collected and the information was stored in a searchable database. Flower specific candidate genes were identified by searching this database to find gene sequences that are frequently found in flower libraries but are rarely found in other tissue libraries, or not found in other tissue libraries.

One unique gene, PSO330124, was identified in the search as a flower specific gene candidate since all of the ESTs representing PSO330124 were found only in flower tissue. The PSO330124 cDNA sequence (SEQ ID NO:16) and its putative translated protein sequence (SEQ ID NO:36) were used to search National Center for Biotechnology Information (NCBI) databases. PSO330124 was found to be a novel soybean gene having high homology to several lipid transfer protein genes of other species. PSO330124 was subsequently named as GM-LTP1, Glycine max lipid transfer protein 1.

A more sensitive gene expression profiling methodology MPSS (Mass Parallel Signature Sequence) transcript profiling technique (Brenner et al., Proc Natl Acad Sci USA 97:1665-70 (2000)) was used to confirm PSO330124 as a flower specific gene. The MPSS technology involves the generation of 17 base signature tags from mRNA samples that have been reverse transcribed from poly A+ RNA isolated using standard molecular biology techniques (Sambrook et al., 1989). The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS platform can be used to determine the expression pattern of a particular gene and its expression levels in different tissues.

MPSS gene expression profiles were generated from different soybean tissues over time, and the profiles were accumulated in a searchable database. PSO330124 cDNA sequence was used to search the MPSS database to identify a MPSS tag that was identical to a 17 base pair region in the 3' end of the PSO330124 cDNA sequence: GATCCCACTAGGGAGTA (SEQ ID NO:24). The identified MPSS tag was then used to search the MPSS database to reveal its abundance in different tissues. As illustrated in Table 1, the PSO330124 gene was confirmed to be highly abundant in flowers and pods, a desired expression profile for its promoter to be able to express genes in flowers and in early developing pods.

TABLE 1

Lynx MPSS Expression Profiles of the PSO330124 Gene

| TAG_NAME | TAG_SEQ | Anther | Flower | Leaf | Pod | Root | Seed | Stem |
|---|---|---|---|---|---|---|---|---|
| PSO330124 | GATCCCACTAGGGAGTA | 0 | 4319 | 2 | 2619 | 0 | 613 | 4 |

Example 2

Quantitative RT-PCR Profiles of LTP1 Gene Expression in Soybean

The MPSS profile of the LTP1 gene, PSO330124, was confirmed and extended by analyzing 14 different soybean tissues using the relative quantitative RT-PCR (qRT-PCR) technique with a 7500 real time PCR system (Applied Biosystems, Foster City, Calif.).

Fourteen soybean tissues (somatic embryo, somatic embryo grown one week on charcoal plate, leaf, leaf petiole, root, flower bud, open flower, R3 pod, R4 seed, R4 pod coat, R5 seed, R5 pod coat, R6 seed, R6 pod coat) were collected from cultivar 'Jack' and flash frozen in liquid nitrogen. The seed and pod development stages were defined according to descriptions in Fehr and Caviness, IWSRBC 80:1-12 (1977). Total RNA was extracted with Trizol reagents (Invitrogen, Carlsbad, Calif.) and treated with DNase I to remove any trace amount of genomic DNA contamination. The first strand cDNA was synthesized with Superscript III reverse transcriptase (Invitrogen).

PCR analysis was performed to confirm that the cDNA was free of genomic DNA. The PCR analysis used the following primers:

```
SEQ ID NO: 19    GACCAAGACACACTCGTTCATATATC

SEQ ID NO: 20    TCTGCTGCTCAATGTTTACAAGGAC
```

The primers are specific to the 5'UTR intron/exon junction region of a soybean S-adenosylmethionine synthetase gene promoter (WO00/37662). PCR using this primer set amplifies a 967 bp DNA fragment from any soybean genomic DNA template and a 376 bp DNA fragment from the cDNA template. The cDNA aliquots were used in qRT-PCR analysis in which an endogenous soybean ATP sulfurylase gene was used as an internal control and wild type soybean genomic DNA was used as the calibrator for relative quantification.

The qRT-PCR profiling of the LTP1 gene expression confirmed its predominant flower expression and also showed ongoing expression at levels approximately ten fold lower during early pod and seed development (see FIG. 1).

Example 3

Isolation of Soybean LTP1 Promoter

The soybean genomic DNA fragment corresponding to the LTP1 promoter was isolated using a polymerase chain reaction (PCR) based approach called genome walking using the Universal GenomeWalker™ kit from Clontech™ (Product User Manual No. PT3042-1).

Soybean genomic DNA was digested to completion with DraI, a DNA restriction enzyme that generates DNA fragments having blunt ends according to standard protocols. This process was repeated three times, separately, using either EcoRV, HpaI, and PmlI, each of which generates DNA fragments having blunt ends.

Double strand adaptors supplied in the GenomeWalker™ kit were added to the blunt ends of the genomic DNA fragments by DNA ligase. Two rounds of PCR were performed to amplify the LTP1 corresponding genomic DNA fragment using two nested primers supplied in the Universal GenomeWalker™ kit that are specific for the adaptor sequence (AP1 and AP2, for the first and second adaptor primer, respectively), and two LTP1 gene specific primers (GSP1 and GSP2) designed based on the LTP1 5' coding sequence PSO330124. The oligonucleotide sequences of the four primers are shown below:

```
SEQ ID NO: 12 (GSP1) CTTCATGACAAGCAGTGAGCTAGCC

SEQ ID NO: 13 (AP1)  GTAATACGACTCACTATAGGGCACG

SEQ ID NO: 14 (GSP2) CCATGGATTTGGAAGAGTTAGAGGATGAAAT
                     TG

SEQ ID NO: 15 (AP2)  CTATAGGGCACGCGTGGTCGAC
```

The underlined bases in GSP2 primer are the recognition site for the restriction enzyme NcoI. The AP2 primer from the Universal GenomeWalker™ kit contains a Sa/I restriction site, also underlined. The 3' end of the adaptor sequence GTAATACGACTCACTAT-AGGGCACGCGTGGTCGACGGCCCGGGCTGGT (SEQ ID NO:21) also contains a XmaI recognition site downstream to the corresponding Sa/I restriction site in AP2 primer.

The AP1 and the GSP1 primers were used in the first round PCR using each of the adaptor ligated genomic DNA populations (DraI, EcoRV, HpaI or Pm/I) under conditions defined in the GenomeWalker™ protocol. Cycle conditions were 94° C. for 4 minutes; 35 cycles of 94° C. for 30 seconds, 60° C. for 1 minute, and 68° C. for 3 minutes; and a final 68° C. for 5 minutes before holding at 4° C. One microliter from each of the first round PCR products was used as templates for the second round PCR with the AP2 and GSP2 primers. Cycle conditions for second round PCR were 94° C. for 4 minutes; 25 cycles of 94° C. for 30 seconds, 60° C. for 1 minute, and 68° C. for 3 minutes; and a final 68° C. for 5 minutes before holding at 4° C. Agarose gels were run to identify specific PCR product with an optimal fragment length. An approximately 1.2 Kb PCR product was detected and subsequently cloned into pCR2.1-TOPO vector by TOPO TA cloning (Invitrogen). Sequencing of the cloned PCR products revealed that its 3' end matched the 96 bp 5' end of the LTP1 cDNA sequence, indicating that the PCR product was indeed the corresponding LTP1 genomic DNA fragment. The 1136 bp sequence upstream of the putative LTP1 start codon ATG is herein designated as soybean LTP1 promoter (SEQ ID NO:1).

Example 4

LTP1 Promoter Copy Number Analysis

Southern hybridization analysis was performed to determine whether there were other sequences in the soybean genome with high similarity to the LTP1 promoter. Soybean 'Jack' wild type genomic DNA was digested with nine different restriction enzymes (BamHI, Bg/II, DraI, EcoRI, EcoRV, HindIII, MfeI, NdeI, and SpeI), each separately, and distributed in a 0.7% agarose gel by electrophoresis. Each of the digested DNA samples was blotted onto a Nylon membrane and hybridized with digoxigenin (DIG) labeled LTP1 promoter DNA probe according to the standard protocol (Roche Applied Science, Indianapolis, Ind.). The LTP1 promoter probe was labeled by PCR using the DIG DNA labeling kit (Roche Applied Science) with two gene specific primers to make a 1154 bp probe covering the entire 1136 bp LTP1 promoter sequence. The two gene specific primers used were:

```
SEQ ID NO: 22   ATAATCCCGGGTCCTACTCCTACTCGACAA

SEQ ID NO: 23   GAGCTACCCGGGATTTGGAAGAGTTAGAGGATG
```

Both primers contain an XmaI restriction site CCCGGG, introducing extra base pairs in the LTP1 probe as subsequent cloning sites. These extra base pairs should not affect Southern hybridization results.

A single band was detected in each of five digestions, BamHI, BglII, EcoRI, EcoRV, and NdeI, suggesting that the LTP1 promoter sequence exists in soybean genome as a single copy unique sequence (FIG. 2A). The fact that no band was detected on the Southern blot of the DraI digestion could be explained by presence of multiple DraI restriction sites in the promoter sequence (FIG. 2B), and another DraI restriction site in the LTP1 coding region resulting in DNA fragments too small to be kept on the blot (any band smaller than 1 Kb would run out of the agarose gel under the experiment conditions). Two bands, one strong and one weak, detected in the MfeI digestion could be due to the presence of an MfeI restriction site in the 3' end region of the LTP1 promoter. The weak band detected in HindIII digestion and the three faint bands detected in SpeI digestion that could be highlighted by over exposure suggested the likelihood of a sequence with low similarity to the LTP1 promoter sequence in soybean genome (FIG. 2A).

Example 5

LTP1:YFP Reporter Constructs and Soybean Transformation

Two oligonucleotide primers were designed to re-amplify the LTP1 promoter with a XmaI restriction site incorporated in each of the primer sequences (underlined in SEQ ID NO:22 and SEQ ID NO:23, respectively) as shown below:

```
SEQ ID NO: 22   ATAATCCCGGGTCCTACTCCTACTCGACAA

SEQ ID NO: 23   GAGCTACCCGGGATTTGGAAGAGTTAGAGGATG
```

The re-amplified LTP1 promoter fragment was digested with XmaI, gel purified and cloned into the XmaI site of a vector plasmid QC258 (SEQ ID NO:37; FIG. 3A) containing the soybean transformation selectable marker gene SAMS:ALS (S-adenosyl methionine synthetase:acetolactate synthase) and a promoter-less fluorescent reporter gene ZS-YELLOW1 N1 (YFP) to make the reporter construct QC267 (SEQ ID NO:17) with the soybean LTP1 promoter driving the YFP gene expression (FIG. 3B). The 6124 bp DNA fragment containing the linked LTP1:YFP and SAMS:ALS expression cassettes was cut out of QC267 plasmid by AscI digestion, separated from the vector backbone fragment by agarose gel electrophoresis, and purified from the gel using a DNA gel extraction kit (Qiagen, Valencia, Calif.). The purified DNA fragment was used to transform soybean cultivar Jack using the particle gun bombardment method (Klein et al., Nature 327:70-73 (1987); U.S. Pat. No. 4,945,050) to study the LTP1 promoter activity in stably transformed soybean plants.

Soybean somatic embryos from the Jack cultivar were induced as follows. Cotyledons (~3 mm in length) were dissected from surface-sterilized, immature seeds and were cultured for 6-10 weeks under fluorescent light at 26° C. on a Murashige and Skoog media ("MS media") containing 0.7% agar and supplemented with 10 mg/ml 2,4-dichlorophenoxyacetic acid (2,4-D). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (helium retrofit) (Bio-Rad Laboratories, Hercules, Calif.). To 50 μl of a 60 mg/ml 1.0 mm gold particle suspension were added (in order): 30 μl of 10 ng/μl LTP1:YFP+SAMS:ALS DNA fragment, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. 5 μl of the DNA-coated gold particles were then loaded on each macro carrier disk.

Approximately 300-400 mg of a two-week-old suspension culture was placed in an empty 60×15-mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar, solid MS media plates without 2,4-D supplement to allow somatic embryos to develop. A sample of each event was collected at this stage for PCR and quantitative PCR analysis.

Cotyledon stage somatic embryos were dried-down (by transferring them into an empty small Petri dish that was seated on top of a 10 cm Petri dish to allow slow dry down) to mimic the last stages of soybean seed development. Dried-down embryos were placed on germination solid media, and transgenic soybean plantlets were regenerated. The transgenic plants were then transferred to soil and maintained in growth chambers for seed production.

Genomic DNA was extracted from somatic embryo samples and analyzed by quantitative PCR using the 7500 real time PCR system (Applied Biosystems) with gene-specific primers and 6-carboxyfluorescein (FAM)-labeled fluorescence probes to check copy numbers of both the SAMS:ALS expression cassette and the LTP1:YFP expression cassette. The qPCR analysis was done in duplex reactions with a heat shock protein (HSP) gene as the endogenous control and a transgenic DNA sample with a known single copy of SAMS:ALS or YFP transgene as the calibrator using the relative quantification methodology. The endogenous control HSP probe was labeled with VIC (Applera Corporation, Norwalk, Conn.) and the target gene SAMS or YFP probe was labeled with FAM for the simultaneous detection of both fluorescent probes in the same duplex reactions. The primers and probes used in the qPCR analysis are listed in Table 2 below.

TABLE 2

Primers and Probes used in qPCR Analysis

| SEQ ID NO:Description | Sequence |
|---|---|
| 25SAMS forward primer | GGAAGAAGAGAATCGGGTGGTT |
| 26FAM labeled SAMS probe | ATTGTGTTGTGTGGCATGGTTAT |
| 27SAMS reverse primer | GGCTTGTTGTGCAGTTTTTGAAG |
| 28YFP forward primer | AACGGCCACAAGTTCGTGAT |
| 29FAM labeled YFP probe | ACCGGCGAGGGCATCGGCTA |
| 30YFP reverse primer | CTTCAAGGGCAAGCAGACCA |
| 31HSP forward primer | CAAACTTGACAAAGCCACAACTCT |
| 32VIC labeled HSP probe | CTCTCATCTCATATAAATAC |
| 33HSP reverse primer | GGAGAAATTGGTGTCGTGGAA |

FAM labeled DNA oligo probes and VIC labeled oligo probes were obtained from Sigma Genosys (The Woodlands, Tex.).

Only transgenic soybean events containing 1 or 2 copies of both the SAMS:ALS expression cassette and the LTP1:YFP expression cassette were selected for further gene expression evaluation and seed production (see Table 3). Events negative for YFP qPCR or with more than 2 copies for the SAMS qPCR were terminated. YFP expressions in flowers as described in EXAMPLE 8 are also recorded in the same table.

TABLE 3

Relative Transgene Copy Numbers and YFP Expression

| Event ID | SAMS qPCR | YFP qPCR | YFP Expression |
|---|---|---|---|
| 4708.1.1 | 1.07 | 3.00 | + |
| 4708.3.1 | 0.94 | 1.25 | + |
| 4708.3.2 | 1.01 | 1.16 | + |

TABLE 3-continued

Relative Transgene Copy Numbers and YFP Expression

| Event ID | SAMS qPCR | YFP qPCR | YFP Expression |
|---|---|---|---|
| 4708.3.3 | 1.13 | 1.01 | – |
| 4708.3.4 | 0.90 | 1.69 | + |
| 4708.4.1 | 1.22 | 1.23 | + |
| 4708.4.2 | 1.13 | 1.37 | – |
| 4708.5.1 | 3.28 | 1.33 | Terminated |
| 4708.5.2 | 1.27 | 0.00 | Terminated |
| 4708.5.3 | 1.74 | 2.06 | + |
| 4708.5.4 | 0.98 | 1.09 | + |
| 4708.5.5 | 2.98 | 2.26 | Terminated |
| 4708.6.1 | 1.47 | 1.24 | + |
| 4708.8.1 | 0.99 | 1.68 | + |
| 4708.8.2 | 1.13 | 0.00 | Terminated |
| 4708.8.3 | 1.02 | 1.06 | + |
| 4708.8.4 | 3.68 | 3.09 | Terminated |
| 4708.8.5 | 0.99 | 0.93 | – |

Example 6

Construction of LTP1 Promoter Deletion Constructs

To define the transcriptional elements controlling the LTP1 promoter activity, the 1136 bp full length and four 5' unidirectional deletion fragments (SEQ ID NO:1 of 1136 bp, SEQ ID NO:2 of 927 bp, SEQ ID NO:3 of 738 bp, SEQ ID NO:4 of 527 bp, SEQ ID NO:5 of 257 bp) were made by utilizing PCR amplification and the full length soybean LTP1 promoter contained in the original construct QC267 (FIG. 3B). The same antisense primer CAATTTCATCCTCTAACTCTTCCAAATCC (SEQ ID NO:6) was used in the amplification of all the five LTP1 promoter fragments by pairing with different sense primers SEQ ID NOs: 7, 8, 9, 10, 11, respectively, to produce the promoter fragments represented by SEQ ID NOs: 1, 2, 3, 4, 5.

Each of the PCR amplified promoter DNA fragments was cloned into the Gateway cloning ready TA cloning vector pCR8/GW/TOPO (Invitrogen; SEQ ID NO:38; FIG. 4A) and clones with the correct orientation, relative to the Gateway recombination sites attL1 and attL2 (Invitrogen, Carlsbad, Calif.), were selected by MfeI+XbaI double restriction enzyme digestion analysis or sequence confirmation (see FIG. 4B for the example map QC267-1 (SEQ ID NO:39)). The maps of constructs QC267-2 (SEQ ID NO:40), QC267-3 (SEQ ID NO:41), QC2674 (SEQ ID NO:42), and QC267-5 (SEQ ID NO:43) containing the LTP1 promoter fragments SEQ ID NOs: 2, 3, 4, 5 were similar. The promoter fragment in the right orientation was subsequently cloned into the Gateway destination vector QC330 (SEQ ID NO:48; FIG. 4C) by Gateway LR clonase reaction (Invitrogen) to place the promoter fragment in front of the reporter gene YFP (see the example map QC267-1Y in FIG. 4D (SEQ ID NO:18)). A 21 bp Gateway recombination site attB2 CAGCTTTCTTGTACAAAGTGG (SEQ ID NO:35) was inserted between the promoter and the YFP reporter gene coding region as a result of the Gateway cloning process. The maps of constructs QC267-2Y (SEQ ID NO:44), QC267-3Y (SEQ ID NO:45), QC267-4Y (SEQ ID NO:46), and QC267-5Y (SEQ ID NO:47) containing the LTP1 promoter fragments SEQ ID NOs: 2, 3, 4, 5 were similar.

The LTP1:YFP promoter deletion constructs were ready to be transformed into germinating soybean cotyledons by gene gun bombardment method for transient gene expression study. The 1136 bp full length LTP1 promoter was cloned similarly as a positive control for transient expression analysis. A simple schematic description of the five LTP1 promoter deletions can be found in FIG. 5.

Example 7

Transient Expression Analysis of LTP1:YFP Constructs

The full length LTP1 promoter and a series of deletion constructs QC267-1Y, 2Y, 3Y, 4Y, and 5Y were tested by transiently expressing the ZS-YELLOW1 N1 (YFP) reporter gene in germinating soybean cotyledons. Germinating soybean cotyledons were used as the target tissue for transient expression assays. Soybean seeds were rinsed with 10% Tween 20 in sterile water, surface-sterilized with 70% ethanol for 2 minutes and then by 6% sodium hypochloride for 15 minutes. After rinsing, the seeds were placed on wet filter paper in a Petri dish to germinate for 4-6 days under fluorescent light at 26° C. Green cotyledons were excised and placed inner side up on a 0.7% agar plate containing MS media for particle gun bombardment.

The DNA and gold particle mixtures were prepared similarly as described in EXAMPLE 5 except with more DNA (100 ng/μl). The bombardments were also carried out under similar parameters as described in EXAMPLE 5. YFP expression was checked under a Leica MZFLIII stereo microscope equipped with UV light source and appropriate light filters (Leica Microsystems Inc., Bannockburn, Ill.) and pictures were taken with the same settings. Pictures were taken approximately 24 hours after bombardment with 8× magnification and camera settings: 1.06 gamma, 0.0% gain, and 0.58 seconds exposure.

The stable transformation constructs QC267 containing the linked LTP1:YFP and SAMS:ALS expressed well in transient expression assay as shown by the large green dots (FIG. 6A). Each dot represented a single cotyledon cell which appeared larger if the fluorescence was strong or smaller if the fluorescence was weak, even under the same magnification. The QC267-1 Y construct containing the same full length 1136 bp LTP1 promoter with an attB2 Gateway recombination site (Invitrogen) inserted between the LTP1 promoter and YFP and without the SAMS:ALS cassette had seemingly stronger expression with some dots glowing yellow (FIG. 6B).

The four promoter deletion constructs QC267-2Y, 3Y, 4Y, 5Y had the same structure as QC267-1Y with shorter, truncated LTP1 promoter, as described in EXAMPLE 6. The 927 bp truncated LTP1 promoter construct QC267-2Y had the same expression level as the full length LTP1 promoter construct QC267-1Y (FIG. 6C). The 738 bp truncated LTP1 promoter construct QC267-3Y had lower YFP expression as indicated by the smaller fluorescence dots (FIG. 6D). Further truncation of the LTP1 promoter to 527 bp in construct QC267-4Y further reduced the promoter strength (FIG. 6E). When the LTP1 promoter was truncated to the 257 bp minimal size in construct QC267-5Y, the promoter still retained activity at a minimal level marginally detected by the transient assay (FIG. 6F). Construct pZSL90 (SEQ ID NO:49) with a constitutive promoter SCP1 to drive the YFP expression and construct QC299i (SEQ ID NO:50) without any promoter to drive the YFP expression were used in the transient assays as positive and negative controls, respectively (FIG. 6G, H). No fluorescence was detected in the negative control.

Example 8

LTP1:YFP Expression in Stable Transgenic Soybean Plants

YFP gene expression was checked at different stages of transgenic plant development for yellow fluorescence emission under a Leica MZFLIII stereo microscope equipped with UV light source and appropriate light filters (Leica Microsystems Inc., Bannockburn, Ill.). No specific yellow fluorescence was detected during somatic embryo development or in vegetative tissues such as leaf, petiole, stem, or root. Fluorescence was only detected in flowers.

A soybean flower consists of five sepals, five petals including one standard large upper petal, two large side petals, and two small fused lower petals called kneel to enclose ten stamens and one carpel. The carpel consists of a stigma, a style, and an ovary in which there are 2-4 ovules. Specific fluorescence signal (green color) was first detected in the distal part of petals in young flower bud when the petals were still mostly enclosed by sepals (FIG. 7A), and clearly in petals of flower bud (FIG. 7E) and of open flower (FIG. 7J). No fluorescence was detected in sepals or in flower pedicle. No expression was detected in very young flower bud when the petals were completely enclosed by sepals even when the bud was cut open to expose all the inner structures.

When a young flower bud in which petals were still mostly enclosed by sepals was dissected, fluorescence was only detected in petals, often as patches indicating the start of YFP expression (FIG. 7B). No fluorescence was detected in the developing anthers, filaments (FIG. 7C), stigma, style, ovary wall, and ovules (FIG. 7D). When an older flower bud in which the petals were no longer enclosed by sepals was dissected, strong fluorescence was detected in petals (FIG. 7F) and in the fused base of filaments, but not in the separated part of filaments or in the anthers (FIG. 7G). Strong fluorescence was also detected in the style but not in the ovary part of the pistil (FIG. 7H) or in ovules. The seemingly glowing stigma in FIG. 7H glowed stronger under a non-specific cyan filter, suggesting that the fluorescence in stigma was non-specific auto fluorescence (FIG. 7I). When an open flower post to pollination was dissected, fluorescence was detected in the same tissues, i.e., petals, the stigma, and filaments but still not in sepals, carpel wall, or ovules (FIG. 7K). Fluorescence was detected in the entire filaments including the separated part but still not in anthers (FIG. 7L). No fluorescence was detected in pollen grains scattered on the stigma and carpel hairs (FIG. 7M). Fluorescence remained strong in the lower fused petals and faded away in the side petals and in the upper petal (FIG. 7N, O, P). When a young pod (~10 mm long) was cut longitudinally to expose the pod wall and the inside developing seed, no fluorescence was detected (FIG. 7P).

In conclusion, the LTP1:YFP expression was only detected in petals, filaments, and was strongest in the style of a soybean flower. The expression was first detectable in the lower petals in young flower bud and faded away first in the upper petal as the flower aged. No expression was detectable in other parts of the flower or other tissues of transgenic soybean plants.

Ten out of 13 transgenic events expressed YFP in the same manner as described in details above (Table 3). The other three events though also contained the transgene as revealed by qPCR and regular PCR but failed to express YFP.

What is claimed is:

1. An isolated polynucleotide comprising:

a) a nucleotide sequence comprising the sequence set forth in SEQ ID NO:1;

b) a nucleotide sequence comprising a fragment of SEQ ID NO:1 selected from the group consisting of: SEQ ID NO:2, SEQ ID NO:3, SEQ ID NO:4, and SEQ ID NO:5; or c) the full length complement of (a) or (b);

wherein said nucleotide sequence is a promoter.

2. A recombinant DNA construct comprising the isolated polynucleotide of claim 1 operably linked to at least one heterologous sequence.

3. The recombinant DNA construct of claim 2 wherein the heterologous nucleotide sequence encodes a gene involved in anthocyanin biosynthesis, a gene involved in the synthesis of fragrant fatty acid derivatives, a gene that is determinative of flower morphology, or a gene involved in biosynthesis of plant cytokinin.

4. The recombinant DNA construct of claim 3, wherein the gene involved in anthocyanin biosynthesis is dyhydroflavonol 4-reductase, flavonoid 3,5-hydroxylase, chalcone synthase, chalcone isomerase, flavonoid 3-hydroxylase, anthocyanin synthase, or UDP-glucose 3-O-flavonoid glucosyl transferase.

5. The recombinant DNA construct of claim 3, wherein the gene involved in the synthesis of fragrant fatty acid derivatives is S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthase, (E)-β-ocimene synthase, orcinol O-methyltransferase, or limonene synthase.

6. The recombinant DNA construct of claim 3, wherein the gene that is determinative of flower morphology is AGAMOUS, APETALA, or PISTILLATA.

7. The recombinant DNA construct of claim 3, wherein the gene involved in biosynthesis of plant cytokinin is isopentenyl transferase.

8. A vector comprising the recombinant DNA construct of claim 2.

9. A cell comprising the recombinant DNA construct of claim 2.

10. The cell of claim 9, wherein the cell is a plant cell.

11. A transgenic plant having stably incorporated into its genome the recombinant DNA construct of claim 2.

12. The transgenic plant of claim 11, wherein the plant is a flowering plant.

13. The transgenic plant of claim 12, wherein the flowering plant is rose, carnation, *Gerbera, Chrysanthemum*, tulip, Gladioli, *Alstroemeria, Anthurium, lisianthus*, larkspur, irises, orchid, snapdragon, African violet, or *azalea*.

14. A transgenic seed produced by the transgenic plant of claim 11.

15. A method of expressing a coding sequence or an RNA in a flowering plant comprising:

a) introducing the recombinant DNA construct of claim 2 into the plant, wherein the at least one heterologous sequence comprises a coding sequence;

b) growing the plant of step a); and c) selecting a plant displaying expression of the coding sequence or the RNA of the recombinant DNA construct.

16. A method of transgenically altering a flower trait of a flowering plant, comprising:

a) introducing a recombinant DNA construct of claim 2 into the flowering plant;

b) growing a fertile, mature flowering plant resulting from step a); and c) selecting a flowering plant expressing the at least one heterologous nucleotide sequence in flower tissue based on the altered flower trait.

17. The method of claim 16 wherein the flower trait is color, morphology, or fragrance.

18. The isolated polynucleotide of claim 1, wherein the nucleotide sequence of b) is SEQ ID NO:2.

19. The isolated polynucleotide of claim 1, wherein the nucleotide sequence of b) is SEQ ID NO:3.

20. The isolated polynucleotide of claim 1, wherein the nucleotide sequence of b) is SEQ ID NO:4.

21. The isolated polynucleotide of claim 1, wherein the nucleotide sequence of b) is SEQ ID NO:5.

* * * * *

SEQUENCE LISTING

<160> NUMBER OF SEQ ID NOS: 50

<210> SEQ ID NO 1
<211> LENGTH: 1136
<212> TYPE: DNA
<213> ORGANISM: Glycine max

<400> SEQUENCE: 1
gggtcctact cctactcgac aatattctaa tttctaagac atatgtttta tctgtttttg 60
tttttcagtt tttaaaacac ttgttttgaa aattattttc aaaacataat aaaatagaaa 120
gttacaaaat ggtaaagaaa aaactgagaa gaaaaacaac catgagttta atttttggta 180
aagaagtagt ttatatatcg ttggctttat acgaatataa cgaaaacacc gagtgaaaaa 240
atgttacgca gaaaagagat agatagaatg agaagagaga aaatataaca gattcgatat 300
aaaatacaaa gatatagaaa tgataatgtc gtagaaaatg ttatatgaat aagtgatcta 360
acacagaaaa aagaaagaag tgagttaatt agacaaaaag agaagaaact tgtgttttga 420
gaacaaaatt gtaacgaata atcaaacact aaaatgaaca atactcagtt acttacgatg 480
acttgaacga tgtcggcaga agtgggaaat aataaaaagt aagtccatac aaaataacgt 540
gccaaattca ttttgggtga tgcagaaacc tgccaaacca catggckata tatatatata 600
gaaacagttg atcagttagc aaccctttgc caactctgat atattatgta ttttttttta 660
tgttttagtt attttatttt attttattca aaattttaat attttaaaat ttaaaatcta 720
actaatgtat tttttaaaat atattcttat ttaatattca cgtgataaaa tataaaatat 780
aaaatatcaa tatattaaat aagaatattt taattcaaat ataatatttt ttaattttat 840
taaatattta ttaattcata tataatatta aggtataaac tcattaattg tatcacgttg 900
taggtttgag catgcggtta ttcaattgct tgcattaaat gaaatcaacc aggaactagc 960
tatcattcct tagttcactt ttcacttaac gaactcaayc agctggctga atctgaactc 1020
tatatatagt ccttaaattc acaaatcata acatcaaaac catcacttca tactcactag 1080
tcactatagc tcacccttga agaagtgcaa tttcatcctc taactcttcc aaatcc 1136

<210> SEQ ID NO 2
<211> LENGTH: 927
<212> TYPE: DNA
<213> ORGANISM: Glycine max

<400> SEQUENCE: 2
tacgaatata acgaaaacac cgagtgaaaa aatgttacgc agaaaagaga tagatagaat 60
gagaagagag aaaatataac agattcgata taaaatacaa agatatagaa atgataatgt 120
cgtagaaaat gttatatgaa taagtgatct aacacagaaa aaagaaagaa gtgagttaat 180
tagacaaaaa gagaagaaac ttgtgttttg agaacaaaat tgtaacgaat aatcaaacac 240
taaaatgaac aatactcagt tacttacgat gacttgaacg atgtcggcag aagtgggaaa 300
taataaaaag taagtccata caaaataacg tgccaaattc attttgggtg atgcagaaac 360
ctgccaaacc acatggckat atatatatat agaaacagtt gatcagttag caaccctttg 420
ccaactctga tatattatgt attttttttt atgttttagt tattttattt tattttattc 480
aaaattttaa tattttaaaa tttaaaatct aactaatgta ttttttaaaa tatattctta 540
tttaatattc acgtgataaa atataaaata taaaatatca atatattaaa taagaatatt 600
ttaattcaaa tataatattt tttaatttta ttaaatattt attaattcat atataatatt 660
aaggtataaa ctcattaatt gtatcacgtt gtaggtttga gcatgcggtt attcaattgc 720
ttgcattaaa tgaaatcaac caggaactag ctatcattcc ttagttcact tttcacttaa 780
cgaactcaay cagctggctg aatctgaact ctatatatag tccttaaatt cacaaatcat 840
aacatcaaaa ccatcacttc atactcacta gtcactatag ctcacccttg aagaagtgca 900
atttcatcct ctaactcttc caaatcc 927

<210> SEQ ID NO 3
<211> LENGTH: 738
<212> TYPE: DNA
<213> ORGANISM: Glycine max

<400> SEQUENCE: 3
agagaagaaa cttgtgtttt gagaacaaaa ttgtaacgaa taatcaaaca ctaaaatgaa 60
caatactcag ttacttacga tgacttgaac gatgtcggca gaagtgggaa ataataaaaa 120
gtaagtccat acaaaataac gtgccaaatt cattttgggt gatgcagaaa cctgccaaac 180
cacatggcka tatatatata tagaaacagt tgatcagtta gcaacccttt gccaactctg 240
atatattatg tatttttttt tatgttttag ttattttatt ttatttttatt caaaatttta 300 atattttaaa atttaaaatc taactaatgt attttttaaa atatattctt atttaatatt 360
cacgtgataa aatataaaat ataaaatatc aatatattaa ataagaatat tttaattcaa 420
atataatatt ttttaatttt attaaatatt tattaattca tatataatat taaggtataa 480
actcattaat tgtatcacgt tgtaggtttg agcatgcggt tattcaattg cttgcattaa 540
atgaaatcaa ccaggaacta gctatcattc cttagttcac ttttcactta acgaactcaa 600
ycagctggct gaatctgaac tctatatata gtccttaaat tcacaaatca taacatcaaa 660
accatcactt catactcact agtcactata gctcaccctt gaagaagtgc aatttcatcc 720
tctaactctt ccaaatcc 738

<210> SEQ ID NO 4
<211> LENGTH: 527
<212> TYPE: DNA
<213> ORGANISM: Glycine max

<400> SEQUENCE: 4
gatcagttag caaccctttg ccaactctga tatattatgt attttttttt atgttttagt 60
tattttattt tattttattc aaaattttaa tattttaaaa tttaaaatct aactaatgta 120
ttttttaaaa tatattctta tttaatattc acgtgataaa atataaaata taaaatatca 180
atatattaaa taagaatatt ttaattcaaa tataatattt tttaatttta ttaaatattt 240
attaattcat atataatatt aaggtataaa ctcattaatt gtatcacgtt gtaggtttga 300
gcatgcggtt attcaattgc ttgcattaaa tgaaatcaac caggaactag ctatcattcc 360
ttagttcact tttcacttaa cgaactcaay cagctggctg aatctgaact ctatatatag 420
tccttaaatt cacaaatcat aacatcaaaa ccatcacttc atactcacta gtcactatag 480
ctcacccttg aagaagtgca atttcatcct ctaactcttc caaatcc 527

<210> SEQ ID NO 5
<211> LENGTH: 257
<212> TYPE: DNA
<213> ORGANISM: Glycine max

<400> SEQUENCE: 5
ctcattaatt gtatcacgtt gtaggtttga gcatgcggtt attcaattgc ttgcattaaa 60

```
tgaaatcaac caggaactag ctatcattcc ttagttcact tttcacttaa cgaactcaay    120

cagctggctg aatctgaact ctatatatag tccttaaatt cacaaatcat aacatcaaaa    180

ccatcacttc atactcacta gtcactatag ctcacccttg aagaagtgca atttcatcct    240

ctaactcttc caaatcc                                                   257


<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6

caatttcatc ctctaactct tccaaatcc                                       29


<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7

gggtcctact cctactcgac aatattc                                         27


<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8

tacgaatata acgaaaacac cgagtg                                          26


<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9

agagaagaaa cttgtgtttt gagaacaa                                        28


<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10

gatcagttag caaccctttg cca                                             23


<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11

ctcattaatt gtatcacgtt gtaggtttg                                       29
```

-continued

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
cttcatgaca agcagtgagc tagcc 25

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
gtaatacgac tcactatagg gcacg 25

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
ccatggattt ggaagagtta gaggatgaaa ttg 33

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
ctatagggca cgcgtggtcg ac 22

<210> SEQ ID NO 16
<211> LENGTH: 574
<212> TYPE: DNA
<213> ORGANISM: Glycine max

<400> SEQUENCE: 16
ttcatactca ctagtcacta tagctcaccc ttgaagaagt gcaatttcat cctctaactc 60
ttccaaatca tggctagctc actgcttgtc atgaaggtta caagctgcat ggttgcggtg 120
ttgatggtta gttttggaca cataattccc ttggcagaag ctgaaattcc atgtggcagg 180
gtgcaaatca cagtggctcc atgcataggg tacctaaggg gtcctggtgg aggtgtccct 240
gcagcatgct gcaatggggt taggagcata aacaaggaag ccaaaaccac cccagatcgt 300
caaggggtgt gtaggtgcct caaaaccact gctttgagct tgcctggact caaccttgca 360
acccttgcag ctctccctag caaatgcggg gtcaacttgc cctacaagat atcccccacc 420
attgattgca acacggtaaa gcactgagca gttgcacgag ggtttatgct tgttgacttt 480
aaacttgttt cgcagtaata atcagcaaag agagaacaaa gatggtttaa tttcttccat 540
tgtctggatc ccactaggga gtatacttta tact 574

<210> SEQ ID NO 17
<211> LENGTH: 8638
<212> TYPE: DNA

<213> ORGANISM: Artificial Sequence
<220> FEATURE:
<223> OTHER INFORMATION: nucleotide sequence of QC267

<400> SEQUENCE: 17

```
gggggatcca tggcccacag caagcacggc ctgaaggagg agatgaccat gaagtaccac     60

atggagggct gcgtgaacgg ccacaagttc gtgatcaccg gcgagggcat cggctacccc    120

ttcaagggca agcagaccat caacctgtgc gtgatcgagg gcggccccct gcccttcagc    180

gaggacatcc tgagcgccgg cttcaagtac ggcgaccgga tcttcaccga gtacccccag    240

gacatcgtgg actacttcaa gaacagctgc cccgccggct acacctgggg ccggagcttc    300

ctgttcgagg acggcgccgt gtgcatctgt aacgtggaca tcaccgtgag cgtgaaggag    360

aactgcatct accacaagag catcttcaac ggcgtgaact tccccgccga cggccccgtg    420

atgaagaaga tgaccaccaa ctgggaggcc agctgcgaga agatcatgcc cgtgcctaag    480

cagggcatcc tgaagggcga cgtgagcatg tacctgctgc tgaaggacgg cggccggtac    540

cggtgccagt tcgacaccgt gtacaaggcc aagagcgtgc ccagcaagat gcccgagtgg    600

cacttcatcc agcacaagct gctgcgggag gaccggagcg acgccaagaa ccagaagtgg    660

cagctgaccg agcacgccat cgccttcccc agcgccctgg cctgagagct cgaatttccc    720

cgatcgttca aacatttggc aataaagttt cttaagattg aatcctgttg ccggtcttgc    780

gatgattatc atataatttc tgttgaatta cgttaagcat gtaataatta acatgtaatg    840

catgacgtta tttatgagat gggtttttat gattagagtc ccgcaattat acatttaata    900

cgcgatagaa aacaaaatat agcgcgcaaa ctaggataaa ttatcgcgcg cggtgtcatc    960

tatgttacta gatcgggaat tctagtggcc ggcccagctg atgtaccggc gcgcccgatc   1020

atccggatat agttcctcct ttcagcaaaa aacccctcaa gacccgttta gaggccccaa   1080

ggggttatgc tagttattgc tcagcggtgg cagcagccaa ctcagcttcc tttcgggctt   1140

tgttagcagc cggatcgatc caagctgtac ctcactattc ctttgccctc ggacgagtgc   1200

tggggcgtcg gtttccacta tcggcgagta cttctacaca gccatcggtc cagacggccg   1260

cgcttctgcg ggcgatttgt gtacgcccga cagtcccggc tccggatcgg acgattgcgt   1320

cgcatcgacc ctgcgcccaa gctgcatcat cgaaattgcc gtcaaccaag ctctgataga   1380

gttggtcaag accaatgcgg agcatatacg cccggagccg cggcgatcct gcaagctccg   1440

gatgcctccg ctcgaagtag cgcgtctgct gctccataca agccaaccac ggcctccaga   1500

agaagatgtt ggcgacctcg tattgggaat ccccgaacat cgcctcgctc cagtcaatga   1560

ccgctgttat gcggccattg tccgtcagga cattgttgga gccgaaatcc gcgtgcacga   1620

ggtgccggac ttcggggcag tcctcggccc aaagcatcag ctcatcgaga gcctgcgcga   1680

cggacgcact gacggtgtcg tccatcacag tttgccagtg atacacatgg ggatcagcaa   1740

tcgcgcatat gaaatcacgc catgtagtgt attgaccgat tccttgcggt ccgaatgggc   1800

cgaacccgct cgtctggcta agatcggccg cagcgatcgc atccatagcc tccgcgaccg   1860

gctgcagaac agcgggcagt tcggtttcag gcaggtcttg caacgtgaca ccctgtgcac   1920

ggcgggagat gcaataggtc aggctctcgc tgaattcccc aatgtcaagc acttccggaa   1980

tcgggagcgc ggccgatgca aagtgccgat aaacataacg atctttgtag aaaccatcgg   2040

cgcagctatt tacccgcagg acatatccac gccctcctac atcgaagctg aaagcacgag   2100

attcttcgcc ctccgagagc tgcatcaggt cggagacgct gtcgaacttt tcgatcagaa   2160

acttctcgac agacgtcgcg gtgagttcag gcttttccat gggtatatct ccttcttaaa   2220
```

-continued

```
gttaaacaaa attatttcta gagggaaacc gttgtggtct ccctatagtg agtcgtatta   2280
atttcgcggg atcgagatct gatcaacctg cattaatgaa tcggccaacg cgcggggaga   2340
ggcggtttgc gtattgggcg ctcttccgct tcctcgctca ctgactcgct gcgctcggtc   2400
gttcggctgc ggcgagcggt atcagctcac tcaaaggcgg taatacggtt atccacagaa   2460
tcaggggata acgcaggaaa gaacatgtga gcaaaaggcc agcaaaaggc caggaaccgt   2520
aaaaaggccg cgttgctggc gtttttccat aggctccgcc cccctgacga gcatcacaaa   2580
aatcgacgct caagtcagag gtggcgaaac ccgacaggac tataaagata ccaggcgttt   2640
ccccctggaa gctccctcgt gcgctctcct gttccgaccc tgccgcttac cggatacctg   2700
tccgcctttc tcccttcggg aagcgtggcg ctttctcaat gctcacgctg taggtatctc   2760
agttcggtgt aggtcgttcg ctccaagctg ggctgtgtgc acgaaccccc cgttcagccc   2820
gaccgctgcg ccttatccgg taactatcgt cttgagtcca acccggtaag acacgactta   2880
tcgccactgg cagcagccac tggtaacagg attagcagag cgaggtatgt aggcggtgct   2940
acagagttct tgaagtggtg gcctaactac ggctacacta gaaggacagt atttggtatc   3000
tgcgctctgc tgaagccagt taccttcgga aaaagagttg gtagctcttg atccggcaaa   3060
caaaccaccg ctggtagcgg tggttttttt gtttgcaagc agcagattac gcgcagaaaa   3120
aaaggatctc aagaagatcc tttgatcttt tctacggggt ctgacgctca gtggaacgaa   3180
aactcacgtt aagggatttt ggtcatgaca ttaacctata aaaataggcg tatcacgagg   3240
ccctttcgtc tcgcgcgttt cggtgatgac ggtgaaaacc tctgacacat gcagctcccg   3300
gagacggtca cagcttgtct gtaagcggat gccgggagca gacaagcccg tcagggcgcg   3360
tcagcgggtg ttggcgggtg tcggggctgg cttaactatg cggcatcaga gcagattgta   3420
ctgagagtgc accatatgga catattgtcg ttagaacgcg gctacaatta atacataacc   3480
ttatgtatca tacacatacg atttaggtga cactatagaa cggcgcgcca agctgggtct   3540
agaactagaa acgtgatgcc acttgttatt gaagtcgatt acagcatcta ttctgtttta   3600
ctatttataa ctttgccatt tctgactttt gaaaactatc tctggatttc ggtatcgctt   3660
tgtgaagatc gagcaaaaga gacgttttgt ggacgcaatg gtccaaatcc gttctacatg   3720
aacaaattgg tcacaatttc cactaaaagt aaataaatgg caagttaaaa aaggaatatg   3780
cattttactg attgcctagg tgagctccaa gagaagttga atctacacgt ctaccaaccg   3840
ctaaaaaaag aaaaacattg aatatgtaac ctgattccat tagcttttga cttcttcaac   3900
agattctcta cttagatttc taacagaaat attattacta gcacatcatt ttcagtctca   3960
ctacagcaaa aaatccaacg gcacaataca gacaacagga gatatcagac tacagagata   4020
gatagatgct actgcatgta gtaagttaaa taaaaggaaa ataaaatgtc ttgctaccaa   4080
aactactaca gactatgatg ctcaccacag gccaaatcct gcaactagga cagcattatc   4140
ttatatatat tgtacaaaac aagcatcaag gaacatttgg tctaggcaat cagtacctcg   4200
ttctaccatc accctcagtt atcacatcct tgaaggatcc attactggga atcatcggca   4260
acacatgctc ctgatggggc acaatgacat caagaaggta ggggccaggg gtgtccaaca   4320
ttctctgaat tgccgctcta agctcttcct tcttcgtcac tcgcgctgcc ggtatcccac   4380
aagcatcagc aaacttgagc atgtttggga atatctcgct ctcgctagac ggatctccaa   4440
gataggtgtg agctctattg gacttgtaga acctatcctc caactgaacc accataccca   4500
aatgctgatt gttcaacaac aatatcttaa ctgggagatt ctccactctt atagtggcca   4560
actcctgaac attcatgatg aaactaccat ccccatcaat gtcaaccaca acagccccag   4620
```

-continued

```
ggttagcaac agcagcacca atagccgcag gcaatccaaa acccatggct ccaagacccc   4680
ctgaggtcaa ccactgcctc ggtctcttgt acttgtaaaa ctgcgcagcc cacatttgat   4740
gctgcccaac cccagtacta acaatagcat ctccattagt caactcatca agaacctcga   4800
tagcatgctg cggagaaatc gcgtcctgga atgtcttgta acccaatgga aacttgtgtt   4860
tctgcacatt aatctcttct ctccaacctc caagatcaaa cttaccctcc actcctttct   4920
cctccaaaat catattaatt cccttcaagg ccaacttcaa atccgcgcaa accgacacgt   4980
gcgcctgctt gttcttccca atctcggcag aatcaatatc aatgtgaaca atcttagccc   5040
tactagcaaa agcctcaagc ttcccagtaa cacggtcatc aaaccttacc ccaaaggcaa   5100
gcaacaaatc actattgtca acagcatagt tagcataaac agtaccatgc atacccagca   5160
tctgaaggga atattcatca ccaataggaa aagttccaag acccattaaa gtgctagcaa   5220
cgggaatacc agtgagttca acaaagcgcc tcaattcagc actggaattc aaactgccac   5280
cgccgacgta gagaacgggc ttttgggcct ccatgatgag tctgacaatg tgttccaatt   5340
gggcctcggc ggggggcctg ggcagcctgg cgaggtaacc ggggaggtta acgggctcgt   5400
cccaattagg cacggcgagt tgctgctgaa cgtctttggg aatgtcgatg aggaccggac   5460
cggggcggcc ggaggtggcg acgaagaaag cctcggcgac gacgcggggg atgtcgtcga   5520
cgtcgaggat gaggtagttg tgcttcgtga tggatctgct cacctccacg atcggggttt   5580
cttggaaggc gtcggtgccg atcatccggc gggcgacctg gccggtgatg gcgacgactg   5640
ggacgctgtc cattaaagcg tcggcgaggc cgctcacgag gttggtggcg ccggggccgg   5700
aggtggcaat gcagacgccg gggaggccgg aggaacgcgc gtagccttcg gcggcgaaga   5760
cgccgccctg ctcgtggcgc gggagcacgt tgcggatggc ggcggagcgc gtgagcgcct   5820
ggtggatctc catcgacgca ccgccggggt acgcgaacac cgtcgtcacg ccctgcctct   5880
ccagcgcctc cacaaggatg tccgcgccct tgcgaggttc gccggaggcg aaccgtgaca   5940
cgaagggctc cgtggtcggc gcttccttgg tgaagggcgc cgccgtgggg ggtttggaga   6000
tggaacattt gattttgaga gcgtggttgg gtttggtgag ggtttgatga gagagaggga   6060
gggtggatct agtaatgcgt ttggggaagg tggggtgtga agaggaagaa gagaatcggg   6120
tggttctgga agcggtggcc gccattgtgt tgtgtggcat ggttatactt caaaaactgc   6180
acaacaagcc tagagttagt acctaaacag taaatttaca acagagagca aagacacatg   6240
caaaaatttc agccataaaa aaagttataa tagaatttaa agcaaaagtt tcattttta    6300
aacatatata caaacaaact ggatttgaag gaagggatta attcccctgc tcaaagtttg   6360
aattcctatt gtgacctata ctcgaataaa attgaagcct aaggaatgta tgagaaacaa   6420
gaaaacaaaa caaaactaca gacaaacaag tacaattaca aaattcgcta aaattctgta   6480
atcaccaaac cccatctcag tcagcacaag gcccaaggtt tattttgaaa taaaaaaaaa   6540
gtgattttat ttctcataag ctaaaagaaa gaaaggcaat tatgaaatga tttcgactag   6600
atctgaaagt caaacgcgta ttccgcagat attaaagaaa gagtagagtt tcacatggat   6660
cctagatgga cccagttgag gaaaaagcaa ggcaaagcaa accagaagtg caagatccga   6720
aattgaacca cggaatctag gatttggtag agggagaaga aaagtacctt gagaggtaga   6780
agagaagaga agagcagaga gatatatgaa cgagtgtgtc ttggtctcaa ctctgaagcg   6840
atacgagttt agaggggagc attgagttcc aatttatagg gaaaccgggt ggcaggggtg   6900
agttaatgac ggaaaagccc ctaagtaacg agattggatt gtgggttaga ttcaaccgtt   6960
tgcatccgcg gcttagattg gggaagtcag agtgaatctc aaccgttgac tgagttgaaa   7020
```

attgaatgta gcaaccaatt gagccaaccc cagcctttgc cctttgattt tgatttgttt 7080
gttgcatact ttttatttgt cttctggttc tgactctctt tctctcgttt caatgccagg 7140
ttgcctactc ccacaccact cacaagaaga ttctactgtt agtattaaat attttttaat 7200
gtattaaatg atgaatgctt ttgtaaacag aacaagacta tgtctaataa gtgtcttgca 7260
acatttttta agaaattaaa aaaaatatat ttattatcaa aatcaaatgt atgaaaaatc 7320
atgaataata taattttata catttttta aaaaatcttt taatttctta attaatatct 7380
taaaaataat gattaatatt taacccaaaa taattagtat gattggtaag gaagatatcc 7440
atgttatgtt tggatgtgag tttgatctag agcaaagctt actagagtcg acctgcagcc 7500
cgggtcctac tcctactcga caatattcta atttctaaga catatgtttt atctgttttt 7560
gtttttcagt ttttaaaaca cttgttttga aaattatttt caaaacataa taaaatagaa 7620
agttacaaaa tggtaaagaa aaaactgaga agaaaaacaa ccatgagttt aatttttggt 7680
aaagaagtag tttatatatc gttggcttta tacgaatata acgaaaacac cgagtgaaaa 7740
aatgttacgc agaaaagaga tagatagaat gagaagagag aaaatataac agattcgata 7800
taaaatacaa agatatagaa atgataatgt cgtagaaaat gttatatgaa taagtgatct 7860
aacacagaaa aaagaaagaa gtgagttaat tagacaaaaa gagaagaaac ttgtgttttg 7920
agaacaaaat tgtaacgaat aatcaaacac taaaatgaac aatactcagt tacttacgat 7980
gacttgaacg atgtcggcag aagtgggaaa taataaaaag taagtccata caaaataacg 8040
tgccaaattc attttgggtg atgcagaaac ctgccaaacc acatggckat atatatatat 8100
agaaacagtt gatcagttag caaccctttg ccaactctga tatattatgt atttttttt 8160 atgttttagt tattttattt tattttattc aaaattttaa tattttaaaa tttaaaatct 8220
aactaatgta ttttttaaaa tatattctta tttaatattc acgtgataaa atataaaata 8280
taaaatatca atatattaaa taagaatatt ttaattcaaa tataatattt tttaatttta 8340
ttaaatattt attaattcat atataatatt aaggtataaa ctcattaatt gtatcacgtt 8400
gtaggtttga gcatgcggtt attcaattgc ttgcattaaa tgaaatcaac caggaactag 8460
ctatcattcc ttagttcact tttcacttaa cgaactcaay cagctggctg aatctgaact 8520
ctatatatag tccttaaatt cacaaatcat aacatcaaaa ccatcacttc atactcacta 8580
gtcactatag ctcacccttg aagaagtgca atttcatcct ctaactcttc caaatccc 8638

<210> SEQ ID NO 18
<211> LENGTH: 4794
<212> TYPE: DNA
<213> ORGANISM: Artificial Sequence
<220> FEATURE:
<223> OTHER INFORMATION: nucleotide sequence of QC267-1Y

<400> SEQUENCE: 18
cttgtacaaa gtggttgatg ggatccatgg cccacagcaa gcacggcctg aaggaggaga 60
tgaccatgaa gtaccacatg gagggctgcg tgaacggcca caagttcgtg atcaccggcg 120
agggcatcgg ctaccccttc aagggcaagc agaccatcaa cctgtgcgtg atcgagggcg 180 gcccccctgcc cttcagcgag gacatcctga gcgccggctt caagtacggc gaccggatct 240
tcaccgagta cccccaggac atcgtggact acttcaagaa cagctgcccc gccggctaca 300
cctggggccg gagcttcctg ttcgaggacg gcgccgtgtg catctgtaac gtggacatca 360
ccgtgagcgt gaaggagaac tgcatctacc acaagagcat cttcaacggc gtgaacttcc 420
ccgccgacgg ccccgtgatg aagaagatga ccaccaactg ggaggccagc tgcgagaaga 480

-continued

```
tcatgcccgt gcctaagcag ggcatcctga agggcgacgt gagcatgtac ctgctgctga    540
aggacggcgg ccggtaccgg tgccagttcg acaccgtgta caaggccaag agcgtgccca    600
gcaagatgcc cgagtggcac ttcatccagc acaagctgct gcgggaggac cggagcgacg    660
ccaagaacca gaagtggcag ctgaccgagc acgccatcgc cttccccagc gccctggcct    720
gagagctcga atttccccga tcgttcaaac atttggcaat aaagtttctt aagattgaat    780
cctgttgccg gtcttgcgat gattatcata taatttctgt tgaattacgt taagcatgta    840
ataattaaca tgtaatgcat gacgttattt atgagatggg tttttatgat tagagtcccg    900
caattataca tttaatacgc gatagaaaac aaaatatagc gcgcaaacta ggataaatta    960
tcgcgcgcgg tgtcatctat gttactagat cgggaattct agtggccggc ccagctgata   1020
tccatcacac tggcggccgc tcgagttcta tagtgtcacc taaatcgtat gtgtatgata   1080
cataaggtta tgtattaatt gtagccgcgt tctaacgaca atatgtccat atggtgcact   1140
ctcagtacaa tctgctctga tgccgcatag ttaagccagc cccgacaccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct atttttatag gttaatgtca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca cagcccagct tggagcgaac gacctacacc   1800
gaactgagat acctacagcg tgagcattga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040
tttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca aagatcgtta tgtttatcgg cactttgcat cggccgcgct   2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
```

-continued

```
gtccgtcgcg caggctctcg atgagctgat gctttgggcc gaggactgcc ccgaagtccg   2940

gcacctcgtg cacgcggatt tcggctccaa caatgtcctg acggacaatg gccgcataac   3000

agcggtcatt gactggagcg aggcgatgtt cggggattcc caatacgagg tcgccaacat   3060

cttcttctgg aggccgtggt tggcttgtat ggagcagcag acgcgctact tcgagcggag   3120

gcatccggag cttgcaggat cgccgcggct ccgggcgtat atgctccgca ttggtcttga   3180

ccaactctat cagagcttgg ttgacggcaa tttcgatgat gcagcttggg cgcagggtcg   3240

atgcgacgca atcgtccgat ccggagccgg gactgtcggg cgtacacaaa tcgcccgcag   3300

aagcgcggcc gtctggaccg atggctgtgt agaagtactc gccgatagtg gaaaccgacg   3360

ccccagcact cgtccgaggg caaaggaata gtgaggtaca gcttggatcg atccggctgc   3420

taacaaagcc cgaaaggaag ctgagttggc tgctgccacc gctgagcaat aactagcata   3480

accccttggg gcctctaaac gggtcttgag gggttttttg ctgaaaggag gaactatatc   3540

cggatgatcg tcgaggcctc acgtgttaac aagcttgcat gcctgcaggt ttatcaacaa   3600

gtttgtacaa aaaagcaggc tccgaattcg cccttgggtc ctactcctac tcgacaatat   3660

tctaatttct aagacatatg ttttatctgt ttttgttttt cagtttttaa aacacttgtt   3720

ttgaaaatta ttttcaaaac ataataaaat agaaagttac aaaatggtaa agaaaaaact   3780

gagaagaaaa acaaccatga gtttaatttt tggtaaagaa gtagtttata tatcgttggc   3840

tttatacgaa tataacgaaa acaccgagtg aaaaaatgtt acgcagaaaa gagatagata   3900

gaatgagaag agagaaaata taacagattc gatataaaat acaaagatat agaaatgata   3960

atgtcgtaga aaatgttata tgaataagtg atctaacaca gaaaaaagaa agaagtgagt   4020

taattagaca aaaagagaag aaacttgtgt tttgagaaca aaattgtaac gaataatcaa   4080

acactaaaat gaacaatact cagttactta cgatgacttg aacgatgtcg gcagaagtgg   4140

gaaataataa aaagtaagtc catacaaaat aacgtgccaa attcattttg ggtgatgcag   4200

aaacctgcca aaccacatgg ckatatatat atatagaaac agttgatcag ttagcaaccc   4260

tttgccaact ctgatatatt atgtattttt ttttatgttt tagttatttt attttatttt   4320

attcaaaatt ttaatatttt aaaatttaaa atctaactaa tgtatttttt aaaatatatt   4380

cttatttaat attcacgtga taaaatataa aatataaaat atcaatatat taaataagaa   4440

tattttaatt caaatataat attttttaat tttattaaat atttattaat tcatatataa   4500

tattaaggta taaactcatt aattgtatca cgttgtaggt ttgagcatgc ggttattcaa   4560

ttgcttgcat taaatgaaat caaccaggaa ctagctatca ttccttagtt cacttttcac   4620

ttaacgaact caaycagctg gctgaatctg aactctatat atagtcctta aattcacaaa   4680

tcataacatc aaaaccatca cttcatactc actagtcact atagctcacc cttgaagaag   4740

tgcaatttca tcctctaact cttccaaatc caagggcgaa ttcgacccag cttt         4794
```

<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19

```
gaccaagaca cactcgttca tatatc                                         26
```

<210> SEQ ID NO 20
<211> LENGTH: 25
<212> TYPE: DNA

<213> ORGANISM: Artificial Sequence
<220> FEATURE:
<223> OTHER INFORMATION: primer

<400> SEQUENCE: 20
tctgctgctc aatgtttaca aggac 25

<210> SEQ ID NO 21
<211> LENGTH: 48
<212> TYPE: DNA
<213> ORGANISM: Artificial Sequence
<220> FEATURE:
<223> OTHER INFORMATION: longer strand sequence of the adaptor supplied in ClonTech GenomeWalker kit

<400> SEQUENCE: 21
gtaatacgac tcactatagg gcacgcgtgg tcgacggccc gggctggt 48

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
ataatcccgg gtcctactcc tactcgacaa 30

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
gagctacccg ggatttggaa gagttagagg atg 33

<210> SEQ ID NO 24
<211> LENGTH: 17
<212> TYPE: DNA
<213> ORGANISM: Artificial Sequence
<220> FEATURE:
<223> OTHER INFORMATION: MPSS tag sequence

<400> SEQUENCE: 24
gatcccacta gggagta 17

<210> SEQ ID NO 25
<211> LENGTH: 22
<212> TYPE: DNA
<213> ORGANISM: Artificial Sequence
<220> FEATURE:
<223> OTHER INFORMATION: sense primer

<400> SEQUENCE: 25
ggaagaagag aatcgggtgg tt 22

<210> SEQ ID NO 26
<211> LENGTH: 23
<212> TYPE: DNA
<213> ORGANISM: Artificial Sequence
<220> FEATURE:
<223> OTHER INFORMATION: FAM labeled fluorescent DNA oligo probe

<400> SEQUENCE: 26
attgtgttgt gtggcatggt tat 23

<210> SEQ ID NO 27
<211> LENGTH: 23
<212> TYPE: DNA
<213> ORGANISM: Artificial Sequence
<220> FEATURE:
<223> OTHER INFORMATION: antisense primer

<400> SEQUENCE: 27
ggcttgttgt gcagtttttg aag 23

<210> SEQ ID NO 28
<211> LENGTH: 20
<212> TYPE: DNA
<213> ORGANISM: Artificial Sequence
<220> FEATURE:
<223> OTHER INFORMATION: sense primer

<400> SEQUENCE: 28
aacggccaca agttcgtgat 20

<210> SEQ ID NO 29
<211> LENGTH: 20
<212> TYPE: DNA
<213> ORGANISM: Artificial Sequence
<220> FEATURE:
<223> OTHER INFORMATION: FAM labeled fluorescent DNA oligo probe

<400> SEQUENCE: 29
accggcgagg gcatcggcta 20

<210> SEQ ID NO 30
<211> LENGTH: 20
<212> TYPE: DNA
<213> ORGANISM: Artificial Sequence
<220> FEATURE:
<223> OTHER INFORMATION: antisense primer

<400> SEQUENCE: 30
cttcaagggc aagcagacca 20

<210> SEQ ID NO 31
<211> LENGTH: 24
<212> TYPE: DNA
<213> ORGANISM: Artificial Sequence
<220> FEATURE:
<223> OTHER INFORMATION: sense primer

<400> SEQUENCE: 31
caaacttgac aaagccacaa ctct 24

<210> SEQ ID NO 32
<211> LENGTH: 20
<212> TYPE: DNA
<213> ORGANISM: Artificial Sequence
<220> FEATURE:
<223> OTHER INFORMATION: VIC labeled DNA oligo probe

<400> SEQUENCE: 32
ctctcatctc atataaatac 20

<210> SEQ ID NO 33
<211> LENGTH: 21
<212> TYPE: DNA
<213> ORGANISM: Artificial Sequence
<220> FEATURE:
<223> OTHER INFORMATION: antisense primer

<400> SEQUENCE: 33
ggagaaattg gtgtcgtgga a 21

<210> SEQ ID NO 34
<211> LENGTH: 21
<212> TYPE: DNA
<213> ORGANISM: Artificial Sequence
<220> FEATURE:
<223> OTHER INFORMATION: recombination site attB1 sequence

<400> SEQUENCE: 34
caagtttgta caaaaaagca g 21

<210> SEQ ID NO 35
<211> LENGTH: 21
<212> TYPE: DNA
<213> ORGANISM: Artificial Sequence
<220> FEATURE:
<223> OTHER INFORMATION: recombination site attB2 sequence

<400> SEQUENCE: 35
cagctttctt gtacaaagtg g 21

<210> SEQ ID NO 36
<211> LENGTH: 125
<212> TYPE: PRT
<213> ORGANISM: Glycine max

<400> SEQUENCE: 36

```
Met Ala Ser Ser Leu Leu Val Met Lys Val Thr Ser Cys Met Val Ala
1               5                   10                  15

Val Leu Met Val Ser Phe Gly His Ile Ile Pro Leu Ala Glu Ala Glu
            20                  25                  30

Ile Pro Cys Gly Arg Val Gln Ile Thr Val Ala Pro Cys Ile Gly Tyr
        35                  40                  45

Leu Arg Gly Pro Gly Gly Gly Val Pro Ala Ala Cys Cys Asn Gly Val
    50                  55                  60

Arg Ser Ile Asn Lys Glu Ala Lys Thr Thr Pro Asp Arg Gln Gly Val
65                  70                  75                  80

Cys Arg Cys Leu Lys Thr Thr Ala Leu Ser Leu Pro Gly Leu Asn Leu
                85                  90                  95

Ala Thr Leu Ala Ala Leu Pro Ser Lys Cys Gly Val Asn Leu Pro Tyr
            100                 105                 110

Lys Ile Ser Pro Thr Ile Asp Cys Asn Thr Val Lys His
        115                 120                 125
```

<210> SEQ ID NO 37
<211> LENGTH: 7499
<212> TYPE: DNA
<213> ORGANISM: Artificial
<220> FEATURE:
<223> OTHER INFORMATION: nucleotide sequence for QC258

<400> SEQUENCE: 37
ccgggatcca tggcccacag caagcacggc ctgaaggagg agatgaccat gaagtaccac 60
atggagggct gcgtgaacgg ccacaagttc gtgatcaccg gcgagggcat cggctacccc 120
ttcaagggca agcagaccat caacctgtgc gtgatcgagg gcggccccct gcccttcagc 180
gaggacatcc tgagcgccgg cttcaagtac ggcgaccgga tcttcaccga gtacccccag 240
gacatcgtgg actacttcaa gaacagctgc cccgccggct acacctgggg ccggagcttc 300

-continued

```
ctgttcgagg acggcgccgt gtgcatctgt aacgtggaca tcaccgtgag cgtgaaggag    360
aactgcatct accacaagag catcttcaac ggcgtgaact tccccgccga cggccccgtg    420
atgaagaaga tgaccaccaa ctgggaggcc agctgcgaga agatcatgcc cgtgcctaag    480
cagggcatcc tgaagggcga cgtgagcatg tacctgctgc tgaaggacgg cggccggtac    540
cggtgccagt tcgacaccgt gtacaaggcc aagagcgtgc ccagcaagat gcccgagtgg    600
cacttcatcc agcacaagct gctgcgggag gaccggagcg acgccaagaa ccagaagtgg    660
cagctgaccg agcacgccat cgccttcccc agcgccctgg cctgagagct cgaatttccc    720
cgatcgttca aacatttggc aataaagttt cttaagattg aatcctgttg ccggtcttgc    780
gatgattatc atataatttc tgttgaatta cgttaagcat gtaataatta acatgtaatg    840
catgacgtta tttatgagat gggtttttat gattagagtc ccgcaattat acatttaata    900
cgcgatagaa aacaaaatat agcgcgcaaa ctaggataaa ttatcgcgcg cggtgtcatc    960
tatgttacta gatcgggaat tctagtggcc ggcccagctg atgtaccggc gcgcccgatc   1020
atccggatat agttcctcct ttcagcaaaa aacccctcaa gacccgttta gaggccccaa   1080
ggggttatgc tagttattgc tcagcggtgg cagcagccaa ctcagcttcc tttcgggctt   1140
tgttagcagc cggatcgatc caagctgtac ctcactattc ctttgccctc ggacgagtgc   1200
tggggcgtcg gtttccacta tcggcgagta cttctacaca gccatcggtc cagacggccg   1260
cgcttctgcg ggcgatttgt gtacgcccga cagtcccggc tccggatcgg acgattgcgt   1320
cgcatcgacc ctgcgcccaa gctgcatcat cgaaattgcc gtcaaccaag ctctgataga   1380
gttggtcaag accaatgcgg agcatatacg cccggagccg cggcgatcct gcaagctccg   1440
gatgcctccg ctcgaagtag cgcgtctgct gctccataca agccaaccac ggcctccaga   1500
agaagatgtt ggcgacctcg tattgggaat ccccgaacat cgcctcgctc cagtcaatga   1560
ccgctgttat gcggccattg tccgtcagga cattgttgga gccgaaatcc gcgtgcacga   1620
ggtgccggac ttcggggcag tcctcggccc aaagcatcag ctcatcgaga gcctgcgcga   1680
cggacgcact gacggtgtcg tccatcacag tttgccagtg atacacatgg ggatcagcaa   1740
tcgcgcatat gaaatcacgc catgtagtgt attgaccgat tccttgcggt ccgaatgggc   1800
cgaacccgct cgtctggcta agatcggccg cagcgatcgc atccatagcc tccgcgaccg   1860
gctgcagaac agcgggcagt tcggtttcag gcaggtcttg caacgtgaca ccctgtgcac   1920
ggcgggagat gcaataggtc aggctctcgc tgaattcccc aatgtcaagc acttccggaa   1980
tcgggagcgc ggccgatgca aagtgccgat aaacataacg atctttgtag aaaccatcgg   2040
cgcagctatt tacccgcagg acatatccac gccctcctac atcgaagctg aaagcacgag   2100
attcttcgcc ctccgagagc tgcatcaggt cggagacgct gtcgaacttt tcgatcagaa   2160
acttctcgac agacgtcgcg gtgagttcag gcttttccat gggtatatct ccttcttaaa   2220
gttaaacaaa attatttcta gagggaaacc gttgtggtct ccctatagtg agtcgtatta   2280
atttcgcggg atcgagatct gatcaacctg cattaatgaa tcggccaacg cgcggggaga   2340
ggcggtttgc gtattgggcg ctcttccgct tcctcgctca ctgactcgct gcgctcggtc   2400
gttcggctgc ggcgagcggt atcagctcac tcaaaggcgg taatacggtt atccacagaa   2460
tcaggggata acgcaggaaa gaacatgtga gcaaaaggcc agcaaaaggc caggaaccgt   2520
aaaaaggccg cgttgctggc gtttttccat aggctccgcc cccctgacga gcatcacaaa   2580
aatcgacgct caagtcagag gtggcgaaac ccgacaggac tataaagata ccaggcgttt   2640
ccccctggaa gctccctcgt gcgctctcct gttccgaccc tgccgcttac cggatacctg   2700
```

tccgcctttc tcccttcggg aagcgtggcg ctttctcaat gctcacgctg taggtatctc 2760
agttcggtgt aggtcgttcg ctccaagctg ggctgtgtgc acgaaccccc cgttcagccc 2820
gaccgctgcg ccttatccgg taactatcgt cttgagtcca acccggtaag acacgactta 2880
tcgccactgg cagcagccac tggtaacagg attagcagag cgaggtatgt aggcggtgct 2940
acagagttct tgaagtggtg gcctaactac ggctacacta gaaggacagt atttggtatc 3000
tgcgctctgc tgaagccagt taccttcgga aaaagagttg gtagctcttg atccggcaaa 3060
caaaccaccg ctggtagcgg tggttttttt gtttgcaagc agcagattac gcgcagaaaa 3120
aaaggatctc aagaagatcc tttgatcttt tctacggggt ctgacgctca gtggaacgaa 3180
aactcacgtt aagggatttt ggtcatgaca ttaacctata aaaataggcg tatcacgagg 3240
ccctttcgtc tcgcgcgttt cggtgatgac ggtgaaaacc tctgacacat gcagctcccg 3300
gagacggtca cagcttgtct gtaagcggat gccgggagca gacaagcccg tcagggcgcg 3360
tcagcgggtg ttggcgggtg tcggggctgg cttaactatg cggcatcaga gcagattgta 3420
ctgagagtgc accatatgga catattgtcg ttagaacgcg gctacaatta atacataacc 3480
ttatgtatca tacacatacg atttaggtga cactatagaa cggcgcgcca agctgggtct 3540
agaactagaa acgtgatgcc acttgttatt gaagtcgatt acagcatcta ttctgtttta 3600
ctatttataa ctttgccatt tctgactttt gaaaactatc tctggatttc ggtatcgctt 3660
tgtgaagatc gagcaaaaga gacgttttgt ggacgcaatg gtccaaatcc gttctacatg 3720
aacaaattgg tcacaatttc cactaaaagt aaataaatgg caagttaaaa aaggaatatg 3780
cattttactg attgcctagg tgagctccaa gagaagttga atctacacgt ctaccaaccg 3840
ctaaaaaaag aaaaacattg aatatgtaac ctgattccat tagcttttga cttcttcaac 3900
agattctcta cttagatttc taacagaaat attattacta gcacatcatt ttcagtctca 3960
ctacagcaaa aaatccaacg gcacaataca gacaacagga gatatcagac tacagagata 4020
gatagatgct actgcatgta gtaagttaaa taaaaggaaa ataaaatgtc ttgctaccaa 4080
aactactaca gactatgatg ctcaccacag gccaaatcct gcaactagga cagcattatc 4140
ttatatatat tgtacaaaac aagcatcaag gaacatttgg tctaggcaat cagtacctcg 4200
ttctaccatc accctcagtt atcacatcct tgaaggatcc attactggga atcatcggca 4260
acacatgctc ctgatggggc acaatgacat caagaaggta ggggccaggg gtgtccaaca 4320
ttctctgaat tgccgctcta agctcttcct tcttcgtcac tcgcgctgcc ggtatcccac 4380
aagcatcagc aaacttgagc atgtttggga atatctcgct ctcgctagac ggatctccaa 4440
gataggtgtg agctctattg gacttgtaga acctatcctc caactgaacc accataccca 4500
aatgctgatt gttcaacaac aatatcttaa ctgggagatt ctccactctt atagtggcca 4560
actcctgaac attcatgatg aaactaccat ccccatcaat gtcaaccaca acagccccag 4620
ggttagcaac agcagcacca atagccgcag gcaatccaaa acccatggct ccaagacccc 4680
ctgaggtcaa ccactgcctc ggtctcttgt acttgtaaaa ctgcgcagcc cacatttgat 4740
gctgcccaac cccagtacta acaatagcat ctccattagt caactcatca agaacctcga 4800
tagcatgctg cggagaaatc gcgtcctgga atgtcttgta acccaatgga aacttgtgtt 4860
tctgcacatt aatctcttct ctccaacctc caagatcaaa cttaccctcc actcctttct 4920
cctccaaaat catattaatt cccttcaagg ccaacttcaa atccgcgcaa accgacacgt 4980
gcgcctgctt gttcttccca atctcggcag aatcaatatc aatgtgaaca atcttagccc 5040
tactagcaaa agcctcaagc ttcccagtaa cacggtcatc aaaccttacc ccaaaggcaa 5100
gcaacaaatc actattgtca acagcatagt tagcataaac agtaccatgc atacccagca 5160
tctgaaggga atattcatca ccaataggaa aagttccaag acccattaaa gtgctagcaa 5220
cgggaatacc agtgagttca acaaagcgcc tcaattcagc actggaattc aaactgccac 5280
cgccgacgta gagaacgggc ttttgggcct ccatgatgag tctgacaatg tgttccaatt 5340
gggcctcggc ggggggcctg ggcagcctgg cgaggtaacc ggggaggtta acgggctcgt 5400
cccaattagg cacggcgagt tgctgctgaa cgtctttggg aatgtcgatg aggaccggac 5460
cggggcggcc ggaggtggcg acgaagaaag cctcggcgac gacgcggggg atgtcgtcga 5520
cgtcgaggat gaggtagttg tgcttcgtga tggatctgct cacctccacg atcggggttt 5580
cttggaaggc gtcggtgccg atcatccggc gggcgacctg gccggtgatg gcgacgactg 5640
ggacgctgtc cattaaagcg tcggcgaggc cgctcacgag gttggtggcg ccggggccgg 5700
aggtggcaat gcagacgccg gggaggccgg aggaacgcgc gtagccttcg gcggcgaaga 5760
cgccgccctg ctcgtggcgc gggagcacgt tgcggatggc ggcggagcgc gtgagcgcct 5820
ggtggatctc catcgacgca ccgccggggt acgcgaacac cgtcgtcacg ccctgcctct 5880
ccagcgcctc cacaaggatg tccgcgccct tgcgaggttc gccggaggcg aaccgtgaca 5940
cgaagggctc cgtggtcggc gcttccttgg tgaagggcgc cgccgtgggg ggtttggaga 6000
tggaacattt gattttgaga gcgtggttgg gtttggtgag ggtttgatga gagagaggga 6060
gggtggatct agtaatgcgt ttggggaagg tggggtgtga agaggaagaa gagaatcggg 6120
tggttctgga agcggtggcc gccattgtgt tgtgtggcat ggttatactt caaaaactgc 6180
acaacaagcc tagagttagt acctaaacag taaatttaca acagagagca aagacacatg 6240
caaaaatttc agccataaaa aaagttataa tagaatttaa agcaaaagtt tcattttta 6300 aacatatata caaacaaact ggatttgaag gaagggatta attcccctgc tcaaagtttg 6360
aattcctatt gtgacctata ctcgaataaa attgaagcct aaggaatgta tgagaaacaa 6420
gaaaacaaaa caaaactaca gacaaacaag tacaattaca aaattcgcta aaattctgta 6480
atcaccaaac cccatctcag tcagcacaag gcccaaggtt tattttgaaa taaaaaaaaa 6540
gtgattttat ttctcataag ctaaaagaaa gaaaggcaat tatgaaatga tttcgactag 6600
atctgaaagt caaacgcgta ttccgcagat attaaagaaa gagtagagtt tcacatggat 6660
cctagatgga cccagttgag gaaaaagcaa ggcaaagcaa accagaagtg caagatccga 6720
aattgaacca cggaatctag gatttggtag agggagaaga aaagtacctt gagaggtaga 6780
agagaagaga agagcagaga gatatatgaa cgagtgtgtc ttggtctcaa ctctgaagcg 6840
atacgagttt agaggggagc attgagttcc aatttatagg gaaaccgggt ggcaggggtg 6900
agttaatgac ggaaaagccc ctaagtaacg agattggatt gtgggttaga ttcaaccgtt 6960
tgcatccgcg gcttagattg gggaagtcag agtgaatctc aaccgttgac tgagttgaaa 7020
attgaatgta gcaaccaatt gagccaaccc cagcctttgc cctttgattt tgatttgttt 7080
gttgcatact ttttatttgt cttctggttc tgactctctt tctctcgttt caatgccagg 7140
ttgcctactc ccacaccact cacaagaaga ttctactgtt agtattaaat attttttaat 7200
gtattaaatg atgaatgctt ttgtaaacag aacaagacta tgtctaataa gtgtcttgca 7260 acattttttta agaaattaaa aaaaatatat ttattatcaa aatcaaatgt atgaaaaatc 7320
atgaataata taattttata catttttttta aaaaatcttt taatttctta attaatatct 7380
taaaaataat gattaatatt taacccaaaa taattagtat gattggtaag gaagatatcc 7440
atgttatgtt tggatgtgag tttgatctag agcaaagctt actagagtcg acctgcagc 7499

-continued

<210> SEQ ID NO 38
<211> LENGTH: 2817
<212> TYPE: DNA
<213> ORGANISM: Artificial
<220> FEATURE:
<223> OTHER INFORMATION: nucleotide sequence for pCR8/GW/TOPO

<400> SEQUENCE: 38

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggctcc gaattcgccc ttaagggcga attcgaccca gctttcttgt acaaagttgg    720
cattataaaa aataattgct catcaatttg ttgcaacgaa caggtcacta tcagtcaaaa    780
taaaatcatt atttgccatc cagctgatat cccctatagt gagtcgtatt acatggtcat    840
agctgtttcc tggcagctct ggcccgtgtc tcaaaatctc tgatgttaca ttgcacaaga    900
taaaaatata tcatcatgcc tcctctagac cagccaggac agaaatgcct cgacttcgct    960
gctgcccaag gttgccgggt gacgcacacc gtggaaacgg atgaaggcac gaacccagtg   1020
gacataagcc tgttcggttc gtaagctgta atgcaagtag cgtatgcgct cacgcaactg   1080
gtccagaacc ttgaccgaac gcagcggtgg taacggcgca gtggcggttt tcatggcttg   1140
ttatgactgt ttttttgggg tacagtctat gcctcgggca tccaagcagc aagcgcgtta   1200
cgccgtgggt cgatgtttga tgttatggag cagcaacgat gttacgcagc agggcagtcg   1260
ccctaaaaca aagttaaaca tcatgaggga agcggtgatc gccgaagtat cgactcaact   1320
atcagaggta gttggcgtca tcgagcgcca tctcgaaccg acgttgctgg ccgtacattt   1380
gtacggctcc gcagtggatg gcggcctgaa gccacacagt gatattgatt tgctggttac   1440
ggtgaccgta aggcttgatg aaacaacgcg gcgagctttg atcaacgacc ttttggaaac   1500
ttcggcttcc cctggagaga gcgagattct ccgcgctgta gaagtcacca ttgttgtgca   1560
cgacgacatc attccgtggc gttatccagc taagcgcgaa ctgcaatttg gagaatggca   1620
gcgcaatgac attcttgcag gtatcttcga gccagccacg atcgacattg atctggctat   1680
cttgctgaca aaagcaagag aacatagcgt tgccttggta ggtccagcgg cggaggaact   1740
ctttgatccg gttcctgaac aggatctatt tgaggcgcta aatgaaacct taacgctatg   1800
gaactcgccg cccgactggg ctggcgatga gcgaaatgta gtgcttacgt tgtcccgcat   1860
ttggtacagc gcagtaaccg gcaaaatcgc gccgaaggat gtcgctgccg actgggcaat   1920
ggagcgcctg ccggcccagt atcagcccgt catacttgaa gctagacagg cttatcttgg   1980
acaagaagaa gatcgcttgg cctcgcgcgc agatcagttg gaagaatttg tccactacgt   2040
gaaaggcgag atcaccaagg tagtcggcaa ataaccctcg agccacccat gaccaaaatc   2100
```

```
ccttaacgtg agttacgcgt cgttccactg agcgtcagac cccgtagaaa agatcaaagg   2160

atcttcttga gatccttttt ttctgcgcgt aatctgctgc ttgcaaacaa aaaaaccacc   2220

gctaccagcg gtggtttgtt tgccggatca agagctacca actctttttc cgaaggtaac   2280

tggcttcagc agagcgcaga taccaaatac tgtccttcta gtgtagccgt agttaggcca   2340

ccacttcaag aactctgtag caccgcctac atacctcgct ctgctaatcc tgttaccagt   2400

ggctgctgcc agtggcgata agtcgtgtct taccgggttg gactcaagac gatagttacc   2460

ggataaggcg cagcggtcgg gctgaacggg gggttcgtgc acacagccca gcttggagcg   2520

aacgacctac accgaactga gatacctaca gcgtgagcat tgagaaagcg ccacgcttcc   2580

cgaagggaga aaggcggaca ggtatccggt aagcggcagg gtcggaacag gagagcgcac   2640

gagggagctt ccagggggaa acgcctggta tctttatagt cctgtcgggt ttcgccacct   2700

ctgacttgag cgtcgatttt tgtgatgctc gtcagggggg cggagcctat ggaaaaacgc   2760

cagcaacgcg gcctttttac ggttcctggc cttttgctgg ccttttgctc acatgtt      2817
```

```
<210> SEQ ID NO 39
<211> LENGTH: 3953
<212> TYPE: DNA
<213> ORGANISM: Artificial
<220> FEATURE:
<223> OTHER INFORMATION: nucleotide sequence for QC267-1

<400> SEQUENCE: 39

gggtcctact cctactcgac aatattctaa tttctaagac atatgtttta tctgtttttg     60

tttttcagtt tttaaaacac ttgttttgaa aattattttc aaaacataat aaaatagaaa    120

gttacaaaat ggtaaagaaa aaactgagaa gaaaaacaac catgagttta atttttggta    180

aagaagtagt ttatatatcg ttggctttat acgaatataa cgaaaacacc gagtgaaaaa    240

atgttacgca gaaaagagat agatagaatg agaagagaga aaatataaca gattcgatat    300

aaaatacaaa gatatagaaa tgataatgtc gtagaaaatg ttatatgaat aagtgatcta    360

acacagaaaa aagaaagaag tgagttaatt agacaaaaag agaagaaact tgtgttttga    420

gaacaaaatt gtaacgaata atcaaacact aaaatgaaca atactcagtt acttacgatg    480

acttgaacga tgtcggcaga agtgggaaat aataaaaagt aagtccatac aaaataacgt    540

gccaaattca ttttgggtga tgcagaaacc tgccaaacca catggckata tatatatata    600

gaaacagttg atcagttagc aaccctttgc caactctgat atattatgta ttttttttta    660

tgttttagtt attttatttt attttattca aaattttaat attttaaaat ttaaaatcta    720

actaatgtat tttttaaaat atattcttat ttaatattca cgtgataaaa tataaaatat    780

aaaatatcaa tatattaaat aagaatattt taattcaaat ataatatttt ttaattttat    840

taaatattta ttaattcata tataatatta aggtataaac tcattaattg tatcacgttg    900

taggtttgag catgcggtta ttcaattgct tgcattaaat gaaatcaacc aggaactagc    960

tatcattcct tagttcactt ttcacttaac gaactcaayc agctggctga atctgaactc   1020

tatatatagt ccttaaattc acaaatcata acatcaaaac catcacttca tactcactag   1080

tcactatagc tcacccttga agaagtgcaa tttcatcctc taactcttcc aaatccaagg   1140

gcgaattcga cccagctttc ttgtacaaag ttggcattat aaaaaataat tgctcatcaa   1200

tttgttgcaa cgaacaggtc actatcagtc aaaataaaat cattatttgc catccagctg   1260

atatccccta tagtgagtcg tattacatgg tcatagctgt ttcctggcag ctctggcccg   1320

tgtctcaaaa tctctgatgt tacattgcac aagataaaaa tatatcatca tgcctcctct   1380
```

```
agaccagcca ggacagaaat gcctcgactt cgctgctgcc caaggttgcc gggtgacgca   1440
caccgtggaa acggatgaag gcacgaaccc agtggacata agcctgttcg gttcgtaagc   1500
tgtaatgcaa gtagcgtatg cgctcacgca actggtccag aaccttgacc gaacgcagcg   1560
gtggtaacgg cgcagtggcg gttttcatgg cttgttatga ctgttttttt ggggtacagt   1620
ctatgcctcg ggcatccaag cagcaagcgc gttacgccgt gggtcgatgt ttgatgttat   1680
ggagcagcaa cgatgttacg cagcagggca gtcgccctaa aacaaagtta aacatcatga   1740
gggaagcggt gatcgccgaa gtatcgactc aactatcaga ggtagttggc gtcatcgagc   1800
gccatctcga accgacgttg ctggccgtac atttgtacgg ctccgcagtg gatggcggcc   1860
tgaagccaca cagtgatatt gatttgctgg ttacggtgac cgtaaggctt gatgaaacaa   1920
cgcggcgagc tttgatcaac gaccttttgg aaacttcggc ttcccctgga gagagcgaga   1980
ttctccgcgc tgtagaagtc accattgttg tgcacgacga catcattccg tggcgttatc   2040
cagctaagcg cgaactgcaa tttggagaat ggcagcgcaa tgacattctt gcaggtatct   2100
tcgagccagc cacgatcgac attgatctgg ctatcttgct gacaaaagca agagaacata   2160
gcgttgcctt ggtaggtcca gcggcggagg aactctttga tccggttcct gaacaggatc   2220
tatttgaggc gctaaatgaa accttaacgc tatggaactc gccgcccgac tgggctggcg   2280
atgagcgaaa tgtagtgctt acgttgtccc gcatttggta cagcgcagta accggcaaaa   2340
tcgcgccgaa ggatgtcgct gccgactggg caatggagcg cctgccggcc cagtatcagc   2400
ccgtcatact tgaagctaga caggcttatc ttggacaaga agaagatcgc ttggcctcgc   2460
gcgcagatca gttggaagaa tttgtccact acgtgaaagg cgagatcacc aaggtagtcg   2520
gcaaataacc ctcgagccac ccatgaccaa aatcccttaa cgtgagttac gcgtcgttcc   2580
actgagcgtc agaccccgta gaaaagatca aaggatcttc ttgagatcct ttttttctgc   2640
gcgtaatctg ctgcttgcaa acaaaaaaac caccgctacc agcggtggtt tgtttgccgg   2700
atcaagagct accaactctt tttccgaagg taactggctt cagcagagcg cagataccaa   2760
atactgtcct tctagtgtag ccgtagttag gccaccactt caagaactct gtagcaccgc   2820
ctacatacct cgctctgcta atcctgttac cagtggctgc tgccagtggc gataagtcgt   2880
gtcttaccgg gttggactca agacgatagt taccggataa ggcgcagcgg tcgggctgaa   2940
cggggggttc gtgcacacag cccagcttgg agcgaacgac ctacaccgaa ctgagatacc   3000
tacagcgtga gcattgagaa agcgccacgc ttcccgaagg gagaaaggcg gacaggtatc   3060
cggtaagcgg cagggtcgga acaggagagc gcacgaggga gcttccaggg ggaaacgcct   3120
ggtatcttta tagtcctgtc gggtttcgcc acctctgact tgagcgtcga tttttgtgat   3180
gctcgtcagg ggggcggagc ctatggaaaa acgccagcaa cgcggccttt ttacggttcc   3240
tggccttttg ctggcctttt gctcacatgt tctttcctgc gttatcccct gattctgtgg   3300
ataaccgtat taccgccttt gagtgagctg ataccgctcg ccgcagccga acgaccgagc   3360
gcagcgagtc agtgagcgag gaagcggaag agcgcccaat acgcaaaccg cctctccccg   3420
cgcgttggcc gattcattaa tgcagctggc acgacaggtt tcccgactgg aaagcgggca   3480
gtgagcgcaa cgcaattaat acgcgtaccg ctagccagga agagtttgta gaaacgcaaa   3540
aaggccatcc gtcaggatgg ccttctgctt agtttgatgc ctggcagttt atggcgggcg   3600
tcctgcccgc caccctccgg gccgttgctt cacaacgttc aaatccgctc ccggcggatt   3660
tgtcctactc aggagagcgt tcaccgacaa acaacagata aaacgaaagg cccagtcttc   3720
cgactgagcc tttcgtttta tttgatgcct ggcagttccc tactctcgcg ttaacgctag   3780
```

catggatgtt ttcccagtca cgacgttgta aaacgacggc cagtcttaag ctcgggcccc 3840
aaataatgat tttattttga ctgatagtga cctgttcgtt gcaacaaatt gatgagcaat 3900 gctttttat aatgccaact ttgtacaaaa aagcaggctc cgaattcgcc ctt 3953

<210> SEQ ID NO 40
<211> LENGTH: 3744
<212> TYPE: DNA
<213> ORGANISM: Artificial
<220> FEATURE:
<223> OTHER INFORMATION: nucleotide sequence for QC267-2

<400> SEQUENCE: 40
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg ctttttata atgccaactt tgtacaaaaa 660
agcaggctcc gaattcgccc tttacgaata taacgaaaac accgagtgaa aaaatgttac 720
gcagaaaaga gatagataga atgagaagag agaaaatata acagattcga tataaaatac 780
aaagatatag aaatgataat gtcgtagaaa atgttatatg aataagtgat ctaacacaga 840
aaaaagaaag aagtgagtta attagacaaa aagagaagaa acttgtgttt tgagaacaaa 900
attgtaacga ataatcaaac actaaaatga acaatactca gttacttacg atgacttgaa 960
cgatgtcggc agaagtggga aataataaaa agtaagtcca tacaaaataa cgtgccaaat 1020
tcattttggg tgatgcagaa acctgccaaa ccacatggck atatatatat atagaaacag 1080
ttgatcagtt agcaaccctt tgccaactct gatatattat gtattttttt ttatgtttta 1140
gttattttat tttattttat tcaaaatttt aatattttaa aatttaaaat ctaactaatg 1200
tattttttaa aatatattct tatttaatat tcacgtgata aaatataaaa tataaaatat 1260
caatatatta aataagaata ttttaattca aatataatat tttttaattt tattaaatat 1320
ttattaattc atatataata ttaaggtata aactcattaa ttgtatcacg ttgtaggttt 1380
gagcatgcgg ttattcaatt gcttgcatta aatgaaatca accaggaact agctatcatt 1440
ccttagttca cttttcactt aacgaactca aycagctggc tgaatctgaa ctctatatat 1500
agtccttaaa ttcacaaatc ataacatcaa aaccatcact tcatactcac tagtcactat 1560
agctcaccct tgaagaagtg caatttcatc ctctaactct tccaaatcca agggcgaatt 1620
cgacccagct ttcttgtaca aagttggcat tataaaaaat aattgctcat caatttgttg 1680
caacgaacag gtcactatca gtcaaaataa aatcattatt tgccatccag ctgatatccc 1740
ctatagtgag tcgtattaca tggtcatagc tgtttcctgg cagctctggc ccgtgtctca 1800
aaatctctga tgttacattg cacaagataa aaatatatca tcatgcctcc tctagaccag 1860
ccaggacaga aatgcctcga cttcgctgct gcccaaggtt gccgggtgac gcacaccgtg 1920
gaaacggatg aaggcacgaa cccagtggac ataagcctgt tcggttcgta agctgtaatg 1980
caagtagcgt atgcgctcac gcaactggtc cagaaccttg accgaacgca gcggtggtaa 2040
cggcgcagtg gcggttttca tggcttgtta tgactgtttt tttggggtac agtctatgcc 2100
tcgggcatcc aagcagcaag cgcgttacgc cgtgggtcga tgtttgatgt tatggagcag 2160
caacgatgtt acgcagcagg gcagtcgccc taaaacaaag ttaaacatca tgagggaagc 2220
ggtgatcgcc gaagtatcga ctcaactatc agaggtagtt ggcgtcatcg agcgccatct 2280
cgaaccgacg ttgctggccg tacatttgta cggctccgca gtggatggcg gcctgaagcc 2340
acacagtgat attgatttgc tggttacggt gaccgtaagg cttgatgaaa caacgcggcg 2400
agctttgatc aacgaccttt tggaaacttc ggcttcccct ggagagagcg agattctccg 2460
cgctgtagaa gtcaccattg ttgtgcacga cgacatcatt ccgtggcgtt atccagctaa 2520
gcgcgaactg caatttggag aatggcagcg caatgacatt cttgcaggta tcttcgagcc 2580
agccacgatc gacattgatc tggctatctt gctgacaaaa gcaagagaac atagcgttgc 2640
cttggtaggt ccagcggcgg aggaactctt tgatccggtt cctgaacagg atctatttga 2700
ggcgctaaat gaaaccttaa cgctatggaa ctcgccgccc gactgggctg gcgatgagcg 2760
aaatgtagtg cttacgttgt cccgcatttg gtacagcgca gtaaccggca aaatcgcgcc 2820
gaaggatgtc gctgccgact gggcaatgga gcgcctgccg gcccagtatc agcccgtcat 2880
acttgaagct agacaggctt atcttggaca agaagaagat cgcttggcct cgcgcgcaga 2940
tcagttggaa gaatttgtcc actacgtgaa aggcgagatc accaaggtag tcggcaaata 3000
accctcgagc cacccatgac caaaatccct taacgtgagt tacgcgtcgt tccactgagc 3060
gtcagacccc gtagaaaaga tcaaaggatc ttcttgagat cctttttttc tgcgcgtaat 3120
ctgctgcttg caaacaaaaa aaccaccgct accagcggtg gtttgtttgc cggatcaaga 3180
gctaccaact ctttttccga aggtaactgg cttcagcaga gcgcagatac caaatactgt 3240
ccttctagtg tagccgtagt taggccacca cttcaagaac tctgtagcac cgcctacata 3300
cctcgctctg ctaatcctgt taccagtggc tgctgccagt ggcgataagt cgtgtcttac 3360
cgggttggac tcaagacgat agttaccgga taaggcgcag cggtcgggct gaacgggggg 3420
ttcgtgcaca cagcccagct tggagcgaac gacctacacc gaactgagat acctacagcg 3480
tgagcattga gaaagcgcca cgcttcccga agggagaaag gcggacaggt atccggtaag 3540
cggcagggtc ggaacaggag agcgcacgag ggagcttcca gggggaaacg cctggtatct 3600
ttatagtcct gtcgggtttc gccacctctg acttgagcgt cgatttttgt gatgctcgtc 3660
aggggggcgg agcctatgga aaaacgccag caacgcggcc tttttacggt tcctggcctt 3720
ttgctggcct tttgctcaca tgtt 3744

<210> SEQ ID NO 41
<211> LENGTH: 3555
<212> TYPE: DNA
<213> ORGANISM: Artificial
<220> FEATURE:
<223> OTHER INFORMATION: nucleotide sequence for QC267-3

<400> SEQUENCE: 41
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240

```
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg ctttttata atgccaactt tgtacaaaaa     660
agcaggctcc gaattcgccc ttagagaaga aacttgtgtt ttgagaacaa aattgtaacg    720
aataatcaaa cactaaaatg aacaatactc agttacttac gatgacttga acgatgtcgg    780
cagaagtggg aaataataaa aagtaagtcc atacaaaata acgtgccaaa ttcattttgg    840
gtgatgcaga aacctgccaa accacatggc katatatata tatagaaaca gttgatcagt    900
tagcaaccct ttgccaactc tgatatatta tgtatttttt tttatgtttt agttatttta    960
ttttatttta ttcaaaattt taatatttta aaatttaaaa tctaactaat gtatttttta   1020
aaatatattc ttatttaata ttcacgtgat aaaatataaa atataaaata tcaatatatt   1080
aaataagaat attttaattc aaatataata ttttttaatt ttattaaata tttattaatt   1140
catatataat attaaggtat aaactcatta attgtatcac gttgtaggtt tgagcatgcg   1200
gttattcaat tgcttgcatt aaatgaaatc aaccaggaac tagctatcat tccttagttc   1260
acttttcact taacgaactc aaycagctgg ctgaatctga actctatata tagtccttaa   1320
attcacaaat cataacatca aaaccatcac ttcatactca ctagtcacta tagctcaccc   1380
ttgaagaagt gcaatttcat cctctaactc ttccaaatcc aagggcgaat tcgacccagc   1440
tttcttgtac aaagttggca ttataaaaaa taattgctca tcaatttgtt gcaacgaaca   1500
ggtcactatc agtcaaaata aaatcattat ttgccatcca gctgatatcc cctatagtga   1560
gtcgtattac atggtcatag ctgtttcctg gcagctctgg cccgtgtctc aaaatctctg   1620
atgttacatt gcacaagata aaaatatatc atcatgcctc ctctagacca gccaggacag   1680
aaatgcctcg acttcgctgc tgcccaaggt tgccgggtga cgcacaccgt ggaaacggat   1740
gaaggcacga acccagtgga cataagcctg ttcggttcgt aagctgtaat gcaagtagcg   1800
tatgcgctca cgcaactggt ccagaacctt gaccgaacgc agcggtggta acggcgcagt   1860
ggcggttttc atggcttgtt atgactgttt ttttggggta cagtctatgc ctcgggcatc   1920
caagcagcaa gcgcgttacg ccgtgggtcg atgtttgatg ttatggagca gcaacgatgt   1980
tacgcagcag ggcagtcgcc ctaaaacaaa gttaaacatc atgagggaag cggtgatcgc   2040
cgaagtatcg actcaactat cagaggtagt tggcgtcatc gagcgccatc tcgaaccgac   2100
gttgctggcc gtacatttgt acggctccgc agtggatggc ggcctgaagc cacacagtga   2160
tattgatttg ctggttacgg tgaccgtaag gcttgatgaa acaacgcggc gagctttgat   2220
caacgacctt ttggaaactt cggcttcccc tggagagagc gagattctcc gcgctgtaga   2280
agtcaccatt gttgtgcacg acgacatcat tccgtggcgt tatccagcta agcgcgaact   2340
gcaatttgga gaatggcagc gcaatgacat tcttgcaggt atcttcgagc cagccacgat   2400
cgacattgat ctggctatct tgctgacaaa agcaagagaa catagcgttg ccttggtagg   2460
tccagcggcg gaggaactct ttgatccggt tcctgaacag gatctatttg aggcgctaaa   2520
tgaaacctta acgctatgga actcgccgcc cgactgggct ggcgatgagc gaaatgtagt   2580
gcttacgttg tcccgcattt ggtacagcgc agtaaccggc aaaatcgcgc cgaaggatgt   2640
```

```
cgctgccgac tgggcaatgg agcgcctgcc ggcccagtat cagcccgtca tacttgaagc   2700
tagacaggct tatcttggac aagaagaaga tcgcttggcc tcgcgcgcag atcagttgga   2760
agaatttgtc cactacgtga aaggcgagat caccaaggta gtcggcaaat aaccctcgag   2820
ccacccatga ccaaaatccc ttaacgtgag ttacgcgtcg ttccactgag cgtcagaccc   2880
cgtagaaaag atcaaaggat cttcttgaga tccttttttt ctgcgcgtaa tctgctgctt   2940
gcaaacaaaa aaaccaccgc taccagcggt ggtttgtttg ccggatcaag agctaccaac   3000
tctttttccg aaggtaactg gcttcagcag agcgcagata ccaaatactg tccttctagt   3060
gtagccgtag ttaggccacc acttcaagaa ctctgtagca ccgcctacat acctcgctct   3120
gctaatcctg ttaccagtgg ctgctgccag tggcgataag tcgtgtctta ccgggttgga   3180
ctcaagacga tagttaccgg ataaggcgca gcggtcgggc tgaacggggg gttcgtgcac   3240
acagcccagc ttggagcgaa cgacctacac cgaactgaga tacctacagc gtgagcattg   3300
agaaagcgcc acgcttcccg aagggagaaa ggcggacagg tatccggtaa gcggcagggt   3360
cggaacagga gagcgcacga gggagcttcc agggggaaac gcctggtatc tttatagtcc   3420
tgtcgggttt cgccacctct gacttgagcg tcgatttttg tgatgctcgt caggggggcg   3480
gagcctatgg aaaaacgcca gcaacgcggc ctttttacgg ttcctggcct tttgctggcc   3540
ttttgctcac atgtt                                                    3555
```

<210> SEQ ID NO 42
<211> LENGTH: 3344
<212> TYPE: DNA
<213> ORGANISM: Artificial
<220> FEATURE:
<223> OTHER INFORMATION: nucleotide sequence for QC267-4

<400> SEQUENCE: 42

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggctcc gaattcgccc ttgatcagtt agcaaccctt tgccaactct gatatattat    720
gtattttttt ttatgtttta gttattttat tttattttat tcaaaatttt aatattttaa    780
aatttaaaat ctaactaatg tattttttaa aatatattct tatttaatat tcacgtgata    840
aaatataaaa tataaaatat caatatatta aataagaata ttttaattca aatataatat    900
tttttaattt tattaaatat ttattaattc atatataata ttaaggtata aactcattaa    960
ttgtatcacg ttgtaggttt gagcatgcgg ttattcaatt gcttgcatta aatgaaatca   1020
accaggaact agctatcatt ccttagttca cttttcactt aacgaactca aycagctggc   1080
tgaatctgaa ctctatatat agtccttaaa ttcacaaatc ataacatcaa aaccatcact   1140
```

-continued

```
tcatactcac tagtcactat agctcaccct tgaagaagtg caatttcatc ctctaactct   1200

tccaaatcca agggcgaatt cgacccagct ttcttgtaca aagttggcat tataaaaaat   1260

aattgctcat caatttgttg caacgaacag gtcactatca gtcaaaataa aatcattatt   1320

tgccatccag ctgatatccc ctatagtgag tcgtattaca tggtcatagc tgtttcctgg   1380

cagctctggc ccgtgtctca aaatctctga tgttacattg cacaagataa aaatatatca   1440

tcatgcctcc tctagaccag ccaggacaga aatgcctcga cttcgctgct gcccaaggtt   1500

gccgggtgac gcacaccgtg gaaacggatg aaggcacgaa cccagtggac ataagcctgt   1560

tcggttcgta agctgtaatg caagtagcgt atgcgctcac gcaactggtc cagaaccttg   1620

accgaacgca gcggtggtaa cggcgcagtg gcggttttca tggcttgtta tgactgtttt   1680

tttggggtac agtctatgcc tcgggcatcc aagcagcaag cgcgttacgc cgtgggtcga   1740

tgtttgatgt tatggagcag caacgatgtt acgcagcagg gcagtcgccc taaaacaaag   1800

ttaaacatca tgagggaagc ggtgatcgcc gaagtatcga ctcaactatc agaggtagtt   1860

ggcgtcatcg agcgccatct cgaaccgacg ttgctggccg tacatttgta cggctccgca   1920

gtggatggcg gcctgaagcc acacagtgat attgatttgc tggttacggt gaccgtaagg   1980

cttgatgaaa caacgcggcg agctttgatc aacgaccttt tggaaacttc ggcttcccct   2040

ggagagagcg agattctccg cgctgtagaa gtcaccattg ttgtgcacga cgacatcatt   2100

ccgtggcgtt atccagctaa gcgcgaactg caatttggag aatggcagcg caatgacatt   2160

cttgcaggta tcttcgagcc agccacgatc gacattgatc tggctatctt gctgacaaaa   2220

gcaagagaac atagcgttgc cttggtaggt ccagcggcgg aggaactctt tgatccggtt   2280

cctgaacagg atctatttga ggcgctaaat gaaaccttaa cgctatggaa ctcgccgccc   2340

gactgggctg gcgatgagcg aaatgtagtg cttacgttgt cccgcatttg gtacagcgca   2400

gtaaccggca aaatcgcgcc gaaggatgtc gctgccgact gggcaatgga gcgcctgccg   2460

gcccagtatc agcccgtcat acttgaagct agacaggctt atcttggaca agaagaagat   2520

cgcttggcct cgcgcgcaga tcagttggaa gaatttgtcc actacgtgaa aggcgagatc   2580

accaaggtag tcggcaaata accctcgagc cacccatgac caaaatccct taacgtgagt   2640

tacgcgtcgt tccactgagc gtcagacccc gtagaaaaga tcaaaggatc ttcttgagat   2700

cctttttttc tgcgcgtaat ctgctgcttg caaacaaaaa aaccaccgct accagcggtg   2760

gtttgtttgc cggatcaaga gctaccaact ctttttccga aggtaactgg cttcagcaga   2820

gcgcagatac caaatactgt ccttctagtg tagccgtagt taggccacca cttcaagaac   2880

tctgtagcac cgcctacata cctcgctctg ctaatcctgt taccagtggc tgctgccagt   2940

ggcgataagt cgtgtcttac cgggttggac tcaagacgat agttaccgga taaggcgcag   3000

cggtcgggct gaacgggggg ttcgtgcaca cagcccagct tggagcgaac gacctacacc   3060

gaactgagat acctacagcg tgagcattga gaaagcgcca cgcttcccga agggagaaag   3120

gcggacaggt atccggtaag cggcagggtc ggaacaggag agcgcacgag ggagcttcca   3180

gggggaaacg cctggtatct ttatagtcct gtcgggtttc gccacctctg acttgagcgt   3240

cgatttttgt gatgctcgtc aggggggcgg agcctatgga aaaacgccag caacgcggcc   3300

tttttacggt tcctggcctt ttgctggcct tttgctcaca tgtt                    3344
```

<210> SEQ ID NO 43
<211> LENGTH: 3074
<212> TYPE: DNA
<213> ORGANISM: Artificial
<220> FEATURE:
<223> OTHER INFORMATION: nucleotide sequence for QC267-5

<400> SEQUENCE: 43
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggctcc gaattcgccc ttctcattaa ttgtatcacg ttgtaggttt gagcatgcgg 720
ttattcaatt gcttgcatta aatgaaatca accaggaact agctatcatt ccttagttca 780
cttttcactt aacgaactca aycagctggc tgaatctgaa ctctatatat agtccttaaa 840
ttcacaaatc ataacatcaa aaccatcact tcatactcac tagtcactat agctcaccct 900
tgaagaagtg caatttcatc ctctaactct tccaaatcca agggcgaatt cgacccagct 960
ttcttgtaca aagttggcat tataaaaaat aattgctcat caatttgttg caacgaacag 1020
gtcactatca gtcaaaataa aatcattatt tgccatccag ctgatatccc ctatagtgag 1080
tcgtattaca tggtcatagc tgtttcctgg cagctctggc ccgtgtctca aaatctctga 1140
tgttacattg cacaagataa aaatatatca tcatgcctcc tctagaccag ccaggacaga 1200
aatgcctcga cttcgctgct gcccaaggtt gccgggtgac gcacaccgtg gaaacggatg 1260
aaggcacgaa cccagtggac ataagcctgt tcggttcgta agctgtaatg caagtagcgt 1320
atgcgctcac gcaactggtc cagaaccttg accgaacgca gcggtggtaa cggcgcagtg 1380
gcggttttca tggcttgtta tgactgtttt tttggggtac agtctatgcc tcgggcatcc 1440
aagcagcaag cgcgttacgc cgtgggtcga tgtttgatgt tatggagcag caacgatgtt 1500
acgcagcagg gcagtcgccc taaaacaaag ttaaacatca tgagggaagc ggtgatcgcc 1560
gaagtatcga ctcaactatc agaggtagtt ggcgtcatcg agcgccatct cgaaccgacg 1620
ttgctggccg tacatttgta cggctccgca gtggatggcg gcctgaagcc acacagtgat 1680
attgatttgc tggttacggt gaccgtaagg cttgatgaaa caacgcggcg agctttgatc 1740
aacgaccttt tggaaacttc ggcttcccct ggagagagcg agattctccg cgctgtagaa 1800
gtcaccattg ttgtgcacga cgacatcatt ccgtggcgtt atccagctaa gcgcgaactg 1860
caatttggag aatggcagcg caatgacatt cttgcaggta tcttcgagcc agccacgatc 1920
gacattgatc tggctatctt gctgacaaaa gcaagagaac atagcgttgc cttggtaggt 1980
ccagcggcgg aggaactctt tgatccggtt cctgaacagg atctatttga ggcgctaaat 2040
gaaaccttaa cgctatggaa ctcgccgccc gactgggctg gcgatgagcg aaatgtagtg 2100
cttacgttgt cccgcatttg gtacagcgca gtaaccggca aaatcgcgcc gaaggatgtc 2160
gctgccgact gggcaatgga gcgcctgccg gcccagtatc agcccgtcat acttgaagct 2220
agacaggctt atcttggaca agaagaagat cgcttggcct cgcgcgcaga tcagttggaa 2280

-continued

```
gaatttgtcc actacgtgaa aggcgagatc accaaggtag tcggcaaata accctcgagc   2340

cacccatgac caaaatccct taacgtgagt tacgcgtcgt tccactgagc gtcagacccc   2400

gtagaaaaga tcaaaggatc ttcttgagat cctttttttc tgcgcgtaat ctgctgcttg   2460

caaacaaaaa aaccaccgct accagcggtg gtttgtttgc cggatcaaga gctaccaact   2520

ctttttccga aggtaactgg cttcagcaga gcgcagatac caaatactgt ccttctagtg   2580

tagccgtagt taggccacca cttcaagaac tctgtagcac cgcctacata cctcgctctg   2640

ctaatcctgt taccagtggc tgctgccagt ggcgataagt cgtgtcttac cgggttggac   2700

tcaagacgat agttaccgga taaggcgcag cggtcgggct gaacgggggg ttcgtgcaca   2760

cagcccagct tggagcgaac gacctacacc gaactgagat acctacagcg tgagcattga   2820

gaaagcgcca cgcttcccga agggagaaag gcggacaggt atccggtaag cggcagggtc   2880

ggaacaggag agcgcacgag ggagcttcca gggggaaacg cctggtatct ttatagtcct   2940

gtcgggtttc gccacctctg acttgagcgt cgatttttgt gatgctcgtc aggggggcgg   3000

agcctatgga aaaacgccag caacgcggcc tttttacggt tcctggcctt ttgctggcct   3060

tttgctcaca tgtt                                                     3074
```

<210> SEQ ID NO 44
<211> LENGTH: 4585
<212> TYPE: DNA
<213> ORGANISM: Artificial
<220> FEATURE:
<223> OTHER INFORMATION: nucleotide sequence for QC267-2Y

<400> SEQUENCE: 44

```
cttgtacaaa gtggttgatg ggatccatgg cccacagcaa gcacggcctg aaggaggaga     60

tgaccatgaa gtaccacatg gagggctgcg tgaacggcca caagttcgtg atcaccggcg    120

agggcatcgg ctaccccttc aagggcaagc agaccatcaa cctgtgcgtg atcgagggcg    180

gcccccctgcc cttcagcgag gacatcctga gcgccggctt caagtacggc gaccggatct    240

tcaccgagta cccccaggac atcgtggact acttcaagaa cagctgcccc gccggctaca    300

cctggggccg gagcttcctg ttcgaggacg gcgccgtgtg catctgtaac gtggacatca    360

ccgtgagcgt gaaggagaac tgcatctacc acaagagcat cttcaacggc gtgaacttcc    420

ccgccgacgg ccccgtgatg aagaagatga ccaccaactg ggaggccagc tgcgagaaga    480

tcatgcccgt gcctaagcag ggcatcctga agggcgacgt gagcatgtac ctgctgctga    540

aggacggcgg ccggtaccgg tgccagttcg acaccgtgta caaggccaag agcgtgccca    600

gcaagatgcc cgagtggcac ttcatccagc acaagctgct gcgggaggac cggagcgacg    660

ccaagaacca gaagtggcag ctgaccgagc acgccatcgc cttccccagc gccctggcct    720

gagagctcga atttccccga tcgttcaaac atttggcaat aaagtttctt aagattgaat    780

cctgttgccg gtcttgcgat gattatcata taatttctgt tgaattacgt taagcatgta    840

ataattaaca tgtaatgcat gacgttattt atgagatggg tttttatgat tagagtcccg    900

caattataca tttaatacgc gatagaaaac aaaatatagc gcgcaaacta ggataaatta    960

tcgcgcgcgg tgtcatctat gttactagat cgggaattct agtggccggc ccagctgata   1020

tccatcacac tggcggccgc tcgagttcta tagtgtcacc taaatcgtat gtgtatgata   1080

cataaggtta tgtattaatt gtagccgcgt tctaacgaca atatgtccat atggtgcact   1140

ctcagtacaa tctgctctga tgccgcatag ttaagccagc cccgacaccc gccaacaccc   1200

gctgacgcgc cctgacgggc ttgtctgctc ccggcatccg cttacagaca agctgtgacc   1260
```

-continued gtctccggga gctgcatgtg tcagaggttt tcaccgtcat caccgaaacg cgcgagacga 1320
aagggcctcg tgatacgcct atttttatag gttaatgtca tgaccaaaat cccttaacgt 1380
gagttttcgt tccactgagc gtcagacccc gtagaaaaga tcaaaggatc ttcttgagat 1440
cctttttttc tgcgcgtaat ctgctgcttg caaacaaaaa aaccaccgct accagcggtg 1500
gtttgtttgc cggatcaaga gctaccaact ctttttccga aggtaactgg cttcagcaga 1560
gcgcagatac caaatactgt ccttctagtg tagccgtagt taggccacca cttcaagaac 1620
tctgtagcac cgcctacata cctcgctctg ctaatcctgt taccagtggc tgctgccagt 1680
ggcgataagt cgtgtcttac cgggttggac tcaagacgat agttaccgga taaggcgcag 1740
cggtcgggct gaacgggggg ttcgtgcaca cagcccagct tggagcgaac gacctacacc 1800
gaactgagat acctacagcg tgagcattga gaaagcgcca cgcttcccga agggagaaag 1860
gcggacaggt atccggtaag cggcagggtc ggaacaggag agcgcacgag ggagcttcca 1920
gggggaaacg cctggtatct ttatagtcct gtcgggtttc gccacctctg acttgagcgt 1980
cgatttttgt gatgctcgtc aggggggcgg agcctatgga aaaacgccag caacgcggcc 2040
tttttacggt tcctggcctt ttgctggcct tttgctcaca tgttctttcc tgcgttatcc 2100
cctgattctg tggataaccg tattaccgcc tttgagtgag ctgataccgc tcgccgcagc 2160
cgaacgaccg agcgcagcga gtcagtgagc gaggaagcgg aagagcgccc aatacgcaaa 2220
ccgcctctcc ccgcgcgttg gccgattcat taatgcaggt tgatcagatc tcgatcccgc 2280
gaaattaata cgactcacta tagggagacc acaacggttt ccctctagaa ataattttgt 2340
ttaactttaa gaaggagata tacccatgga aaagcctgaa ctcaccgcga cgtctgtcga 2400
gaagtttctg atcgaaaagt tcgacagcgt ctccgacctg atgcagctct cggagggcga 2460
agaatctcgt gctttcagct tcgatgtagg agggcgtgga tatgtcctgc gggtaaatag 2520
ctgcgccgat ggtttctaca aagatcgtta tgtttatcgg cactttgcat cggccgcgct 2580
cccgattccg gaagtgcttg acattgggga attcagcgag agcctgacct attgcatctc 2640
ccgccgtgca cagggtgtca cgttgcaaga cctgcctgaa accgaactgc ccgctgttct 2700
gcagccggtc gcggaggcta tggatgcgat cgctgcggcc gatcttagcc agacgagcgg 2760
gttcggccca ttcggaccgc aaggaatcgg tcaatacact acatggcgtg atttcatatg 2820
cgcgattgct gatccccatg tgtatcactg gcaaactgtg atggacgaca ccgtcagtgc 2880
gtccgtcgcg caggctctcg atgagctgat gctttgggcc gaggactgcc ccgaagtccg 2940
gcacctcgtg cacgcggatt tcggctccaa caatgtcctg acggacaatg gccgcataac 3000
agcggtcatt gactggagcg aggcgatgtt cggggattcc caatacgagg tcgccaacat 3060
cttcttctgg aggccgtggt tggcttgtat ggagcagcag acgcgctact tcgagcggag 3120
gcatccggag cttgcaggat cgccgcggct ccgggcgtat atgctccgca ttggtcttga 3180
ccaactctat cagagcttgg ttgacggcaa tttcgatgat gcagcttggg cgcagggtcg 3240
atgcgacgca atcgtccgat ccggagccgg gactgtcggg cgtacacaaa tcgcccgcag 3300
aagcgcggcc gtctggaccg atggctgtgt agaagtactc gccgatagtg gaaaccgacg 3360
ccccagcact cgtccgaggg caaaggaata gtgaggtaca gcttggatcg atccggctgc 3420
taacaaagcc cgaaaggaag ctgagttggc tgctgccacc gctgagcaat aactagcata 3480
accccttggg gcctctaaac gggtcttgag gggttttttg ctgaaaggag gaactatatc 3540
cggatgatcg tcgaggcctc acgtgttaac aagcttgcat gcctgcaggt ttatcaacaa 3600
gtttgtacaa aaaagcaggc tccgaattcg ccctttacga atataacgaa aacaccgagt 3660
gaaaaaatgt tacgcagaaa agagatagat agaatgagaa gagagaaaat ataacagatt 3720
cgatataaaa tacaaagata tagaaatgat aatgtcgtag aaaatgttat atgaataagt 3780
gatctaacac agaaaaaaga aagaagtgag ttaattagac aaaaagagaa gaaacttgtg 3840
ttttgagaac aaaattgtaa cgaataatca aacactaaaa tgaacaatac tcagttactt 3900
acgatgactt gaacgatgtc ggcagaagtg ggaaataata aaaagtaagt ccatacaaaa 3960
taacgtgcca aattcatttt gggtgatgca gaaacctgcc aaaccacatg gckatatata 4020
tatatagaaa cagttgatca gttagcaacc ctttgccaac tctgatatat tatgtatttt 4080
tttttatgtt ttagttattt tattttattt tattcaaaat tttaatattt taaaatttaa 4140
aatctaacta atgtattttt taaaatatat tcttatttaa tattcacgtg ataaaatata 4200
aaatataaaa tatcaatata ttaaataaga atattttaat tcaaatataa tattttttaa 4260
ttttattaaa tatttattaa ttcatatata atattaaggt ataaactcat taattgtatc 4320
acgttgtagg tttgagcatg cggttattca attgcttgca ttaaatgaaa tcaaccagga 4380
actagctatc attccttagt tcacttttca cttaacgaac tcaaycagct ggctgaatct 4440
gaactctata tatagtcctt aaattcacaa atcataacat caaaaccatc acttcatact 4500
cactagtcac tatagctcac ccttgaagaa gtgcaatttc atcctctaac tcttccaaat 4560
ccaagggcga attcgaccca gcttt 4585

<210> SEQ ID NO 45
<211> LENGTH: 4396
<212> TYPE: DNA
<213> ORGANISM: Artificial
<220> FEATURE:
<223> OTHER INFORMATION: nucleotide sequence for QC267-3Y

<400> SEQUENCE: 45
cttgtacaaa gtggttgatg ggatccatgg cccacagcaa gcacggcctg aaggaggaga 60
tgaccatgaa gtaccacatg gagggctgcg tgaacggcca caagttcgtg atcaccggcg 120
agggcatcgg ctaccccttc aagggcaagc agaccatcaa cctgtgcgtg atcgagggcg 180 gcccccctgcc cttcagcgag gacatcctga gcgccggctt caagtacggc gaccggatct 240
tcaccgagta cccccaggac atcgtggact acttcaagaa cagctgcccc gccggctaca 300
cctggggccg gagcttcctg ttcgaggacg gcgccgtgtg catctgtaac gtggacatca 360
ccgtgagcgt gaaggagaac tgcatctacc acaagagcat cttcaacggc gtgaacttcc 420
ccgccgacgg ccccgtgatg aagaagatga ccaccaactg ggaggccagc tgcgagaaga 480
tcatgcccgt gcctaagcag ggcatcctga agggcgacgt gagcatgtac ctgctgctga 540
aggacggcgg ccggtaccgg tgccagttcg acaccgtgta caaggccaag agcgtgccca 600
gcaagatgcc cgagtggcac ttcatccagc acaagctgct gcgggaggac cggagcgacg 660
ccaagaacca gaagtggcag ctgaccgagc acgccatcgc cttccccagc gccctggcct 720
gagagctcga atttccccga tcgttcaaac atttggcaat aaagtttctt aagattgaat 780
cctgttgccg gtcttgcgat gattatcata taatttctgt tgaattacgt taagcatgta 840
ataattaaca tgtaatgcat gacgttattt atgagatggg tttttatgat tagagtcccg 900
caattataca tttaatacgc gatagaaaac aaaatatagc gcgcaaacta ggataaatta 960
tcgcgcgcgg tgtcatctat gttactagat cgggaattct agtggccggc ccagctgata 1020
tccatcacac tggcggccgc tcgagttcta tagtgtcacc taaatcgtat gtgtatgata 1080
cataaggtta tgtattaatt gtagccgcgt tctaacgaca atatgtccat atggtgcact 1140

```
ctcagtacaa tctgctctga tgccgcatag ttaagccagc cccgacaccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct atttttatag gttaatgtca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca cagcccagct tggagcgaac gacctacacc   1800
gaactgagat acctacagcg tgagcattga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040
tttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca aagatcgtta tgtttatcgg cactttgcat cggccgcgct   2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
gtccgtcgcg caggctctcg atgagctgat gctttgggcc gaggactgcc ccgaagtccg   2940
gcacctcgtg cacgcggatt tcggctccaa caatgtcctg acggacaatg gccgcataac   3000
agcggtcatt gactggagcg aggcgatgtt cggggattcc caatacgagg tcgccaacat   3060
cttcttctgg aggccgtggt tggcttgtat ggagcagcag acgcgctact tcgagcggag   3120
gcatccggag cttgcaggat cgccgcggct ccgggcgtat atgctccgca ttggtcttga   3180
ccaactctat cagagcttgg ttgacggcaa tttcgatgat gcagcttggg cgcagggtcg   3240
atgcgacgca atcgtccgat ccggagccgg gactgtcggg cgtacacaaa tcgcccgcag   3300
aagcgcggcc gtctggaccg atggctgtgt agaagtactc gccgatagtg gaaaccgacg   3360
ccccagcact cgtccgaggg caaaggaata gtgaggtaca gcttggatcg atccggctgc   3420
taacaaagcc cgaaaggaag ctgagttggc tgctgccacc gctgagcaat aactagcata   3480
accccttggg gcctctaaac gggtcttgag gggttttttg ctgaaaggag gaactatatc   3540
```

cggatgatcg tcgaggcctc acgtgttaac aagcttgcat gcctgcaggt ttatcaacaa 3600
gtttgtacaa aaaagcaggc tccgaattcg cccttagaga agaaacttgt gttttgagaa 3660
caaaattgta acgaataatc aaacactaaa atgaacaata ctcagttact tacgatgact 3720
tgaacgatgt cggcagaagt gggaaataat aaaaagtaag tccatacaaa ataacgtgcc 3780
aaattcattt tgggtgatgc agaaacctgc caaaccacat ggckatatat atatatagaa 3840
acagttgatc agttagcaac cctttgccaa ctctgatata ttatgtattt ttttttatgt 3900
tttagttatt ttattttatt ttattcaaaa ttttaatatt ttaaaattta aaatctaact 3960
aatgtatttt ttaaaatata ttcttattta atattcacgt gataaaatat aaaatataaa 4020
atatcaatat attaaataag aatattttaa ttcaaatata atattttta attttattaa 4080 atatttatta attcatatat aatattaagg tataaactca ttaattgtat cacgttgtag 4140
gtttgagcat gcggttattc aattgcttgc attaaatgaa atcaaccagg aactagctat 4200
cattccttag ttcacttttc acttaacgaa ctcaaycagc tggctgaatc tgaactctat 4260
atatagtcct taaattcaca aatcataaca tcaaaaccat cacttcatac tcactagtca 4320
ctatagctca cccttgaaga agtgcaattt catcctctaa ctcttccaaa tccaagggcg 4380
aattcgaccc agcttt 4396

<210> SEQ ID NO 46
<211> LENGTH: 4185
<212> TYPE: DNA
<213> ORGANISM: Artificial
<220> FEATURE:
<223> OTHER INFORMATION: nucleotide sequence for QC267-4Y

<400> SEQUENCE: 46
cttgtacaaa gtggttgatg ggatccatgg cccacagcaa gcacggcctg aaggaggaga 60
tgaccatgaa gtaccacatg gagggctgcg tgaacggcca caagttcgtg atcaccggcg 120
agggcatcgg ctaccccttc aagggcaagc agaccatcaa cctgtgcgtg atcgagggcg 180 gcccccctgcc cttcagcgag gacatcctga gcgccggctt caagtacggc gaccggatct 240
tcaccgagta cccccaggac atcgtggact acttcaagaa cagctgcccc gccggctaca 300
cctggggccg gagcttcctg ttcgaggacg gcgccgtgtg catctgtaac gtggacatca 360
ccgtgagcgt gaaggagaac tgcatctacc acaagagcat cttcaacggc gtgaacttcc 420
ccgccgacgg ccccgtgatg aagaagatga ccaccaactg ggaggccagc tgcgagaaga 480
tcatgcccgt gcctaagcag ggcatcctga agggcgacgt gagcatgtac ctgctgctga 540
aggacggcgg ccggtaccgg tgccagttcg acaccgtgta caaggccaag agcgtgccca 600
gcaagatgcc cgagtggcac ttcatccagc acaagctgct gcgggaggac cggagcgacg 660
ccaagaacca gaagtggcag ctgaccgagc acgccatcgc cttccccagc gccctggcct 720
gagagctcga atttccccga tcgttcaaac atttggcaat aaagtttctt aagattgaat 780
cctgttgccg gtcttgcgat gattatcata taatttctgt tgaattacgt taagcatgta 840
ataattaaca tgtaatgcat gacgttattt atgagatggg tttttatgat tagagtcccg 900
caattataca tttaatacgc gatagaaaac aaaatatagc gcgcaaacta ggataaatta 960
tcgcgcgcgg tgtcatctat gttactagat cgggaattct agtggccggc ccagctgata 1020
tccatcacac tggcggccgc tcgagttcta tagtgtcacc taaatcgtat gtgtatgata 1080
cataaggtta tgtattaatt gtagccgcgt tctaacgaca atatgtccat atggtgcact 1140
ctcagtacaa tctgctctga tgccgcatag ttaagccagc cccgacaccc gccaacaccc 1200

```
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct atttttatag gttaatgtca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca cagcccagct tggagcgaac gacctacacc   1800
gaactgagat acctacagcg tgagcattga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040
tttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca aagatcgtta tgtttatcgg cactttgcat cggccgcgct   2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
gtccgtcgcg caggctctcg atgagctgat gctttgggcc gaggactgcc ccgaagtccg   2940
gcacctcgtg cacgcggatt tcggctccaa caatgtcctg acggacaatg gccgcataac   3000
agcggtcatt gactggagcg aggcgatgtt cggggattcc caatacgagg tcgccaacat   3060
cttcttctgg aggccgtggt tggcttgtat ggagcagcag acgcgctact tcgagcggag   3120
gcatccggag cttgcaggat cgccgcggct ccgggcgtat atgctccgca ttggtcttga   3180
ccaactctat cagagcttgg ttgacggcaa tttcgatgat gcagcttggg cgcagggtcg   3240
atgcgacgca atcgtccgat ccggagccgg gactgtcggg cgtacacaaa tcgcccgcag   3300
aagcgcggcc gtctggaccg atggctgtgt agaagtactc gccgatagtg gaaaccgacg   3360
ccccagcact cgtccgaggg caaaggaata gtgaggtaca gcttggatcg atccggctgc   3420
taacaaagcc cgaaaggaag ctgagttggc tgctgccacc gctgagcaat aactagcata   3480
accccttggg gcctctaaac gggtcttgag gggttttttg ctgaaaggag gaactatatc   3540
cggatgatcg tcgaggcctc acgtgttaac aagcttgcat gcctgcaggt ttatcaacaa   3600
```

gtttgtacaa aaaagcaggc tccgaattcg cccttgatca gttagcaacc ctttgccaac 3660
tctgatatat tatgtatttt tttttatgtt ttagttattt tattttattt tattcaaaat 3720
tttaatattt taaaatttaa aatctaacta atgtattttt taaaatatat tcttatttaa 3780
tattcacgtg ataaaatata aaatataaaa tatcaatata ttaaataaga atattttaat 3840
tcaaatataa tattttttaa ttttattaaa tatttattaa ttcatatata atattaaggt 3900
ataaactcat taattgtatc acgttgtagg tttgagcatg cggttattca attgcttgca 3960
ttaaatgaaa tcaaccagga actagctatc attccttagt tcacttttca cttaacgaac 4020
tcaaycagct ggctgaatct gaactctata tatagtcctt aaattcacaa atcataacat 4080
caaaaccatc acttcatact cactagtcac tatagctcac ccttgaagaa gtgcaatttc 4140
atcctctaac tcttccaaat ccaagggcga attcgaccca gcttt 4185

<210> SEQ ID NO 47
<211> LENGTH: 3915
<212> TYPE: DNA
<213> ORGANISM: Artificial
<220> FEATURE:
<223> OTHER INFORMATION: nucleotide sequence for QC267-5Y

<400> SEQUENCE: 47
cttgtacaaa gtggttgatg ggatccatgg cccacagcaa gcacggcctg aaggaggaga 60
tgaccatgaa gtaccacatg gagggctgcg tgaacggcca caagttcgtg atcaccggcg 120
agggcatcgg ctaccccttc aagggcaagc agaccatcaa cctgtgcgtg atcgagggcg 180 gcccccctgcc cttcagcgag gacatcctga gcgccggctt caagtacggc gaccggatct 240
tcaccgagta cccccaggac atcgtggact acttcaagaa cagctgcccc gccggctaca 300
cctggggccg gagcttcctg ttcgaggacg gcgccgtgtg catctgtaac gtggacatca 360
ccgtgagcgt gaaggagaac tgcatctacc acaagagcat cttcaacggc gtgaacttcc 420
ccgccgacgg ccccgtgatg aagaagatga ccaccaactg ggaggccagc tgcgagaaga 480
tcatgcccgt gcctaagcag ggcatcctga agggcgacgt gagcatgtac ctgctgctga 540
aggacggcgg ccggtaccgg tgccagttcg acaccgtgta caaggccaag agcgtgccca 600
gcaagatgcc cgagtggcac ttcatccagc acaagctgct gcgggaggac cggagcgacg 660
ccaagaacca gaagtggcag ctgaccgagc acgccatcgc cttccccagc gccctggcct 720
gagagctcga atttccccga tcgttcaaac atttggcaat aaagtttctt aagattgaat 780
cctgttgccg gtcttgcgat gattatcata taatttctgt tgaattacgt taagcatgta 840
ataattaaca tgtaatgcat gacgttattt atgagatggg tttttatgat tagagtcccg 900
caattataca tttaatacgc gatagaaaac aaaatatagc gcgcaaacta ggataaatta 960
tcgcgcgcgg tgtcatctat gttactagat cgggaattct agtggccggc ccagctgata 1020
tccatcacac tggcggccgc tcgagttcta tagtgtcacc taaatcgtat gtgtatgata 1080
cataaggtta tgtattaatt gtagccgcgt tctaacgaca atatgtccat atggtgcact 1140
ctcagtacaa tctgctctga tgccgcatag ttaagccagc cccgacaccc gccaacaccc 1200
gctgacgcgc cctgacgggc ttgtctgctc ccggcatccg cttacagaca agctgtgacc 1260
gtctccggga gctgcatgtg tcagaggttt tcaccgtcat caccgaaacg cgcgagacga 1320
aagggcctcg tgatacgcct atttttatag gttaatgtca tgaccaaaat cccttaacgt 1380
gagttttcgt tccactgagc gtcagacccc gtagaaaaga tcaaaggatc ttcttgagat 1440
cctttttttc tgcgcgtaat ctgctgcttg caaacaaaaa aaccaccgct accagcggtg 1500
gtttgtttgc cggatcaaga gctaccaact ctttttccga aggtaactgg cttcagcaga 1560
gcgcagatac caaatactgt ccttctagtg tagccgtagt taggccacca cttcaagaac 1620
tctgtagcac cgcctacata cctcgctctg ctaatcctgt taccagtggc tgctgccagt 1680
ggcgataagt cgtgtcttac cgggttggac tcaagacgat agttaccgga taaggcgcag 1740
cggtcgggct gaacgggggg ttcgtgcaca cagcccagct tggagcgaac gacctacacc 1800
gaactgagat acctacagcg tgagcattga gaaagcgcca cgcttcccga agggagaaag 1860
gcggacaggt atccggtaag cggcagggtc ggaacaggag agcgcacgag ggagcttcca 1920
gggggaaacg cctggtatct ttatagtcct gtcgggtttc gccacctctg acttgagcgt 1980
cgatttttgt gatgctcgtc aggggggcgg agcctatgga aaaacgccag caacgcggcc 2040
tttttacggt tcctggcctt ttgctggcct tttgctcaca tgttctttcc tgcgttatcc 2100
cctgattctg tggataaccg tattaccgcc tttgagtgag ctgataccgc tcgccgcagc 2160
cgaacgaccg agcgcagcga gtcagtgagc gaggaagcgg aagagcgccc aatacgcaaa 2220
ccgcctctcc ccgcgcgttg gccgattcat taatgcaggt tgatcagatc tcgatcccgc 2280
gaaattaata cgactcacta tagggagacc acaacggttt ccctctagaa ataattttgt 2340
ttaactttaa gaaggagata tacccatgga aaagcctgaa ctcaccgcga cgtctgtcga 2400
gaagtttctg atcgaaaagt tcgacagcgt ctccgacctg atgcagctct cggagggcga 2460
agaatctcgt gctttcagct tcgatgtagg agggcgtgga tatgtcctgc gggtaaatag 2520
ctgcgccgat ggtttctaca aagatcgtta tgtttatcgg cactttgcat cggccgcgct 2580
cccgattccg gaagtgcttg acattgggga attcagcgag agcctgacct attgcatctc 2640
ccgccgtgca cagggtgtca cgttgcaaga cctgcctgaa accgaactgc ccgctgttct 2700
gcagccggtc gcggaggcta tggatgcgat cgctgcggcc gatcttagcc agacgagcgg 2760
gttcggccca ttcggaccgc aaggaatcgg tcaatacact acatggcgtg atttcatatg 2820
cgcgattgct gatccccatg tgtatcactg gcaaactgtg atggacgaca ccgtcagtgc 2880
gtccgtcgcg caggctctcg atgagctgat gctttgggcc gaggactgcc ccgaagtccg 2940
gcacctcgtg cacgcggatt tcggctccaa caatgtcctg acggacaatg gccgcataac 3000
agcggtcatt gactggagcg aggcgatgtt cggggattcc caatacgagg tcgccaacat 3060
cttcttctgg aggccgtggt tggcttgtat ggagcagcag acgcgctact tcgagcggag 3120
gcatccggag cttgcaggat cgccgcggct ccgggcgtat atgctccgca ttggtcttga 3180
ccaactctat cagagcttgg ttgacggcaa tttcgatgat gcagcttggg cgcagggtcg 3240
atgcgacgca atcgtccgat ccggagccgg gactgtcggg cgtacacaaa tcgcccgcag 3300
aagcgcggcc gtctggaccg atggctgtgt agaagtactc gccgatagtg gaaaccgacg 3360
ccccagcact cgtccgaggg caaaggaata gtgaggtaca gcttggatcg atccggctgc 3420
taacaaagcc cgaaaggaag ctgagttggc tgctgccacc gctgagcaat aactagcata 3480
accccttggg gcctctaaac gggtcttgag gggttttttg ctgaaaggag gaactatatc 3540
cggatgatcg tcgaggcctc acgtgttaac aagcttgcat gcctgcaggt ttatcaacaa 3600
gtttgtacaa aaaagcaggc tccgaattcg ccccttctcat taattgtatc acgttgtagg 3660
tttgagcatg cggttattca attgcttgca ttaaatgaaa tcaaccagga actagctatc 3720
attccttagt tcacttttca cttaacgaac tcaaycagct ggctgaatct gaactctata 3780
tatagtcctt aaattcacaa atcataacat caaaaccatc acttcatact cactagtcac 3840
tatagctcac ccttgaagaa gtgcaatttc atcctctaac tcttccaaat ccaagggcga 3900
attcgaccca gcttt 3915

<210> SEQ ID NO 48
<211> LENGTH: 5286
<212> TYPE: DNA
<213> ORGANISM: Artificial
<220> FEATURE:
<223> OTHER INFORMATION: nucleotide sequence for QC330

<400> SEQUENCE: 48
atcaacaagt ttgtacaaaa aagctgaacg agaaacgtaa aatgatataa atatcaatat 60
attaaattag attttgcata aaaaacagac tacataatac tgtaaaacac aacatatcca 120
gtcatattgg cggccgcatt aggcacccca ggctttacac tttatgcttc cggctcgtat 180
aatgtgtgga ttttgagtta ggatccgtcg agattttcag gagctaagga agctaaaatg 240
gagaaaaaaa tcactggata taccaccgtt gatatatccc aatggcatcg taaagaacat 300
tttgaggcat ttcagtcagt tgctcaatgt acctataacc agaccgttca gctggatatt 360
acggcctttt taaagaccgt aaagaaaaat aagcacaagt tttatccggc ctttattcac 420
attcttgccc gcctgatgaa tgctcatccg gaattccgta tggcaatgaa agacggtgag 480
ctggtgatat gggatagtgt tcacccttgt tacaccgttt tccatgagca aactgaaacg 540
ttttcatcgc tctggagtga ataccacgac gatttccggc agtttctaca catatattcg 600
caagatgtgg cgtgttacgg tgaaaacctg gcctatttcc ctaaagggtt tattgagaat 660
atgtttttcg tctcagccaa tccctgggtg agtttcacca gttttgattt aaacgtggcc 720
aatatggaca acttcttcgc ccccgttttc accatgggca aatattatac gcaaggcgac 780
aaggtgctga tgccgctggc gattcaggtt catcatgccg tttgtgatgg cttccatgtc 840
ggcagaatgc ttaatgaatt acaacagtac tgcgatgagt ggcagggcgg ggcgtaaaga 900
tctggatccg gcttactaaa agccagataa cagtatgcgt atttgcgcgc tgatttttgc 960
ggtataagaa tatatactga tatgtatacc cgaagtatgt caaaaagagg tatgctatga 1020
agcagcgtat tacagtgaca gttgacagcg acagctatca gttgctcaag gcatatatga 1080
tgtcaatatc tccggtctgg taagcacaac catgcagaat gaagcccgtc gtctgcgtgc 1140
cgaacgctgg aaagcggaaa atcaggaagg gatggctgag gtcgcccggt ttattgaaat 1200
gaacggctct tttgctgacg agaacagggg ctggtgaaat gcagtttaag gtttacacct 1260
ataaaagaga gagccgttat cgtctgtttg tggatgtaca gagtgatatt attgacacgc 1320
ccgggcgacg gatggtgatc cccctggcca gtgcacgtct gctgtcagat aaagtctccc 1380
gtgaacttta cccggtggtg catatcgggg atgaaagctg gcgcatgatg accaccgata 1440
tggccagtgt gccggtctcc gttatcgggg aagaagtggc tgatctcagc caccgcgaaa 1500
atgacatcaa aaacgccatt aacctgatgt tctggggaat ataaatgtca ggctccctta 1560
tacacagcca gtctgcaggt cgaccatagt gactggatat gttgtgtttt acagtattat 1620
gtagtctgtt ttttatgcaa aatctaattt aatatattga tatttatatc attttacgtt 1680
tctcgttcag ctttcttgta caaagtggtt gatgggatcc atggcccaca gcaagcacgg 1740
cctgaaggag gagatgacca tgaagtacca catggagggc tgcgtgaacg gccacaagtt 1800
cgtgatcacc ggcgagggca tcggctaccc cttcaagggc aagcagacca tcaacctgtg 1860
cgtgatcgag ggcggccccc tgcccttcag cgaggacatc ctgagcgccg gcttcaagta 1920
cggcgaccgg atcttcaccg agtaccccca ggacatcgtg gactacttca agaacagctg 1980
ccccgccggc tacacctggg gccggagctt cctgttcgag gacggcgccg tgtgcatctg 2040

```
taacgtggac atcaccgtga gcgtgaagga gaactgcatc taccacaaga gcatcttcaa   2100
cggcgtgaac ttccccgccg acggccccgt gatgaagaag atgaccacca actgggaggc   2160
cagctgcgag aagatcatgc ccgtgcctaa gcagggcatc ctgaagggcg acgtgagcat   2220
gtacctgctg ctgaaggacg gcggccggta ccggtgccag ttcgacaccg tgtacaaggc   2280
caagagcgtg cccagcaaga tgcccgagtg gcacttcatc cagcacaagc tgctgcggga   2340
ggaccggagc gacgccaaga accagaagtg gcagctgacc gagcacgcca tcgccttccc   2400
cagcgccctg gcctgagagc tcgaatttcc ccgatcgttc aaacatttgg caataaagtt   2460
tcttaagatt gaatcctgtt gccggtcttg cgatgattat catataattt ctgttgaatt   2520
acgttaagca tgtaataatt aacatgtaat gcatgacgtt atttatgaga tgggttttta   2580
tgattagagt cccgcaatta tacatttaat acgcgataga aaacaaaata tagcgcgcaa   2640
actaggataa attatcgcgc gcggtgtcat ctatgttact agatcgggaa ttctagtggc   2700
cggcccagct gatatccatc acactggcgg ccgctcgagt tctatagtgt cacctaaatc   2760
gtatgtgtat gatacataag gttatgtatt aattgtagcc gcgttctaac gacaatatgt   2820
ccatatggtg cactctcagt acaatctgct ctgatgccgc atagttaagc cagccccgac   2880
acccgccaac acccgctgac gcgccctgac gggcttgtct gctcccggca tccgcttaca   2940
gacaagctgt gaccgtctcc gggagctgca tgtgtcagag gttttcaccg tcatcaccga   3000
aacgcgcgag acgaaagggc ctcgtgatac gcctattttt ataggttaat gtcatgacca   3060
aaatccctta acgtgagttt tcgttccact gagcgtcaga ccccgtagaa aagatcaaag   3120
gatcttcttg agatcctttt tttctgcgcg taatctgctg cttgcaaaca aaaaaaccac   3180
cgctaccagc ggtggtttgt ttgccggatc aagagctacc aactcttttt ccgaaggtaa   3240
ctggcttcag cagagcgcag ataccaaata ctgtccttct agtgtagccg tagttaggcc   3300
accacttcaa gaactctgta gcaccgccta catacctcgc tctgctaatc ctgttaccag   3360
tggctgctgc cagtggcgat aagtcgtgtc ttaccgggtt ggactcaaga cgatagttac   3420
cggataaggc gcagcggtcg ggctgaacgg ggggttcgtg cacacagccc agcttggagc   3480
gaacgaccta caccgaactg agatacctac agcgtgagca ttgagaaagc gccacgcttc   3540
ccgaagggag aaaggcggac aggtatccgg taagcggcag ggtcggaaca ggagagcgca   3600
cgagggagct tccaggggga aacgcctggt atctttatag tcctgtcggg tttcgccacc   3660
tctgacttga gcgtcgattt ttgtgatgct cgtcaggggg gcggagccta tggaaaaacg   3720
ccagcaacgc ggccttttta cggttcctgg ccttttgctg gccttttgct cacatgttct   3780
ttcctgcgtt atcccctgat tctgtggata accgtattac cgcctttgag tgagctgata   3840
ccgctcgccg cagccgaacg accgagcgca gcgagtcagt gagcgaggaa gcggaagagc   3900
gcccaatacg caaaccgcct ctccccgcgc gttggccgat tcattaatgc aggttgatca   3960
gatctcgatc ccgcgaaatt aatacgactc actataggga gaccacaacg gtttccctct   4020
agaaataatt ttgtttaact ttaagaagga gatataccca tggaaaagcc tgaactcacc   4080
gcgacgtctg tcgagaagtt tctgatcgaa aagttcgaca gcgtctccga cctgatgcag   4140
ctctcggagg gcgaagaatc tcgtgctttc agcttcgatg taggagggcg tggatatgtc   4200
ctgcgggtaa atagctgcgc cgatggtttc tacaaagatc gttatgttta tcggcacttt   4260
gcatcggccg cgctcccgat tccggaagtg cttgacattg gggaattcag cgagagcctg   4320
acctattgca tctcccgccg tgcacagggt gtcacgttgc aagacctgcc tgaaaccgaa   4380
ctgcccgctg ttctgcagcc ggtcgcggag gctatggatg cgatcgctgc ggccgatctt   4440
```

```
agccagacga gcgggttcgg cccattcgga ccgcaaggaa tcggtcaata cactacatgg   4500
cgtgatttca tatgcgcgat tgctgatccc catgtgtatc actggcaaac tgtgatggac   4560
gacaccgtca gtgcgtccgt cgcgcaggct ctcgatgagc tgatgctttg ggccgaggac   4620
tgccccgaag tccggcacct cgtgcacgcg gatttcggct ccaacaatgt cctgacggac   4680
aatggccgca taacagcggt cattgactgg agcgaggcga tgttcgggga ttcccaatac   4740
gaggtcgcca acatcttctt ctggaggccg tggttggctt gtatggagca gcagacgcgc   4800
tacttcgagc ggaggcatcc ggagcttgca ggatcgccgc ggctccgggc gtatatgctc   4860
cgcattggtc ttgaccaact ctatcagagc ttggttgacg gcaatttcga tgatgcagct   4920
tgggcgcagg gtcgatgcga cgcaatcgtc cgatccggag ccgggactgt cgggcgtaca   4980
caaatcgccc gcagaagcgc ggccgtctgg accgatggct gtgtagaagt actcgccgat   5040
agtggaaacc gacgccccag cactcgtccg agggcaaagg aatagtgagg tacagcttgg   5100
atcgatccgg ctgctaacaa agcccgaaag gaagctgagt tggctgctgc caccgctgag   5160
caataactag cataacccct tggggcctct aaacgggtct tgaggggttt tttgctgaaa   5220
ggaggaacta tatccggatg atcgtcgagg cctcacgtgt taacaagctt gcatgcctgc   5280
aggttt                                                              5286
```

```
<210> SEQ ID NO 49
<211> LENGTH: 4157
<212> TYPE: DNA
<213> ORGANISM: Artificial
<220> FEATURE:
<223> OTHER INFORMATION: nucleotide sequence for pZSL90

<400> SEQUENCE: 49
```

```
gatccatggc ccacagcaag cacggcctga aggaggagat gaccatgaag taccacatgg     60
agggctgcgt gaacggccac aagttcgtga tcaccggcga gggcatcggc taccccttca    120
agggcaagca gaccatcaac ctgtgcgtga tcgagggcgg cccccctgccc ttcagcgagg    180
acatcctgag cgccggcttc aagtacggcg accggatctt caccgagtac ccccaggaca    240
tcgtggacta cttcaagaac agctgccccg ccggctacac ctggggccgg agcttcctgt    300
tcgaggacgg cgccgtgtgc atctgtaacg tggacatcac cgtgagcgtg aaggagaact    360
gcatctacca caagagcatc ttcaacggcg tgaacttccc cgccgacggc cccgtgatga    420
agaagatgac caccaactgg gaggccagct gcgagaagat catgcccgtg cctaagcagg    480
gcatcctgaa gggcgacgtg agcatgtacc tgctgctgaa ggacggcggc cggtaccggt    540
gccagttcga caccgtgtac aaggccaaga gcgtgcccag caagatgccc gagtggcact    600
tcatccagca caagctgctg cgggaggacc ggagcgacgc caagaaccag aagtggcagc    660
tgaccgagca cgccatcgcc ttccccagcg ccctggcctg agagctcgaa tttccccgat    720
cgttcaaaca tttggcaata aagtttctta agattgaatc ctgttgccgg tcttgcgatg    780
attatcatat aatttctgtt gaattacgtt aagcatgtaa taattaacat gtaatgcatg    840
acgttattta tgagatgggt ttttatgatt agagtcccgc aattatacat ttaatacgcg    900
atagaaaaca aaatatagcg cgcaaactag gataaattat cgcgcgcggt gtcatctatg    960
ttactagatc gggaattcta gtggccggcc cagctgatat ccatcacact ggcggccgct   1020
cgagttctat agtgtcacct aaatcgtatg tgtatgatac ataaggttat gtattaattg   1080
tagccgcgtt ctaacgacaa tatgtccata tggtgcactc tcagtacaat ctgctctgat   1140
gccgcatagt taagccagcc ccgacacccg ccaacacccg ctgacgcgcc ctgacgggct   1200
```

```
tgtctgctcc cggcatccgc ttacagacaa gctgtgaccg tctccgggag ctgcatgtgt   1260
cagaggtttt caccgtcatc accgaaacgc gcgagacgaa agggcctcgt gatacgccta   1320
tttttatagg ttaatgtcat gaccaaaatc ccttaacgtg agttttcgtt ccactgagcg   1380
tcagaccccg tagaaaagat caaaggatct tcttgagatc cttttttct gcgcgtaatc   1440
tgctgcttgc aaacaaaaaa accaccgcta ccagcggtgg tttgtttgcc ggatcaagag   1500
ctaccaactc tttttccgaa ggtaactggc ttcagcagag cgcagatacc aaatactgtc   1560
cttctagtgt agccgtagtt aggccaccac ttcaagaact ctgtagcacc gcctacatac   1620
ctcgctctgc taatcctgtt accagtggct gctgccagtg gcgataagtc gtgtcttacc   1680
gggttggact caagacgata gttaccggat aaggcgcagc ggtcgggctg aacggggggt   1740
tcgtgcacac agcccagctt ggagcgaacg acctacaccg aactgagata cctacagcgt   1800
gagcattgag aaagcgccac gcttcccgaa gggagaaagg cggacaggta tccggtaagc   1860
ggcagggtcg gaacaggaga gcgcacgagg gagcttccag ggggaaacgc ctggtatctt   1920
tatagtcctg tcgggtttcg ccacctctga cttgagcgtc gatttttgtg atgctcgtca   1980
gggggcgga gcctatggaa aaacgccagc aacgcggcct ttttacggtt cctggccttt   2040
tgctggcctt ttgctcacat gttctttcct gcgttatccc ctgattctgt ggataaccgt   2100
attaccgcct ttgagtgagc tgataccgct cgccgcagcc gaacgaccga gcgcagcgag   2160
tcagtgagcg aggaagcgga agagcgccca atacgcaaac cgcctctccc cgcgcgttgg   2220
ccgattcatt aatgcaggtt gatcagatct cgatcccgcg aaattaatac gactcactat   2280
agggagacca caacggtttc cctctagaaa taattttgtt taactttaag aaggagatat   2340
acccatggaa aagcctgaac tcaccgcgac gtctgtcgag aagtttctga tcgaaaagtt   2400
cgacagcgtc tccgacctga tgcagctctc ggagggcgaa gaatctcgtg ctttcagctt   2460
cgatgtagga gggcgtggat atgtcctgcg ggtaaatagc tgcgccgatg gtttctacaa   2520
agatcgttat gtttatcggc actttgcatc ggccgcgctc ccgattccgg aagtgcttga   2580
cattggggaa ttcagcgaga gcctgaccta ttgcatctcc cgccgtgcac agggtgtcac   2640
gttgcaagac ctgcctgaaa ccgaactgcc cgctgttctg cagccggtcg cggaggctat   2700
ggatgcgatc gctgcggccg atcttagcca gacgagcggg ttcggcccat tcggaccgca   2760
aggaatcggt caatacacta catggcgtga tttcatatgc gcgattgctg atccccatgt   2820
gtatcactgg caaactgtga tggacgacac cgtcagtgcg tccgtcgcgc aggctctcga   2880
tgagctgatg ctttgggccg aggactgccc cgaagtccgg cacctcgtgc acgcggattt   2940
cggctccaac aatgtcctga cggacaatgg ccgcataaca gcggtcattg actggagcga   3000
ggcgatgttc ggggattccc aatacgaggt cgccaacatc ttcttctgga ggccgtggtt   3060
ggcttgtatg gagcagcaga cgcgctactt cgagcggagg catccggagc ttgcaggatc   3120
gccgcggctc cgggcgtata tgctccgcat tggtcttgac caactctatc agagcttggt   3180
tgacggcaat ttcgatgatg cagcttgggc gcagggtcga tgcgacgcaa tcgtccgatc   3240
cggagccggg actgtcgggc gtacacaaat cgcccgcaga agcgcggccg tctggaccga   3300
tggctgtgta gaagtactcg ccgatagtgg aaaccgacgc cccagcactc gtccgagggc   3360
aaaggaatag tgaggtacag cttggatcga tccggctgct aacaaagccc gaaaggaagc   3420
tgagttggct gctgccaccg ctgagcaata actagcataa ccccttgggg cctctaaacg   3480
ggtcttgagg ggttttttgc tgaaaggagg aactatatcc ggatgatcgt cgaggcctca   3540
cgtgttaaca agcttgcatg cctgcaggtt taaacagtcg actctagaga tccgtcaaca   3600
```

tggtggagca cgacactctc gtctactcca agaatatcaa agatacagtc tcagaagacc 3660
aaagggctat tgagactttt caacaaaggg taatatcggg aaacctcctc ggattccatt 3720
gcccagctat ctgtcacttc atcaaaagga cagtagaaaa ggaaggtggc acctacaaat 3780
gccatcattg cgataaagga aaggctatcg ttcaagatgc ctctgccgac agtggtccca 3840
aagatggacc cccacccacg aggagcatcg tggaaaaaga agacgttcca accacgtctt 3900
caaagcaagt ggattgatgt gatgatccta tgcgtatggt atgacgtgtg ttcaagatga 3960
tgacttcaaa cctacctatg acgtatggta tgacgtgtgt cgactgatga cttagatcca 4020
ctcgagcggc tataaatacg tacctacgca ccctgcgcta ccatccctag agctgcagct 4080
tatttttaca acaattacca acaacaacaa acaacaaaca acattacaat tactatttac 4140
aattacagtc gacccgg 4157

<210> SEQ ID NO 50
<211> LENGTH: 3291
<212> TYPE: DNA
<213> ORGANISM: Artificial
<220> FEATURE:
<223> OTHER INFORMATION: nucleotide sequence for QC299i

<400> SEQUENCE: 50
ccgggatcca tggcccacag caagcacggc ctgaaggagg agatgaccat gaagtaccac 60
atggagggct gcgtgaacgg ccacaagttc gtgatcaccg gcgagggcat cggctacccc 120
ttcaagggca agcagaccat caacctgtgc gtgatcgagg gcggccccct gcccttcagc 180
gaggacatcc tgagcgccgg cttcaagtac ggcgaccgga tcttcaccga gtacccccag 240
gacatcgtgg actacttcaa gaacagctgc cccgccggct acacctgggg ccggagcttc 300
ctgttcgagg acggcgccgt gtgcatctgt aacgtggaca tcaccgtgag cgtgaaggag 360
aactgcatct accacaagag catcttcaac ggcgtgaact tccccgccga cggccccgtg 420
atgaagaaga tgaccaccaa ctgggaggcc agctgcgaga agatcatgcc cgtgcctaag 480
cagggcatcc tgaagggcga cgtgagcatg tacctgctgc tgaaggacgg cggccggtac 540
cggtgccagt tcgacaccgt gtacaaggcc aagagcgtgc ccagcaagat gcccgagtgg 600
cacttcatcc agcacaagct gctgcgggag gaccggagcg acgccaagaa ccagaagtgg 660
cagctgaccg agcacgccat cgccttcccc agcgccctgg cctgagagct cgaatttccc 720
cgatcgttca aacatttggc aataaagttt cttaagattg aatcctgttg ccggtcttgc 780
gatgattatc atataatttc tgttgaatta cgttaagcat gtaataatta acatgtaatg 840
catgacgtta tttatgagat gggtttttat gattagagtc ccgcaattat acatttaata 900
cgcgatagaa aacaaaatat agcgcgcaaa ctaggataaa ttatcgcgcg cggtgtcatc 960
tatgttacta gatcgggaat tctagtggcc ggcccagctg atatccatca cactggcggc 1020
cgcactcgac tgaattggtt ccggcgccag cctgcttttt tgtacaaagt tggcattata 1080
aaaaagcatt gcttatcaat ttgttgcaac gaacaggtca ctatcagtca aaataaaatc 1140
attatttggg gcccgagctt aagtaactaa ctaacaggaa gagtttgtag aaacgcaaaa 1200
aggccatccg tcaggatggc cttctgctta gtttgatgcc tggcagttta tggcgggcgt 1260
cctgcccgcc accctccggg ccgttgcttc acaacgttca aatccgctcc cggcggattt 1320
gtcctactca ggagagcgtt caccgacaaa caacagataa aacgaaaggc ccagtcttcc 1380
gactgagcct ttcgttttat ttgatgcctg gcagttccct actctcgctt agtagttaga 1440
cgtccccgag atccatgcta gcggtaatac ggttatccac agaatcaggg gataacgcag 1500

-continued

```
gaaagaacat gtgagcaaaa ggccagcaaa aggccaggaa ccgtaaaaag gccgcgttgc   1560
tggcgttttt ccataggctc cgcccccctg acgagcatca caaaaatcga cgctcaagtc   1620
agaggtggcg aaacccgaca ggactataaa gataccaggc gtttccccct ggaagctccc   1680
tcgtgcgctc tcctgttccg accctgccgc ttaccggata cctgtccgcc tttctccctt   1740
cgggaagcgt ggcgctttct catagctcac gctgtaggta tctcagttcg gtgtaggtcg   1800
ttcgctccaa gctgggctgt gtgcacgaac cccccgttca gcccgaccgc tgcgccttat   1860
ccggtaacta tcgtcttgag tccaacccgg taagacacga cttatcgcca ctggcagcag   1920
ccactggtaa caggattagc agagcgaggt atgtaggcgg tgctacagag ttcttgaagt   1980
ggtggcctaa ctacggctac actagaagaa cagtatttgg tatctgcgct ctgctgaagc   2040
cagttacctt cggaaaaaga gttggtagct cttgatccgg caaacaaacc accgctggta   2100
gcggtggttt ttttgtttgc aagcagcaga ttacgcgcag aaaaaaagga tctcaagaag   2160
atcctttgat cttttctacg gggtctgacg ctcagtggaa cggggcccaa tctgaataat   2220
gttacaacca attaaccaat tctgattaga aaaactcatc gagcatcaaa tgaaactgca   2280
atttattcat atcaggatta tcaataccat atttttgaaa aagccgtttc tgtaatgaag   2340
gagaaaactc accgaggcag ttccatagga tggcaagatc ctggtatcgg tctgcgattc   2400
cgactcgtcc aacatcaata caacctatta atttcccctc gtcaaaaata aggttatcaa   2460
gtgagaaatc accatgagtg acgactgaat ccggtgagaa tggcaaaagt ttatgcattt   2520
ctttccagac ttgttcaaca ggccagccat tacgctcgtc atcaaaatca ctcgcatcaa   2580
ccaaaccgtt attcattcgt gattgcgcct gagcgagacg aaatacgcga tcgctgttaa   2640
aaggacaatt acaaacagga atcgaatgca accggcgcag gaacactgcc agcgcatcaa   2700
caatattttc acctgaatca ggatattctt ctaatacctg gaatgctgtt tttccgggga   2760
tcgcagtggt gagtaaccat gcatcatcag gagtacggat aaaatgcttg atggtcggaa   2820
gaggcataaa ttccgtcagc cagtttagtc tgaccatctc atctgtaaca tcattggcaa   2880
cgctaccttt gccatgtttc agaaacaact ctggcgcatc gggcttccca tacaagcgat   2940
agattgtcgc acctgattgc ccgacattat cgcgagccca tttataccca tataaatcag   3000
catccatgtt ggaatttaat cgcggcctcg acgtttcccg ttgaatatgg ctcataacac   3060
cccttgtatt actgtttatg taagcagaca gttttattgt tcatgatgat atatttttat   3120
cttgtgcaat gtaacatcag agattttgag acacgggcca gagctgcagc tggatggcaa   3180
ataatgattt tattttgact gatagtgacc tgttcgttgc aacaaattga taagcaatgc   3240
tttcttataa tgccaacttt gtacaagaaa gctgggtcta gatatctcga c            3291
```